US009623095B2

(12) United States Patent
Kallen et al.

(10) Patent No.: US 9,623,095 B2
(45) Date of Patent: Apr. 18, 2017

(54) VACCINATION IN NEWBORNS AND INFANTS

(75) Inventors: Karl-Josef Kallen, Tuebingen (DE); Thomas Kramps, Tuebingen (DE); Margit Schnee, Constance (DE); Benjamin Petsch, Tuebingen (DE); Lothar Stitz, Rottenburg (DE)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 13/824,705

(22) PCT Filed: Feb. 29, 2012

(86) PCT No.: PCT/EP2012/000877
§ 371 (c)(1),
(2), (4) Date: Jul. 10, 2013

(87) PCT Pub. No.: WO2012/116810
PCT Pub. Date: Sep. 7, 2012

(65) Prior Publication Data
US 2013/0336998 A1   Dec. 19, 2013

(30) Foreign Application Priority Data

Mar. 2, 2011   (WO) .................. PCT/EP2011/001047

(51) Int. Cl.
*A61K 39/145*   (2006.01)
*A61K 48/00*   (2006.01)
(Continued)

(52) U.S. Cl.
CPC .............. *A61K 39/00* (2013.01); *A61K 39/12* (2013.01); *A61K 39/145* (2013.01); *A61K 45/06* (2013.01);
(Continued)

(58) Field of Classification Search
None
See application file for complete search history.

(56) References Cited

U.S. PATENT DOCUMENTS 8,592,385 B2   11/2013   Kataoka et al.
9,254,265 B2 *   2/2016   Geall .................. A61K 9/0019
(Continued)

FOREIGN PATENT DOCUMENTS

DE   102006007433 A1   8/2007
EP   1083232 A1   3/2001
(Continued)

OTHER PUBLICATIONS

Belshe et al., "Live Attenuated versus Inactivated Influenza Vaccine in Infants and Young Children," N Engl J Med 356: 685-96 (2007).*
(Continued)

*Primary Examiner* — Janet L Andres
*Assistant Examiner* — M. Franco Salvoza
(74) *Attorney, Agent, or Firm* — Parker Highlander PLLC

(57) ABSTRACT

The present invention relates to vaccines comprising at least one mRNA encoding at least one antigen for use in the treatment of a disease in newborns and/or infants, preferably exhibiting an age of not more than 2 years, preferably of not more than 1 year, more preferably of not more than 9 months or even 6 months, wherein the treatment comprises vaccination of the newborn or infant and eliciting an immune response in said newborn or infant. The present invention is furthermore directed to kits and kits of parts comprising such a vaccine and/or its components and to methods applying such a vaccine or kit.

15 Claims, 3 Drawing Sheets

Figure 1A:
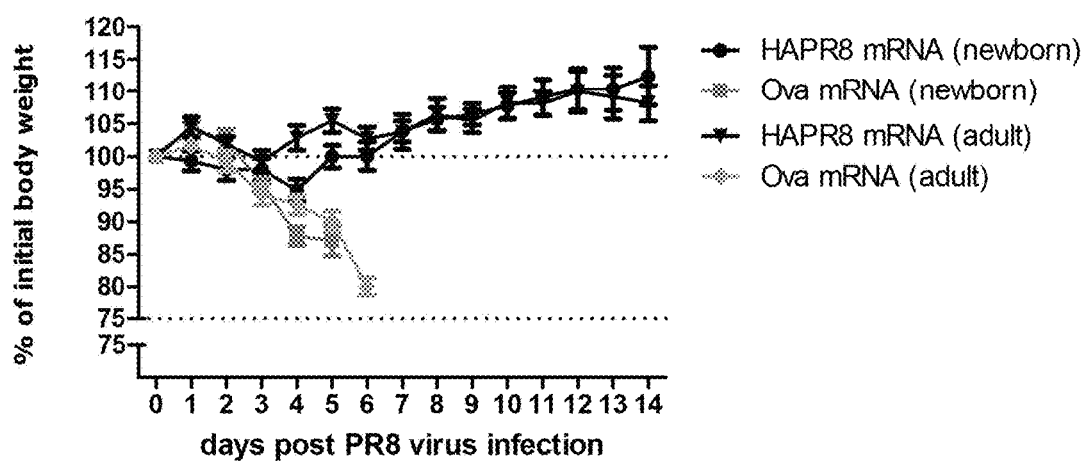

(51) Int. Cl.
- A61K 39/00 (2006.01)
- A61K 47/48 (2006.01)
- A61K 45/06 (2006.01)
- A61K 39/12 (2006.01)

(52) U.S. Cl.
CPC .. *A61K 47/48192* (2013.01); *A61K 47/48323* (2013.01); *A61K 47/48853* (2013.01); *A61K 2039/53* (2013.01); *A61K 2039/55* (2013.01); *A61K 2039/572* (2013.01); *C12N 2760/16134* (2013.01)

(56) References Cited

U.S. PATENT DOCUMENTS

| | | |
|---|---|---|
| 2005/0032730 A1 | 2/2005 | Von Der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2007/0280929 A1 | 12/2007 | Hoerr et al. |
| 2008/0025944 A1 | 1/2008 | Hoerr |
| 2008/0171711 A1 | 7/2008 | Hoerr et al. |
| 2008/0267873 A1 | 10/2008 | Hoerr |
| 2009/0246855 A1* | 10/2009 | Fouchier et al. ............. 435/236 |
| 2009/0324584 A1 | 12/2009 | Hoerr et al. |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof |
| 2011/0250225 A1* | 10/2011 | Fotin-Mleczek .. A61K 39/0011 424/193.1 |
| 2012/0258046 A1 | 10/2012 | Mutzke |

FOREIGN PATENT DOCUMENTS

| | | |
|---|---|---|
| WO | WO98/19710 A2 | 5/1998 |
| WO | WO98/47913 A2 | 10/1998 |
| WO | WO03/059381 A2 | 7/2003 |
| WO | WO03/068942 A2 | 8/2003 |
| WO | WO2006/046978 A2 | 5/2006 |
| WO | WO2007/031319 A1 | 3/2007 |
| WO | WO2007/069068 A2 | 6/2007 |
| WO | WO 2007/099660 | 9/2007 |
| WO | WO 2008/014979 A2 | 2/2008 |
| WO | WO2008/022046 A2 | 2/2008 |
| WO | WO2009/030254 A1 | 3/2009 |
| WO | WO 2009/095226 | 8/2009 |
| WO | WO 2010/037539 | 4/2010 |
| WO | WO2011/026641 A1 | 3/2011 |
| WO | WO 2012/013326 | 2/2012 |
| WO | WO 2012/019780 | 2/2012 |
| WO | WO 2015-024665 | 2/2015 |

OTHER PUBLICATIONS

Pascolo, "Vaccination with Messenger RNA (mRNA)," Toll-Like Receptors (TLRs) and Innate Immunity 183: 221-235 (2008).*

Deering et al., "Nucleic Acid Vaccines: prospects for non-viral delivery of mRNA vaccines," Expert Opin. Drug Deliv. 11(6): 885-899 (2014).*

Fotin-Mleczek et al., "Messenger RNA-based Vaccines With Dual Activity Induce Balanced TLR-7 Dependent Adapting Immune Responses and Provide Antitumor Activity," J Immunotherapy 34:1-15 (2011).*

Bettinger T. et al, Peptide-mediated RNA delivery: a novel approach for enhanced transfection of primary and post-mitotic cells, Nucleic Acids Research, 2001, vol. 29, No. 18, 3882-3891.

Bolhassani Azam et al, Improvement of different vaccine delivery systems for cancer therapy, Molecular Cancer, Biomed Central, London, GB, vol. 10, No. 1, Jan. 7, 2011, p. 3.

Bot A. et al: Enhanced protection against influenza virus of mice immunized as newborns with a mixture of plasmids expressing hemagglutinin and nucleoprotein, Vaccine, Elsevier Ltd., GB, vol. 16, No. 17, Oct. 1, 1998, pp. 1675-1682.

Bot A. et al: Genetic immunization of neonates, Microbes and Infection, Institut Pasteur, Apr. 2002 LNKD-PUBMED:11932202, vol. 4, No. 4, Apr. 2002, pp. 511-520.

Bot A. et al: Induction of humoral and cellular immunity against influenza virus by immunization of newborn mice with a plasmid bearing a hemagglutinin gene, International Immunology, vol. 9, No. 11, Dec. 31, 1997, pp. 1641-1650.

Brito Luis A. et al, Non-viral eNOS gene delivery and transfection with stents for the treatment of restenosis, Biomed Eng Online. Sep. 27, 2010;9:56. doi: 10.1186/1475-925X-9-56.

Burke RS et al., Extracellular barriers to in Vivo PEI and PEGylated PEI Polyplex-Mediated Gene Delivery to the Liver, Bioconjugate Chem. Mar. 2008;19(3):693-704. Epub Feb. 23, 2008.

Carralot J-P. et al: Polarization of immunity induced by direct injection of naked sequence-stabilized mRNA vaccines, CMLS Cellular and Molecular Life Sciences, Birkhauser Verlag, Heidelberg, DE, vo. 61, No. 18, Sep. 1, 2004, pp. 2418-2424.

Casciato et al, Manual of Clinical Oncology 6th edition. 2009. Lippincott Williams & Wilkins: Philadelphia, p. ix.

Danhier F et al, PLGA-based nanoparticles: An overview of biomedical applications, J Control Release. Jul. 20, 2012;161(2):505-22. doi: 10.1016/j.jconrel.2012.01.043. Epub Feb. 4, 2012.

Deshayes S et al., Cell-penetrating peptides: tools for intracellular delivery of therapeutics, Cell Mol Life Sci. Aug. 2005;62(16):1839-49. Review.

Fajac I et al., Histidylated polylysine as a synthetic vector for gene transfer into immortalized cystic fibrosis airway surface and airway gland serous cells, J Gene Med. Sep.-Oct. 2000;2(5):368-78.

Foerg C et al., On the biomedical promise of cell penetrating peptides: limits versus prospects, J Pharm Sci. Jan. 2008;97(1):144-62. Review.

Fotin-Mleczek M et al: Messenger RNA-based vaccines with dual activity induce balanced TLR-7 dependent adaptive immune responses and provide antitumor activity, Journal of Immunotherapy, Raven Press, NY, US, vo. 34, No. 1, Jan. 1, 2011, pp. 1-15.

Fujita T et al, Calcium enhanced delivery of tetraarginine-PEG-lipid-coated DNA/protamine complexes, International Journal of Pharmaceutics, Elsivier BV, NL, vol. 368, No. 1-2, Feb. 23, 2009, pp. 186-192.

Gao X et al., Nonviral gene delivery: what we know and what is next, AAPS J. Mar. 23, 2007;9(1):E92-104. Review.

Garinot et al., PEGylated PLGA-based nanoparticles targeting M cells for oral vaccination, Journal of Controlled Release, Elsevier, Amsterdam, NL, vol. 120, No. 3, Jul. 17, 2007, pp. 195-204.

Giel-Peitraszuk Malgorzata et al.; Database Biosis, DB Acc. No. Prev199800116011; Pub Acta Biochimica Polonica 1997.

Gravekamp et al: Cancer vaccines in old age, Experimental Gerontology, Elsevier Science, Oxford, GB, vo. 42, No. 5, Apr. 14, 2007, pp. 441-450.

Hamidi M et al., Pharmacokinetic consequences of pegylation, Drug Deliv. Nov.-Dec. 2006;13(6):399-409.

Heil et al., Species-specific recognition of single-stranded RNA via Toll-like receptor 7 and 8, Science, vol. 303, pp. 1526-1529, 2004.

Kovarik J. et al: Optimization of vaccine responses in early life: The role of delivery systems and immunomodulators, Immunology and Cell Biology, Jun. 1998 LNKD-PUBMED:96822966, vol. 76, No. 3, Jun. 1998, pp. 222-236.

Kwok KY et al., Formulation of highly soluble poly(ethylene glycol)-peptide DNA condensates, J Pharm Sci. Oct. 1999;88(10):996-1003.

Lochmann D et al.; 2004; Drug delivery of oligonucleotides by peptides; European Journal of Pharmaceutics and Biopharmaceutics; vol. 58, No. 2, pp. 237-251.

Martin ME et al., Peptide-guided gene delivery, AAPS J. Feb. 9, 2007;9(1):E18-29. Review.

(56) References Cited

OTHER PUBLICATIONS

Mattner F et al, Vaccination with Poly-I-Arginine As Immunostimulant for Peptide Vaccines: Induction of Potent and Long-Lasting T-cell Response against Cancer Antigens, Cancer Research 2002, vol. 62, pp. 1477-1480.
Nakamura Y et al., Octaarginine-modified multifunctional envelope-type nano device for siRNA, J Control Release. Jun. 22, 2007;119(3):360-7. Epub Mar. 23, 2007.
Neu M et al., Recent advances in rational gene transfer vector design based on poly(ethylene imine) and its derivatives, J Gene Med. Aug. 2005;7(8):992-1009.
Oupicky D et al., Importance of lateral and steric stabilization of polyelectrolyte gene delivery vectors for extended systemic circulation, Mol Ther. Apr. 2002;5(4):463-72.
Oupický D et al., Laterally stabilized complexes of DNA with linear reducible polycations: strategy for triggered intracellular activation of DNA delivery vectors, J Am Chem Soc. Jan. 9, 2002;124(1):8-9.
Parker AL et al., Enhanced gene transfer activity of peptide-targeted gene-delivery vectors, J Drug Target. Jan. 2005;13(1):39-51.
Pichon C et al., Poly[Lys-(AEDTP)]: A cationic polymer that allows dissociation of pDNA/cationic polymer complexes in a reductive medium and enhances polyfection, Bioconjug Chem. Jan.-Feb. 2002;13(1):76-82.
Pomroy NC et al., Solubilization of hydrophobic peptides by reversible cysteine PEGylation, Biochem Biophys Res Commun. Apr. 17, 1998;245(2):618-21.
Radu D.L. et al: Plasmid expressing the influenza HA gene protects old mice from lethal challenge with influenza virus, Viral Immunology 1999, LNKD-PUBMED: 10532650, vol. 12, No. 3, 1999, pp. 217-226.
Read ML et al., A versatile reducible polycation-based system for efficient delivery of a broad range of nucleic acids, Nucleic Acids Res. May 24, 2005;33(9):e86.
Read ML et al., RNA-based therapeutic strategies for cancer, Expert Opinion on Therapeutic Patents, 2003, vol. 13, No. 5, pp. 627-638.
Read ML et al., Vectors based on reducible polycations facilitate intracellular release of nucleic acids, J Gene Med. Mar. 2003;5(3):232-45.
Sakae M et al., Highly efficient in vivo gene transfection by plasmid/PEI complexes coated by anionic PEG derivatives bearing carboxyl groups and RGD peptide, Biomedicine and Pharmacotherapy, Elsevier, FR, vol. 62, No. 7, Sep. 1, 2008, pp. 448-453.
Scheel B. et al., 2005; Toll-like receptor-dependent activation of several human blood cell types by protamine-condensed mRNA, Eur J Immunol, vol. 35, No. 5, pp. 1557-1566.
Scheel B. et al., Therapeutic anti-tumor immunity triggered by injections of immunostimulating single-stranded RNA; Eur J Immunol, vol. 36, No. 10, pp. 2807-2816.
Shiffman M. L. et al, Protein dissociation from DNA in model systems and chromatin, Nucleic Acids Res. Sep. 1978;5(9):3409-26.
Takae S et al., PEG-detachable polyplex micelles based on disulfide-linked block catiomers as bioresponsive nonviral gene vectors, J Am Chem Soc. May 7, 2008;130(18):6001-9. Epub Apr. 9, 2008.
Tönges L et al., Stearylated octaarginine and artificial virus-like particles for transfection of siRNA into primary rat neurons, RNA. Jul. 2006;12(7):1431-8. Epub May 12, 2006.
Unnamalai N et al., Cationic oligopeptide-mediated delivery of dsRNA for post-transcriptional gene silencing in plant cells, FEBS Lett. May 21, 2004;566(1-3):307-10.
Vivès E et al., A truncated HIV-1 Tat protein basic domain rapidly translocates through the plasma membrane and accumulates in the cell nucleus, J Biol Chem. Jun. 20, 1997;272(25):16010-7.
Wang YH et al., An intracellular delivery method for siRNA by an arginine-rich peptide, J Biochem Biophys Methods. Jun. 10, 2007;70(4):579-86. Epub Jan. 30, 2007.
Zhang Z. et al., Delivery of Telomerase Reverse Transcriptase Small Interfering RNA in Complex with Positively Charged Single-Walled Carbon Nanotubese Suppresses Tumor Growth, Clinical Cancer Research 2006, 12: 4933-4939.
Zohra F. T. et al, Effective delivery with enhanced translational activity synergistically accelerates mRNA-based transfection, Biochem Biophys Res Commun. Jun. 22, 2007;358(1):373-8. Epub May 1, 2007.
Yoshitomi et al., "Design of core—shell-type nanoparticles carrying stable radicals in the core", *Biomacromolecules*, 10:596-601, 2009.
Demirjian and Levy, "Safety and efficacy of neonatal vaccination," *Eur J Immunol.*, 39(1):36-46, 2009.
Gervassi and Horton, "Is infant immunity actively suppressed or immature?" *Virology: Research and Treatment*, 5:1-9, 2014.
Petsch et al., "Protective efficacy of in vitro synthesized, specific mRNA vaccines against influenza A virus infection," *Nature Biotechnology*, 30(12):1210-1216, 2012.
Wilschut, "Influenza vaccines: the virosome concept," *Immunology Letters*, 122:118-121, 2009.
Arulanandam et al., "IL-12 is a potent neonatal vaccine adjuvant," *Eur. J. Immunol.*, 29:256-264, 1999.
Arulanandam et al., "Neonatal administration of IL-12 enhances the protective efficacy of antiviral vaccines," *The Journal of Immunology*, 164:3698-3704, 2000.
Hemmi et al., "A toll-like receptor recognizes bacterial DNA," *Nature*, 408(6813):740-745, 2000.
Krieg et al., "The role of CpG dinucleotides in DNA vaccines," *Trends in Microbiology*, 6(1):23-27, 1998.
Sarzotti et al., "Induction of protective CTL responses in newborn mice by a murine retrovirus," *Science*, 271(5256):1726-1728, 1996.
Thompson and Locarnini, "Toll-like receptors, RIG-I-like RNA helicases and the antiviral innate immune response," *Immunology and Cell Biology*, 85(6):435-445, 2007.
Antohi et al., "The reactivity pattern of hemagglutinin-specific clonotypes from mice immunized as neonates or adults with naked DNA," *International Immunology*, 10(4):663-668, 1998.
Bot et al., "Protective cellular immunity against influenza virus induced by plasmid inoculation of newborn mice," *Developmental Immunology*, 5:197-210, 1998.
Yoshitomi et al., "Desgin of core—shell-type nanoparticles carrying stable radicals in the core", *Biomacromolecules*, 10:596-601, 2009.

\* cited by examiner

PR8 H1 mRNA

AUGAAGGCCAACCUGCUCGUGCUGCUGUGCGCCCUCGCGGCCGCCGACGCCGA
CACCAUCUGCAUCGGCUACCACGCCAACAACAGCACCGACACGGUCGACACCG
UGCUGGAGAAGAACGUGACCGUCACCCACUCCGUGAACCUGCUCGAGGACAGC
CACAACGGGAAGCUGUGCCGGCUGAAGGGCAUCGCGCCCUCCAGCUGGGGAA
GUGCAACAUCGCCGGCUGGCUGCUCGGGAACCCGGAGUGCGACCCCUGCUGC
CCGUGCGCUCCUGGAGCUACAUCGUCGAGACGCCCAACUCCGAGAACGGCAUC
UGCUACCCGGGCGACUUCAUCGACUACGAGGAGCUCCGGGAGCAGCUGAGCUC
CGUGAGCUCCUUCGAGCGCUUCGAGAUCUUCCCCAAGGAGAGCUCCUGGCCCA
ACCACAACACCAACGGGGUGACCGCCGCCUGCAGCCACGAGGGCAAGUCCAGC
UUCUACCGGAACCUGCUCUGGCUGACCGAGAAGGAGGGGUCCUACCCCAAGCU
GAAGAACAGCUACGUCAACAAGAAGGGCAAGGAGGUGCUCGUGCUGUGGGGA
UCCACCACCCGCCCAACUCCAAGGAGCAGCAGAACCUGUACCAGAACGAGAAC
GCGUACGUCAGCGUGGUGACGUCCAACUACAACGCCGGUUCACCCCCGAGAU
CGCCGAGCGCCCCAAGGUCCGGGACCAGGCCGGCCGCAUGAACUACUACUGGA
CCCUCCUGAAGCCGGGCGACACCAUCAUCUUCGAGGCCAACGGGAACCUGAUC
GCCCCGAUGUACGCGUUCGCCCUCAGCCGGGGCUUCGGGAGCGGCAUCAUCAC
GUCCAACGCCAGCAUGCACGAGUGCAACACCAAGUGCCAGACCCCCUGGGCG
CCAUCAACUCCAGCCUGCCCUACCAGAACAUCCACCCGGUGACCAUCGGGGAG
UGCCCCAAGUACGUGCGCUCCGCCAAGCUCCGGAUGGUCACGGGCCUGCGCAA
CAACCCCAGCAUCCAGUCCCGGGGGCUGUUCGGCGCGAUCGCCGGGUUCAUCG
AGGGCGGCUGGACCGGGAUGAUCGACGGCUGGUACGGGUACCACCACCAGAAC
GAGCAGGGCAGCGGGUACGCCGCCGACCAGAAGUCCACCCAGAACGCCAUCAA
CGGCAUCACCAACAAGGUGAACACGGUGAUCGAGAAGAUGAACAUCCAGUUCA
CCGCGGUCGGCAAGGAGUUCAACAAGCUCGAGAAGCGCAUGGAGAACCUGAAC
AAGAAGGUGGACGACGGGUUCCUGGACAUCUGGACCUACAACGCCGAGCUCCU
GGUGCUGCUCGAGAACGAGCGGACCCUGGACUUCCACGACAGCAACGUCAAGA
ACCUGUACGAGAAGGUGAAGUCCCAGCUCAAGAACAACGCCAAGGAGAUCGGC
AACGGGUGCUUCGAGUUCUACCACAAGUGCGACAACGAGUGCAUGGAGAGCGU
CCGCAACGGCACGUACGACUACCCCAAGUACUCCGAGGAGAGCAAGCUGAACC
GGGAGAAGGUGGACGGGGUGAAGCUGGAGUCCAUGGGCAUCUACCAGAUCCUC
GCCAUCUACAGCACCGUCGCCUCCAGCCUGGUGCUGCUGGUGUCCCUCGGCGC
GAUCAGCUUCUGGAUGUGCAGCAACGGGUCCCUGCAGUGCCGCAUCUGCAUCU
GA

Elements in 3:UTR of mRNAs: alpha goblin 3:UTR, poly A, poly C
Vector used: pCV19

Figure 1B

Ovalbumin (control) mRNA
AUGGGCAGCAUCGGGGCCGCGUCGAUGGAGUUCUGCUUCGACGUGUUCAAGGA
GCUGAAGGUCCACCACGCCAACGAGAACAUCUUCUACUGCCCGAUCGCCAUCA
UGAGCGCGCUCGCCAUGGUGUACCUGGGCGCCAAGGACAGCACCCGGACGCAG
AUCAACAAGGUGGUCCGCUUCGACAAGCUGCCCGGCUUCGGGGACUCGAUCGA
GGCGCAGUGCGGCACCAGCGUGAACGUGCACAGCUCGCUCCGGGACAUCCUGA
ACCAGAUCACCAAGCCGAACGACGUCUACAGCUUCAGCCUGGCCUCGCGGCUC
UACGCCGAGGAGCGCUACCCGAUCCUGCCCGAGUACCUGCAGUGCGUGAAGGA
GCUCUACGGGGCGGGCUGGAGCCGAUCAACUUCCAGACGGCGGCCGACCAGG
CCCGGGAGCUGAUCAACAGCUGGGUGGAGAGCCAGACCAACGGCAUCAUCCGC
AACGUCCUCCAGCCGUCGAGCGUGGACAGCCAGACCGCGAUGGUGCUGGUCAA
CGCCAUCGUGUUCAAGGGCCUGUGGGAGAAGACGUUCAAGGACGAGGACACCC
AGGCCAUGCCCUUCCGGGUGACCGAGCAGGAGUCGAAGCCGGUCCAGAUGAUG
UACCAGAUCGGGCUCUUCCGGGUGGCGAGCAUGGCCAGCGAGAAGAUGAAGAU
CCUGGAGCUGCCGUUCGCCUCGGGCACGAUGAGCAUGCUCGUGCUGCUGCCCG
ACGAGGUCAGCGGCCUCGAGCAGCUGGAGUCGAUCAUCAACUUCGAGAAGCUG
ACCGAGUGGACCAGCAGCAACGUGAUGGAGGAGCGCAAGAUCAAGGUGUACCU
CCCGCGGAUGAAGAUGGAGGAGAAGUACAACCUGACGUCGGUCCUGAUGGCGA
UGGGGAUCACCGACGUGUUCAGCAGCUCGGCCAACCUCAGCGGCAUCAGCUCG
GCCGAGAGCCUGAAGAUCAGCCAGGCGGUGCACGCCGCCCACGCGGAGAUCAA
CGAGGCCGGCCGGGAGGUCGUGGGGUCGGCCGAGGCGGGCGUGGACGCCGCCA
GCGUCAGCGAGGAGUUCCGCGCGGACCACCCGUUCCUGUUCUGCAUCAAGCAC
AUCGCCACCAACGCCGUGCUCUUCUUCGGCCGGUGCGUGUCGCCCUGA Elements in 3'UTR of mRNAs: alpha goblin 3'UTR, poly A, poly C
Vector used: pCV19

Figure 1C

SEQUENCE LISTING

<160> NUMBER OF SEQ ID NOS: 385

<210> SEQ ID NO 1
<211> LENGTH: 9
<212> TYPE: PRT
<213> ORGANISM: Artificial Sequence

```
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 1

Cys Arg Arg Arg Arg Arg Arg Cys
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 2

Cys Arg Arg Arg Arg Arg Arg Arg Arg Cys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 3

Cys Arg Arg Arg Arg Arg Arg Arg Arg Arg Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 4

Cys Arg Arg Arg Arg Arg Arg Arg Arg Arg Arg Cys
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 5

Cys Arg Arg Arg Arg Arg Arg Arg Arg Arg Arg Arg Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys
```

```
<400> SEQUENCE: 6

Cys Arg Arg Arg Arg Arg Arg Arg Arg Arg Arg Arg Cys
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 7

Cys Arg Arg Arg Arg Arg Arg Arg Arg Arg Arg Arg Arg Cys
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 8

Cys Arg Arg Arg Arg Arg Arg Arg Arg Arg Arg Arg Arg Arg Cys
1               5                   10                  15

<210> SEQ ID NO 9
<211> LENGTH: 17
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 9

Cys Arg Arg Arg Arg Arg Arg Arg Arg Arg Arg Arg Arg Arg Arg
1               5                   10                  15

Cys

<210> SEQ ID NO 10
<211> LENGTH: 18
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 10

Cys Arg Arg Arg Arg Arg Arg Arg Arg Arg Arg Arg Arg Arg Arg
1               5                   10                  15

Arg Cys

<210> SEQ ID NO 11
<211> LENGTH: 19
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys
```

```
<400> SEQUENCE: 11

Cys Arg Arg Arg Arg Arg Arg Arg Arg Arg Arg Arg Arg Arg
1               5                   10                  15

Arg Arg Cys

<210> SEQ ID NO 12
<211> LENGTH: 20
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 12

Cys Arg Arg Arg Arg Arg Arg Arg Arg Arg Arg Arg Arg Arg Arg
1               5                   10                  15

Arg Arg Arg Cys
            20

<210> SEQ ID NO 13
<211> LENGTH: 21
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 13

Cys Arg Arg Arg Arg Arg Arg Arg Arg Arg Arg Arg Arg Arg Arg
1               5                   10                  15

Arg Arg Arg Arg Cys
            20

<210> SEQ ID NO 14
<211> LENGTH: 22
<212> TYPE: PRT
<213> ORGANISM: Artificial Sequence
<220> FEATURE:
<223> OTHER INFORMATION: Description of Sequence: cationic or
      polycationic peptide of formula (Ib):
      Cys {(Arg)l;(Lys)m;(His)n;(Orn)o;(Xaa)x} Cys

<400> SEQUENCE: 14

Cys Arg Arg Arg Arg Arg Arg Arg Arg Arg Arg Arg Arg Arg Arg
1               5                   10                  15

Arg Arg Arg Arg Arg Cys
            20

<210> SEQ ID NO 15

<400> SEQUENCE: 15

000

<210> SEQ ID NO 16

<400> SEQUENCE: 16

000

<210> SEQ ID NO 17

<400> SEQUENCE: 17
```

000

<210> SEQ ID NO 18
<400> SEQUENCE: 18

000

<210> SEQ ID NO 19
<400> SEQUENCE: 19

000

<210> SEQ ID NO 20
<400> SEQUENCE: 20

000

<210> SEQ ID NO 21
<400> SEQUENCE: 21

000

<210> SEQ ID NO 22
<400> SEQUENCE: 22

000

<210> SEQ ID NO 23
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 23

Trp Tyr Trp Tyr
1

<210> SEQ ID NO 24
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 24

Tyr Trp Tyr Trp
1

<210> SEQ ID NO 25
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 25

Trp Trp Trp Trp
1

<210> SEQ ID NO 26

```
<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 32

Phe Tyr Phe Tyr
1

<210> SEQ ID NO 33
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 33

Tyr Phe Tyr Phe
1

<210> SEQ ID NO 34
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 34

Phe Phe Phe Phe
1
```

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 40

Phe Trp Phe Trp
1

<210> SEQ ID NO 41
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 41

Trp Phe Trp Phe
1

<210> SEQ ID NO 42
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 42

Tyr Tyr Tyr Tyr
1

<210> SEQ ID NO 43

<400> SEQUENCE: 43

```
000

<210> SEQ ID NO 44

<400> SEQUENCE: 44

000

<210> SEQ ID NO 45
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 45

Cys Trp Tyr Cys
1

<210> SEQ ID NO 46
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 46

Cys Tyr Trp Cys
1

<210> SEQ ID NO 47
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 47

Cys Trp Trp Cys
1

<210> SEQ ID NO 48
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 48

Cys Tyr Tyr Cys
1

<210> SEQ ID NO 49
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 49

Cys Trp Tyr Trp Cys
1               5

<210> SEQ ID NO 50
<211> LENGTH: 5
<212> TYPE: PRT
<213> ORGANISM: Artificial Sequence
```

```
<220> FEATURE:
<223> OTHER INFORMATION: Exemplary aromatic amino acid component (AA)

<400> SEQUENCE: 50

Cys Tyr Trp Tyr Cys
1               5

<210> SEQ ID NO 51
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 51

Cys Trp Trp Trp Cys
1               5

<210> SEQ ID NO 52
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 52

Cys Tyr Tyr Tyr Cys
1               5

<210> SEQ ID NO 53
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 53

Cys Trp Tyr Trp Tyr Cys
1               5

<210> SEQ ID NO 54
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 54

Cys Tyr Trp Tyr Trp Cys
1               5

<210> SEQ ID NO 55
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 55

Cys Trp Trp Trp Trp Cys
1               5

<210> SEQ ID NO 56
<211> LENGTH: 6
<212> TYPE: PRT
<213> ORGANISM: Artificial Sequence
<220> FEATURE:
```

<223> OTHER INFORMATION: Exemplary aromatic amino acid component (AA)

<400> SEQUENCE: 56

Cys Tyr Tyr Tyr Tyr Cys
1               5

<210> SEQ ID NO 57

<400> SEQUENCE: 57

000

<210> SEQ ID NO 58
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 58

Cys Phe Tyr Cys
1

<210> SEQ ID NO 59
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 59

Cys Tyr Phe Cys
1

<210> SEQ ID NO 60
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 60

Cys Phe Phe Cys
1

<210> SEQ ID NO 61
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 61

Cys Tyr Tyr Cys
1

<210> SEQ ID NO 62
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 62

Cys Phe Tyr Phe Cys
1               5

```
<210> SEQ ID NO 63
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 63

Cys Tyr Phe Tyr Cys
1               5

<210> SEQ ID NO 64
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 64

Cys Phe Phe Phe Cys
1               5

<210> SEQ ID NO 65
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 65

Cys Tyr Tyr Tyr Cys
1               5

<210> SEQ ID NO 66
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 66

Cys Phe Tyr Phe Tyr Cys
1               5

<210> SEQ ID NO 67
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 67

Cys Tyr Phe Tyr Phe
1               5

<210> SEQ ID NO 68
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 68

Cys Phe Phe Phe Phe Cys
1               5
```

-continued

```
<210> SEQ ID NO 69
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 69

Cys Phe Trp Cys
1

<210> SEQ ID NO 70
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 70

Cys Trp Phe Cys
1

<210> SEQ ID NO 71
<211> LENGTH: 4
<212> TYPE: PRT
<213> ORGANISM: Artificial Sequence
<220> FEATURE:
<223> OTHER INFORMATION: Exemplary aromatic amino acid component (AA)

<400> SEQUENCE: 71

Cys Phe Phe Cys
1

<210> SEQ ID NO 72
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 72

Cys Phe Trp Phe Cys
1               5

<210> SEQ ID NO 73
<211> LENGTH: 5
<212> TYPE: PRT
<213> ORGANISM: Artificial Sequence
<220> FEATURE:
<223> OTHER INFORMATION: Exemplary aromatic amino acid component (AA)

<400> SEQUENCE: 73

Cys Trp Phe Trp Cys
1               5

<210> SEQ ID NO 74
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 74

Cys Phe Trp Phe Trp Cys
1               5

<210> SEQ ID NO 75
```

```
<211> LENGTH: 6
<212> TYPE: PRT
<213> ORGANISM: Artificial Sequence
<220> FEATURE:
<223> OTHER INFORMATION: Exemplary aromatic amino acid component (AA)

<400> SEQUENCE: 75

Cys Trp Phe Trp Phe Cys
1               5

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 84

Ser Thr Ser Thr
```

```
<210> SEQ ID NO 85
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 85

Thr Ser Thr Ser
1

<210> SEQ ID NO 86
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 86

Ser Ser Ser Ser
1

<210> SEQ ID NO 87
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 87

Thr Thr Thr Thr
1

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000
```

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 96

Gln Asn Gln Asn
1

<210> SEQ ID NO 97
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 97

Asn Gln Asn Gln
1

<210> SEQ ID NO 98
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 98

Gln Gln Gln Gln
1

<210> SEQ ID NO 99
<211> LENGTH: 4
<212> TYPE: PRT
<213> ORGANISM: Artificial Sequence
<220> FEATURE:
<223> OTHER INFORMATION: Exemplary hydrophilic (and preferably non charged polar) amino acid component (AA)

<400> SEQUENCE: 99

Asn Asn Asn Asn
1

<210> SEQ ID NO 100

```
<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 108

Ser Asn Ser Asn
1

<210> SEQ ID NO 109
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 109
```

Asn Ser Asn Ser
1

<210> SEQ ID NO 110
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 110

Ser Ser Ser Ser
1

<210> SEQ ID NO 111
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 111

Asn Asn Asn Asn
1

<210> SEQ ID NO 112

<400> SEQUENCE: 112

000

<210> SEQ ID NO 113

<400> SEQUENCE: 113

000

<210> SEQ ID NO 114
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 114

Cys Ser Thr Cys
1

<210> SEQ ID NO 115
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 115

Cys Thr Ser Cys
1

<210> SEQ ID NO 116
<211> LENGTH: 4
<212> TYPE: PRT
<213> ORGANISM: Artificial Sequence
<220> FEATURE:

```
<223> OTHER INFORMATION: Exemplary hydrophilic (and preferably non
      charged polar) amino acid component (AA)

<400> SEQUENCE: 116

Cys Ser Ser Cys
1

<210> SEQ ID NO 117
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 117

Cys Thr Thr Cys
1

<210> SEQ ID NO 118
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 118

Cys Ser Thr Ser Cys
1               5

<210> SEQ ID NO 119
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 119

Cys Thr Ser Thr Cys
1               5

<210> SEQ ID NO 120
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 120

Cys Ser Ser Ser Cys
1               5

<210> SEQ ID NO 121
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 121

Cys Thr Thr Thr Cys
1               5
```

```
<210> SEQ ID NO 122
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 122

Cys Ser Thr Ser Thr Cys
1               5

<210> SEQ ID NO 123
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 123

Cys Thr Ser Thr Ser Cys
1               5

<210> SEQ ID NO 124
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 124

Cys Ser Ser Ser Ser Cys
1               5

<210> SEQ ID NO 125
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 125

Cys Thr Thr Thr Thr Cys
1               5

<210> SEQ ID NO 126

<400> SEQUENCE: 126

000

<210> SEQ ID NO 127

<400> SEQUENCE: 127

000

<210> SEQ ID NO 128
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 128
```

```
Cys Gln Asn Cys
1

<210> SEQ ID NO 129
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 129

Cys Asn Gln Cys
1

<210> SEQ ID NO 130
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 130

Cys Gln Gln Cys
1

<210> SEQ ID NO 131
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 131

Cys Asn Asn Cys
1

<210> SEQ ID NO 132
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 132

Cys Gln Asn Gln Cys
1               5

<210> SEQ ID NO 133
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 133

Cys Asn Gln Asn Cys
1               5

<210> SEQ ID NO 134
<211> LENGTH: 5
<212> TYPE: PRT
<213> ORGANISM: Artificial Sequence
```

```
<220> FEATURE:
<223> OTHER INFORMATION: Exemplary hydrophilic (and preferably non
      charged polar) amino acid component (AA)

<400> SEQUENCE: 134

Cys Gln Gln Gln Cys
1               5

<210> SEQ ID NO 135
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 135

Cys Asn Asn Asn Cys
1               5

<210> SEQ ID NO 136
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 136

Cys Gln Asn Gln Asn Cys
1               5

<210> SEQ ID NO 137
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 137

Cys Asn Gln Asn Gln Cys
1               5

<210> SEQ ID NO 138
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 138

Cys Gln Gln Gln Gln Cys
1               5

<210> SEQ ID NO 139
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 139

Cys Asn Asn Asn Asn Cys
1               5
```

-continued

<210> SEQ ID NO 140

<400> SEQUENCE: 140

000

<210> SEQ ID NO 141

<400> SEQUENCE: 141

000

<210> SEQ ID NO 142
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 142

Cys Ser Asn Cys
1

<210> SEQ ID NO 143
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 143

Cys Asn Ser Cys
1

<210> SEQ ID NO 144
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 144

Cys Ser Ser Cys
1

<210> SEQ ID NO 145
<211> LENGTH: 4
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 145

Cys Asn Asn Cys
1

<210> SEQ ID NO 146
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

```
<400> SEQUENCE: 146

Cys Ser Asn Ser Cys
1               5

<210> SEQ ID NO 147
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 147

Cys Asn Ser Asn Cys
1               5

<210> SEQ ID NO 148
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 148

Cys Ser Ser Ser Cys
1               5

<210> SEQ ID NO 149
<211> LENGTH: 5
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 149

Cys Asn Asn Asn Cys
1               5

<210> SEQ ID NO 150
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 150

Cys Ser Asn Ser Asn Cys
1               5

<210> SEQ ID NO 151
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 151

Cys Asn Ser Asn Ser Cys
1               5

<210> SEQ ID NO 152
<211> LENGTH: 6
<212> TYPE: PRT
```

<213> ORGANISM: Artificial Sequence
<220> FEATURE:
<223> OTHER INFORMATION: Exemplary hydrophilic (and preferably non
      charged polar) amino acid component (AA)

<400> SEQUENCE: 152

Cys Ser Ser Ser Ser Cys
1               5

<210> SEQ ID NO 153
<211> LENGTH: 6
<212> TYPE: PRT
<213> ORGANISM: Artificial Sequence
<220> FEATURE:
<223> OTHER INFORMATION: Exemplary hydrophilic (and preferably non
      charged polar) amino acid component (AA)

<400> SEQUENCE: 153

Cys Asn Asn Asn Asn Cys
1               5

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

```
<210> SEQ ID NO 162
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 162

Leu Val Leu Val
1

<210> SEQ ID NO 163
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 163

Val Leu Val Leu
1

<210> SEQ ID NO 164
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 164

Leu Leu Leu Leu
1

<210> SEQ ID NO 165
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 165

Val Val Val Val
1

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169
```

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 175

Ala Ile Ala Ile
1

<210> SEQ ID NO 176
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 176

Ile Ile Ile Ile
1

<210> SEQ ID NO 177
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 177

Ala Ala Ala Ala
1

<210> SEQ ID NO 178

```
<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 186

Met Ala Met Ala
1

<210> SEQ ID NO 187
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 187

Ala Met Ala Met
1
```

```
<210> SEQ ID NO 188
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 188

Met Met Met Met
1

<210> SEQ ID NO 189

<400> SEQUENCE: 189

000

<210> SEQ ID NO 190

<400> SEQUENCE: 190

000

<210> SEQ ID NO 191
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 191

Cys Leu Val Cys
1

<210> SEQ ID NO 192
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 192

Cys Val Leu Cys
1

<210> SEQ ID NO 193
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 193

Cys Leu Leu Cys
1

<210> SEQ ID NO 194
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 194

Cys Val Val Cys
1
```

```
<210> SEQ ID NO 195
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 195

Cys Leu Val Leu Cys
1               5

<210> SEQ ID NO 196
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 196

Cys Val Leu Val Cys
1               5

<210> SEQ ID NO 197
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 197

Cys Leu Leu Leu Cys
1               5

<210> SEQ ID NO 198
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 198

Cys Val Val Val Cys
1               5

<210> SEQ ID NO 199
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 199

Cys Leu Val Leu Val Cys
1               5

<210> SEQ ID NO 200
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 200

Cys Val Leu Val Leu Cys
1               5
```

```
<210> SEQ ID NO 201
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 201

Cys Leu Leu Leu Leu Cys
1               5

<210> SEQ ID NO 202
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 202

Cys Val Val Val Val Cys
1               5

<210> SEQ ID NO 203

<400> SEQUENCE: 203

000

<210> SEQ ID NO 204

<400> SEQUENCE: 204

000

<210> SEQ ID NO 205
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 205

Cys Ile Ala Cys
1

<210> SEQ ID NO 206
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 206

Cys Ala Ile Cys
1

<210> SEQ ID NO 207
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 207

Cys Ile Ile Cys
1
```

```
<210> SEQ ID NO 208
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 208

Cys Ala Ala Cys
1

<210> SEQ ID NO 209
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 209

Cys Ile Ala Ile Cys
1               5

<210> SEQ ID NO 210
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 210

Cys Ala Ile Ala Cys
1               5

<210> SEQ ID NO 211
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 211

Cys Ile Ile Ile Cys
1               5

<210> SEQ ID NO 212
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 212

Cys Ala Ala Ala Cys
1               5

<210> SEQ ID NO 213
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 213

Cys Ile Ala Ile Ala Cys
1               5

<210> SEQ ID NO 214
```

```
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 214

Cys Ala Ile Ala Ile Cys
1               5

<210> SEQ ID NO 215
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 215

Cys Ile Ile Ile Ile Cys
1               5

<210> SEQ ID NO 216
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 216

Cys Ala Ala Ala Ala Cys
1               5

<210> SEQ ID NO 217

<400> SEQUENCE: 217

000

<210> SEQ ID NO 218
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 218

Cys Met Ala Cys
1

<210> SEQ ID NO 219
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 219

Cys Ala Met Cys
1

<210> SEQ ID NO 220
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 220
```

```
Cys Met Met Cys
1

<210> SEQ ID NO 221
<211> LENGTH: 4
<212> TYPE: PRT
<213> ORGANISM: Artificial Sequence
<220> FEATURE:
<223> OTHER INFORMATION: Exemplary lipophilic amino acid component (AA)

<400> SEQUENCE: 221

Cys Ala Ala Cys
1

<210> SEQ ID NO 222
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 222

Cys Met Ala Met Cys
1               5

<210> SEQ ID NO 223
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 223

Cys Ala Met Ala Cys
1               5

<210> SEQ ID NO 224
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 224

Cys Met Met Met Cys
1               5

<210> SEQ ID NO 225
<211> LENGTH: 5
<212> TYPE: PRT
<213> ORGANISM: Artificial Sequence
<220> FEATURE:
<223> OTHER INFORMATION: Exemplary lipophilic amino acid component (AA)

<400> SEQUENCE: 225

Cys Ala Ala Ala Cys
1               5

<210> SEQ ID NO 226
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 226
```

```
Cys Met Ala Met Ala Cys
1               5

<210> SEQ ID NO 227
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 227

Cys Ala Met Ala Met Cys
1               5

<210> SEQ ID NO 228
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 228

Cys Met Met Met Met Cys
1               5

<210> SEQ ID NO 229
<211> LENGTH: 6
<212> TYPE: PRT
<213> ORGANISM: Artificial Sequence
<220> FEATURE:
<223> OTHER INFORMATION: Exemplary lipophilic amino acid component (AA)

<400> SEQUENCE: 229

Cys Ala Ala Ala Ala Cys
1               5

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235
```

```
<400> SEQUENCE: 235

000

<210> SEQ ID NO 236

<400> SEQUENCE: 236

000

<210> SEQ ID NO 237

<400> SEQUENCE: 237

000

<210> SEQ ID NO 238
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 238

Asp His Asp His
1

<210> SEQ ID NO 239
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 239

His Asp His Asp
1

<210> SEQ ID NO 240
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 240

Asp Asp Asp Asp
1

<210> SEQ ID NO 241
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 241

His His His His
1

<210> SEQ ID NO 242

<400> SEQUENCE: 242

000
```

```
<210> SEQ ID NO 243

<400> SEQUENCE: 243

000

<210> SEQ ID NO 244
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 244

Cys Asp His Cys
1

<210> SEQ ID NO 245
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 245

Cys His Asp Cys
1

<210> SEQ ID NO 246
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 246

Cys Asp Asp Cys
1

<210> SEQ ID NO 247
<211> LENGTH: 4
<212> TYPE: PRT
<213> ORGANISM: Artificial Sequence
<220> FEATURE:
<223> OTHER INFORMATION: Exemplary weak basic amino acid component (AA)

<400> SEQUENCE: 247

Cys His His Cys
1

<210> SEQ ID NO 248
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 248

Cys Asp His Asp Cys
1               5

<210> SEQ ID NO 249
<211> LENGTH: 5
<212> TYPE: PRT
<213> ORGANISM: Artificial Sequence
<220> FEATURE:
<223> OTHER INFORMATION: Exemplary weak basic amino acid component (AA)
```

```
<400> SEQUENCE: 249

Cys His Asp His Cys
1               5

<210> SEQ ID NO 250
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 250

Cys Asp Asp Asp Cys
1               5

<210> SEQ ID NO 251
<211> LENGTH: 5
<212> TYPE: PRT
<213> ORGANISM: Artificial Sequence
<220> FEATURE:
<223> OTHER INFORMATION: Exemplary weak basic amino acid component (AA)

<400> SEQUENCE: 251

Cys His His His Cys
1               5

<210> SEQ ID NO 252
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 252

Cys Asp His Asp His Cys
1               5

<210> SEQ ID NO 253
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 253

Cys His Asp His Asp Cys
1               5

<210> SEQ ID NO 254
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 254

Cys Asp Asp Asp Asp Cys
1               5

<210> SEQ ID NO 255
<211> LENGTH: 6
<212> TYPE: PRT
<213> ORGANISM: Artificial Sequence
<220> FEATURE:
<223> OTHER INFORMATION: Exemplary weak basic amino acid component (AA)

<400> SEQUENCE: 255
```

```
Cys His His His His Cys
1               5

<210> SEQ ID NO 256
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 256

Lys Asp Glu Leu
1

<210> SEQ ID NO 257
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 257

Asp Asp Glu Leu
1

<210> SEQ ID NO 258
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 258

Asp Glu Glu Leu
1

<210> SEQ ID NO 259
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 259

Gln Glu Asp Leu
1

<210> SEQ ID NO 260
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 260

Arg Asp Glu Leu
1

<210> SEQ ID NO 261
<211> LENGTH: 8
<212> TYPE: PRT
<213> ORGANISM: Artificial Sequence
```

```
<220> FEATURE:
<223> OTHER INFORMATION: Description of sequence: signal peptide,
      localization signal or sequence or nuclear localization signal

<400> SEQUENCE: 261

Gly Gln Asn Leu Ser Thr Ser Asn
1               5

<210> SEQ ID NO 262
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 262

Pro Lys Lys Lys Arg Lys Val
1               5

<210> SEQ ID NO 263
<211> LENGTH: 7
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 263

Pro Gln Lys Lys Ile Lys Ser
1               5

<210> SEQ ID NO 264
<211> LENGTH: 5
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 264

Gln Pro Lys Lys Pro
1               5

<210> SEQ ID NO 265
<211> LENGTH: 4
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 265

Arg Lys Lys Arg
1

<210> SEQ ID NO 266
<211> LENGTH: 12
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 266

Arg Lys Lys Arg Arg Gln Arg Arg Arg Ala His Gln
1               5                   10
```

-continued

<210> SEQ ID NO 267
<211> LENGTH: 16
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 267

Arg Gln Ala Arg Arg Asn Arg Arg Arg Trp Arg Glu Arg Gln Arg
1               5                   10                  15

<210> SEQ ID NO 268
<211> LENGTH: 19
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 268

Met Pro Leu Thr Arg Arg Arg Pro Ala Ala Ser Gln Ala Leu Ala Pro
1               5                   10                  15

Pro Thr Pro

<210> SEQ ID NO 269
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 269

Gly Ala Ala Leu Thr Ile Leu Val
1               5

<210> SEQ ID NO 270
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 270

Gly Ala Ala Leu Thr Leu Leu Gly
1               5

<210> SEQ ID NO 271
<211> LENGTH: 15
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 271

Met Asp Asp Gln Arg Asp Leu Ile Ser Asn Asn Glu Gln Leu Pro
1               5                   10                  15

<210> SEQ ID NO 272
<211> LENGTH: 32
<212> TYPE: PRT
<213> ORGANISM: Artificial Sequence
<220> FEATURE:
<223> OTHER INFORMATION: Description of sequence: signal peptide,

```
                       localization signal or sequence or nuclear localization signal
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 272

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
            20                  25                  30

<210> SEQ ID NO 273
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 273

Gly Cys Val Cys Ser Ser Asn Pro
1               5

<210> SEQ ID NO 274
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 274

Gly Gln Thr Val Thr Thr Pro Leu
1               5

<210> SEQ ID NO 275
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 275

Gly Gln Glu Leu Ser Gln His Glu
1               5

<210> SEQ ID NO 276
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 276

Gly Asn Ser Pro Ser Tyr Asn Pro
1               5

<210> SEQ ID NO 277
<211> LENGTH: 8
<212> TYPE: PRT
<213> ORGANISM: Artificial Sequence
```

```
<220> FEATURE:
<223> OTHER INFORMATION: Description of sequence: signal peptide,
      localization signal or sequence or nuclear localization signal

<400> SEQUENCE: 277

Gly Val Ser Gly Ser Lys Gly Gln
1               5

<210> SEQ ID NO 278
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 278

Gly Gln Thr Ile Thr Thr Pro Leu
1               5

<210> SEQ ID NO 279
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 279

Gly Gln Thr Leu Thr Thr Pro Leu
1               5

<210> SEQ ID NO 280
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 280

Gly Gln Ile Phe Ser Arg Ser Ala
1               5

<210> SEQ ID NO 281
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 281

Gly Gln Ile His Gly Leu Ser Pro
1               5

<210> SEQ ID NO 282
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 282

Gly Ala Arg Ala Ser Val Leu Ser
1               5
```

<210> SEQ ID NO 283
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 283

Gly Cys Thr Leu Ser Ala Glu Glu
1               5

<210> SEQ ID NO 284
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 284

Gly Ala Gln Val Ser Ser Gln Lys
1               5

<210> SEQ ID NO 285
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 285

Gly Ala Gln Leu Ser Arg Asn Thr
1               5

<210> SEQ ID NO 286
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 286

Gly Asn Ala Ala Ala Ala Lys Lys
1               5

<210> SEQ ID NO 287
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 287

Gly Asn Glu Ala Ser Tyr Pro Leu
1               5

<210> SEQ ID NO 288
<211> LENGTH: 8
<212> TYPE: PRT
<213> ORGANISM: Artificial Sequence
<220> FEATURE:
<223> OTHER INFORMATION: Description of sequence: signal peptide,
      localization signal or sequence or nuclear localization signal

<400> SEQUENCE: 288

Gly Ser Ser Lys Ser Lys Pro Lys
1               5

<210> SEQ ID NO 289
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 289
gguuuuuuuu uuuuuuuggg                                          20

<210> SEQ ID NO 290
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 290
ggggguuuuu uuuuuggggg                                          20

<210> SEQ ID NO 291
<211> LENGTH: 40
<212> TYPE: RNA
<213> ORGANISM: Artificial
<220> FEATURE:
<223> OTHER INFORMATION: nucleic acid sequence according to formula (II)

<400> SEQUENCE: 291
ggggguuuuu uuuuuuuuuu uuuuuuuuuu uuuuuggggg                    40

<210> SEQ ID NO 292
<211> LENGTH: 39
<212> TYPE: RNA
<213> ORGANISM: Artificial
<220> FEATURE:
<223> OTHER INFORMATION: nucleic acid sequence according to formula (II)

<400> SEQUENCE: 292
gugugugugu guuuuuuuuu uuuuuuugug ugugugugu                     39

<210> SEQ ID NO 293
<211> LENGTH: 39
<212> TYPE: RNA
<213> ORGANISM: Artificial
<220> FEATURE:
<223> OTHER INFORMATION: nucleic acid sequence according to formula (II)

<400> SEQUENCE: 293
gguugguugg uuuuuuuuuu uuuuuuuggu ugguugguu                     39

<210> SEQ ID NO 294
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 294
gggggggggu uuggggggggg                                         20

<210> SEQ ID NO 295

```
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 295 ggggggggguu uggggggggg                                              20

<210> SEQ ID NO 296
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 296
ggggggguuu uugggggggg                                               20

<210> SEQ ID NO 297
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 297
ggggggguuu uuuggggggg                                               20

<210> SEQ ID NO 298
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 298
gggggguuuu uuugggggggg                                              20

<210> SEQ ID NO 299
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 299
gggggguuuu uuuugggggg                                               20

<210> SEQ ID NO 300
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 300
gggggguuuu uuuuugggg                                                20

<210> SEQ ID NO 301
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 301
```
gggggutuuu uuuuuugggg          20

<210> SEQ ID NO 302
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 302
gggggutuuu uuuuuuuggg          20

<210> SEQ ID NO 303
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 303
ggggutuuuu uuuuuuuggg          20

<210> SEQ ID NO 304
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 304
ggggutuuuu uuuuuuuugg          20

<210> SEQ ID NO 305
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 305
gguuuuuuuu uuuuuuuugg          20

<210> SEQ ID NO 306
<211> LENGTH: 20
<212> TYPE: RNA
<213> ORGANISM: Artificial
<220> FEATURE:
<223> OTHER INFORMATION: nucleic acid sequence according to formula (II)

<400> SEQUENCE: 306
guuuuuuuuu uuuuuuuuug          20

<210> SEQ ID NO 307
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 307
gggggggggg uuuggggggggg gg          22

<210> SEQ ID NO 308
<211> LENGTH: 22
<212> TYPE: RNA

```
<213> ORGANISM: Artificial
<220> FEATURE:
<223> OTHER INFORMATION: nucleic acid sequence according to formula (II)

<400> SEQUENCE: 308 ggggggggggu uugggggggg gg                                              22

<210> SEQ ID NO 309
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 309
gggggggguu uuugggggg gg                                                22

<210> SEQ ID NO 310
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 310
gggggggguu uuuuggggg gg                                                22

<210> SEQ ID NO 311
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 311
ggggggguuu uuuugggggg gg                                               22

<210> SEQ ID NO 312
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 312
ggggggguuu uuuuugggg gg                                                22

<210> SEQ ID NO 313
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 313 gggggguuu uuuuuuggg gg                                                 22

<210> SEQ ID NO 314
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 314
gggggguuuu uuuuuuggg gg                                                22
```

```
<210> SEQ ID NO 315
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 315
gggggguuuu uuuuuuuugg gg                                         22

<210> SEQ ID NO 316
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 316
ggggguuuuu uuuuuuuugg gg                                         22

<210> SEQ ID NO 317
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 317
ggggguuuuu uuuuuuuuug gg                                         22

<210> SEQ ID NO 318
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 318
ggguuuuuuu uuuuuuuuug gg                                         22

<210> SEQ ID NO 319
<211> LENGTH: 22
<212> TYPE: RNA
<213> ORGANISM: Artificial
<220> FEATURE:
<223> OTHER INFORMATION: nucleic acid sequence according to formula (II)

<400> SEQUENCE: 319
gguuuuuuuu uuuuuuuuuu gg                                         22

<210> SEQ ID NO 320
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 320
gggggggggg guuugggggg gggg                                       24

<210> SEQ ID NO 321
<211> LENGTH: 24
<212> TYPE: RNA
<213> ORGANISM: Artificial
<220> FEATURE:
```

```
-continued

<223> OTHER INFORMATION: nucleic acid sequence according to formula (II)

<400> SEQUENCE: 321
gggggggggg uuuugggggg gggg                                              24

<210> SEQ ID NO 322
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 322 ggggggggggu uuuuggggg gggg                                              24

<210> SEQ ID NO 323
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 323 ggggggggggu uuuuuggggg gggg                                             24

<210> SEQ ID NO 324
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 324
gggggggguu uuuuugggg gggg                                               24

<210> SEQ ID NO 325
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 325
gggggggguu uuuuuuggg gggg                                               24

<210> SEQ ID NO 326
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 326
gggggggguu uuuuuuugg gggg                                               24

<210> SEQ ID NO 327
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 327
ggggggguuu uuuuuuugg gggg                                               24
```

-continued

```
<210> SEQ ID NO 328
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 328 gggggggguuu uuuuuuuug gggg                                              24

<210> SEQ ID NO 329
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 329 ggggggguuuu uuuuuuuug gggg                                              24

<210> SEQ ID NO 330
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 330
gggggguuuu uuuuuuuuu gggg                                               24

<210> SEQ ID NO 331
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 331
ggggguuuuu uuuuuuuuu gggg                                               24

<210> SEQ ID NO 332
<211> LENGTH: 24
<212> TYPE: RNA
<213> ORGANISM: Artificial
<220> FEATURE:
<223> OTHER INFORMATION: nucleic acid sequence according to formula (II)

<400> SEQUENCE: 332
gggguuuuuu uuuuuuuuu uggg                                               24

<210> SEQ ID NO 333
<211> LENGTH: 32
<212> TYPE: RNA
<213> ORGANISM: Artificial
<220> FEATURE:
<223> OTHER INFORMATION: nucleic acid sequence according to formula (II)

<400> SEQUENCE: 333
guuuuuuuuu uuuuuuuuuu uuuuuuuuuu ug                                     32

<210> SEQ ID NO 334
<211> LENGTH: 34
<212> TYPE: RNA
<213> ORGANISM: Artificial
<220> FEATURE:
<223> OTHER INFORMATION: nucleic acid sequence according to formula (II)
```

```
<400> SEQUENCE: 334
gguuuuuuuu uuuuuuuuuu uuuuuuuuuu uugg                          34

<210> SEQ ID NO 335
<211> LENGTH: 36
<212> TYPE: RNA
<213> ORGANISM: Artificial
<220> FEATURE:
<223> OTHER INFORMATION: nucleic acid sequence according to formula (II)

<400> SEQUENCE: 335
ggguuuuuuu uuuuuuuuuu uuuuuuuuuu uuuggg                        36

<210> SEQ ID NO 336
<211> LENGTH: 37
<212> TYPE: RNA
<213> ORGANISM: Artificial
<220> FEATURE:
<223> OTHER INFORMATION: nucleic acid sequence according to formula (II)

<400> SEQUENCE: 336
gggguuuuuu uuuuuuuuuu uuuuuuuuuu uuuuggg                       37

<210> SEQ ID NO 337
<211> LENGTH: 39
<212> TYPE: RNA
<213> ORGANISM: Artificial
<220> FEATURE:
<223> OTHER INFORMATION: nucleic acid sequence according to formula (II)

<400> SEQUENCE: 337
ggggguuuuu uuuuuuuuuu uuuuuuuuuu uuuuugggg                     39

<210> SEQ ID NO 338
<211> LENGTH: 41
<212> TYPE: RNA
<213> ORGANISM: Artificial
<220> FEATURE:
<223> OTHER INFORMATION: nucleic acid sequence according to formula (II)

<400> SEQUENCE: 338
gggggguuuu uuuuuuuuuu uuuuuuuuuu uuuuuugggg g                  41

<210> SEQ ID NO 339
<211> LENGTH: 43
<212> TYPE: RNA
<213> ORGANISM: Artificial
<220> FEATURE:
<223> OTHER INFORMATION: nucleic acid sequence according to formula (II)

<400> SEQUENCE: 339
ggggggguuu uuuuuuuuuu uuuuuuuuuu uuuuuuuggg ggg                43

<210> SEQ ID NO 340
<211> LENGTH: 45
<212> TYPE: RNA
<213> ORGANISM: Artificial
<220> FEATURE:
<223> OTHER INFORMATION: nucleic acid sequence according to formula (II)

<400> SEQUENCE: 340
gggggggguu uuuuuuuuuu uuuuuuuuuu uuuuuuuugg ggggg              45

<210> SEQ ID NO 341
<211> LENGTH: 47
```

```
<212> TYPE: RNA
<213> ORGANISM: Artificial
<220> FEATURE:
<223> OTHER INFORMATION: nucleic acid sequence according to formula (II)

<400> SEQUENCE: 341 ggggggggggu uuuuuuuuuu uuuuuuuuuu uuuuuuuug ggggggg                    47

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345
<211> LENGTH: 10
<212> TYPE: RNA
<213> ORGANISM: Artificial
<220> FEATURE:
<223> OTHER INFORMATION: nucleic acid sequence according to formula (II)

<400> SEQUENCE: 345
gguuuuuugg                                                             10

<210> SEQ ID NO 346
<211> LENGTH: 11
<212> TYPE: RNA
<213> ORGANISM: Artificial
<220> FEATURE:
<223> OTHER INFORMATION: nucleic acid sequence according to formula (II)

<400> SEQUENCE: 346
gguuuuuuug g                                                           11

<210> SEQ ID NO 347
<211> LENGTH: 12
<212> TYPE: RNA
<213> ORGANISM: Artificial
<220> FEATURE:
<223> OTHER INFORMATION: nucleic acid sequence according to formula (II)

<400> SEQUENCE: 347
gguuuuuuuu gg                                                          12

<210> SEQ ID NO 348
<211> LENGTH: 13
<212> TYPE: RNA
<213> ORGANISM: Artificial
<220> FEATURE:
<223> OTHER INFORMATION: nucleic acid sequence according to formula (II)

<400> SEQUENCE: 348
gguuuuuuuu ugg                                                         13
```

```
<210> SEQ ID NO 349
<211> LENGTH: 14
<212> TYPE: RNA
<213> ORGANISM: Artificial
<220> FEATURE:
<223> OTHER INFORMATION: nucleic acid sequence according to formula (II)

<400> SEQUENCE: 349 gguuuuuuu uugg                                                        14

<210> SEQ ID NO 350
<211> LENGTH: 15
<212> TYPE: RNA
<213> ORGANISM: Artificial
<220> FEATURE:
<223> OTHER INFORMATION: nucleic acid sequence according to formula (II)

<400> SEQUENCE: 350 gguuuuuuu uuugg                                                       15

<210> SEQ ID NO 351
<211> LENGTH: 16
<212> TYPE: RNA
<213> ORGANISM: Artificial
<220> FEATURE:
<223> OTHER INFORMATION: nucleic acid sequence according to formula (II)

<400> SEQUENCE: 351 gguuuuuuu uuuugg                                                      16

<210> SEQ ID NO 352
<211> LENGTH: 17
<212> TYPE: RNA
<213> ORGANISM: Artificial
<220> FEATURE:
<223> OTHER INFORMATION: nucleic acid sequence according to formula (II)

<400> SEQUENCE: 352 gguuuuuuu uuuuugg                                                     17

<210> SEQ ID NO 353
<211> LENGTH: 18
<212> TYPE: RNA
<213> ORGANISM: Artificial
<220> FEATURE:
<223> OTHER INFORMATION: nucleic acid sequence according to formula (II)

<400> SEQUENCE: 353 gguuuuuuu uuuuuugg                                                    18

<210> SEQ ID NO 354
<211> LENGTH: 19
<212> TYPE: RNA
<213> ORGANISM: Artificial
<220> FEATURE:
<223> OTHER INFORMATION: nucleic acid sequence according to formula (II)

<400> SEQUENCE: 354 gguuuuuuu uuuuuuugg                                                   19

<210> SEQ ID NO 355

<400> SEQUENCE: 355

000
```

```
<210> SEQ ID NO 356
<211> LENGTH: 10
<212> TYPE: RNA
<213> ORGANISM: Artificial
<220> FEATURE:
<223> OTHER INFORMATION: nucleic acid sequence according to formula (II)

<400> SEQUENCE: 356
ggguuuuggg                                                          10

<210> SEQ ID NO 357
<211> LENGTH: 11
<212> TYPE: RNA
<213> ORGANISM: Artificial
<220> FEATURE:
<223> OTHER INFORMATION: nucleic acid sequence according to formula (II)

<400> SEQUENCE: 357
ggguuuuugg g                                                        11

<210> SEQ ID NO 358
<211> LENGTH: 12
<212> TYPE: RNA
<213> ORGANISM: Artificial
<220> FEATURE:
<223> OTHER INFORMATION: nucleic acid sequence according to formula (II)

<400> SEQUENCE: 358
ggguuuuuug gg                                                       12

<210> SEQ ID NO 359
<211> LENGTH: 13
<212> TYPE: RNA
<213> ORGANISM: Artificial
<220> FEATURE:
<223> OTHER INFORMATION: nucleic acid sequence according to formula (II)

<400> SEQUENCE: 359
ggguuuuuuu ggg                                                      13

<210> SEQ ID NO 360
<211> LENGTH: 14
<212> TYPE: RNA
<213> ORGANISM: Artificial
<220> FEATURE:
<223> OTHER INFORMATION: nucleic acid sequence according to formula (II)

<400> SEQUENCE: 360
ggguuuuuuu uggg                                                     14

<210> SEQ ID NO 361
<211> LENGTH: 15
<212> TYPE: RNA
<213> ORGANISM: Artificial
<220> FEATURE:
<223> OTHER INFORMATION: nucleic acid sequence according to formula (II)

<400> SEQUENCE: 361
ggguuuuuuu uuggg                                                    15

<210> SEQ ID NO 362
<211> LENGTH: 16
<212> TYPE: RNA
<213> ORGANISM: Artificial
<220> FEATURE:
<223> OTHER INFORMATION: nucleic acid sequence according to formula (II)
```

```
<400> SEQUENCE: 362
ggguuuuuuu uuuggg                                                          16

<210> SEQ ID NO 363
<211> LENGTH: 17
<212> TYPE: RNA
<213> ORGANISM: Artificial
<220> FEATURE:
<223> OTHER INFORMATION: nucleic acid sequence according to formula (II)

<400> SEQUENCE: 363
ggguuuuuuu uuuuggg                                                         17

<210> SEQ ID NO 364
<211> LENGTH: 18
<212> TYPE: RNA
<213> ORGANISM: Artificial
<220> FEATURE:
<223> OTHER INFORMATION: nucleic acid sequence according to formula (II)

<400> SEQUENCE: 364
ggguuuuuuu uuuuuggg                                                        18

<210> SEQ ID NO 365
<211> LENGTH: 19
<212> TYPE: RNA
<213> ORGANISM: Artificial
<220> FEATURE:
<223> OTHER INFORMATION: nucleic acid sequence according to formula (II)

<400> SEQUENCE: 365
ggguuuuuuu uuuuuuggg                                                       19

<210> SEQ ID NO 366
<211> LENGTH: 57
<212> TYPE: RNA
<213> ORGANISM: Artificial
<220> FEATURE:
<223> OTHER INFORMATION: nucleic acid sequence according to formula (II)

<400> SEQUENCE: 366
ggguuuuuuu uuuuuuugg guuuuuuuuu uuuuugggu uuuuuuuuu uuugggg               57

<210> SEQ ID NO 367
<211> LENGTH: 42
<212> TYPE: RNA
<213> ORGANISM: Artificial
<220> FEATURE:
<223> OTHER INFORMATION: nucleic acid sequence according to formula (II)

<400> SEQUENCE: 367
ggguuuuuuu uuuuuuugg ggggguuuuu uuuuuuuug gg                              42

<210> SEQ ID NO 368
<211> LENGTH: 51
<212> TYPE: RNA
<213> ORGANISM: Artificial
<220> FEATURE:
<223> OTHER INFORMATION: nucleic acid sequence according to formula
      (III)

<400> SEQUENCE: 368
ggguuugggu uugggguugg guuuggguuu ggguuugggu uuggguuugg g                   51

<210> SEQ ID NO 369
```

```
<211> LENGTH: 20
<212> TYPE: RNA
<213> ORGANISM: Artificial Sequence
<220> FEATURE:
<223> OTHER INFORMATION: nucleic acid sequence according to formula
      (II) - Short GU rich

<400> SEQUENCE: 369
gguuuuuuuu uuuuuuuggg                                              20

<210> SEQ ID NO 370
<211> LENGTH: 57
<212> TYPE: RNA
<213> ORGANISM: Artificial
<220> FEATURE:
<223> OTHER INFORMATION: nucleic acid sequence according to formula
      (III)

<400> SEQUENCE: 370 cccuuuuuu uuuuuuucc cuuuuuuuu uuuuucccu uuuuuuuuu uuuccc           57

<210> SEQ ID NO 371
<211> LENGTH: 51
<212> TYPE: RNA
<213> ORGANISM: Artificial
<220> FEATURE:
<223> OTHER INFORMATION: nucleic acid sequence according to formula
      (III)

<400> SEQUENCE: 371
cccuuccccu uucccuuucc cuuucccuuu cccuuucccu uucccuuucc c           51

<210> SEQ ID NO 372
<211> LENGTH: 42
<212> TYPE: RNA
<213> ORGANISM: Artificial
<220> FEATURE:
<223> OTHER INFORMATION: nucleic acid sequence according to formula
      (III)

<400> SEQUENCE: 372
cccuuuuuuu uuuuuuucc ccccuuuuuu uuuuuuuuc cc                       42

<210> SEQ ID NO 373
<211> LENGTH: 60
<212> TYPE: RNA
<213> ORGANISM: Artificial Sequence
<220> FEATURE:
<223> OTHER INFORMATION: nucleic acid sequence according to formula (IV)

<400> SEQUENCE: 373
uagcgaagcu cuuggaccua gguuuuuuuu uuuuuuggg ugcguuccua gaaguacacg   60

<210> SEQ ID NO 374
<211> LENGTH: 120
<212> TYPE: RNA
<213> ORGANISM: Artificial Sequence
<220> FEATURE:
<223> OTHER INFORMATION: nucleic acid sequence according to formula (IV)

<400> SEQUENCE: 374
uagcgaagcu cuuggaccua gguuuuuuuu uuuuuuggg ugcguuccua gaaguacacg   60
aucgcuucga gaaccuggau ccaaaaaaaa aaaaaaccc acgcaaggau cuucaugugc  120

<210> SEQ ID NO 375
<211> LENGTH: 229
```

```
<212> TYPE: RNA
<213> ORGANISM: Artificial Sequence
<220> FEATURE:
<223> OTHER INFORMATION: nucleic acid sequence according to formula (IV)

<400> SEQUENCE: 375
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc auuagauc                229

<210> SEQ ID NO 376
<211> LENGTH: 547
<212> TYPE: RNA
<213> ORGANISM: Artificial Sequence
<220> FEATURE:
<223> OTHER INFORMATION: nucleic acid sequence according to formula (IV)

<400> SEQUENCE: 376
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc auuagaucu cggauuacag   240 cuggaaggag caggaguagu guucuugcuc uaaguaccga gugugcccaa uacccgauca   300
gcuuauuaac gaacggcucc uccucuuaga cugcagcgua agugcggaau cuggggauca   360
aauuacugac ugccuggauu acccucggac auauaaccuu uagcacgcu guugcuguau    420 aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuag                                                            547

<210> SEQ ID NO 377
<211> LENGTH: 1083
<212> TYPE: RNA
<213> ORGANISM: Artificial Sequence
<220> FEATURE:
<223> OTHER INFORMATION: nucleic acid sequence according to formula (IV)

<400> SEQUENCE: 377
gggagaaagc ucaagcuugg agcaaugccc gcacauugag gaaaccgagu ugcauaucuc    60
agaguauugg cccccgugua gguuauucuu gacagacagu ggagcuuauu cacucccagg   120
auccgagucg cauacuacgg uacuggugac agaccuaggu cgucaguuga ccaguccgcc   180
acuagacgug aguccgucaa agcaguuaga uguuacacuc auuagaucu cggauuacag    240 cuggaaggag caggaguagu guucuugcuc uaaguaccga gugugcccaa uacccgauca   300
gcuuauuaac gaacggcucc uccucuuaga cugcagcgua agugcggaau cuggggauca   360
aauuacugac ugccuggauu acccucggac auauaaccuu uagcacgcu guugcuguau    420 aggugaccaa cgcccacucg aguagaccag cucucuuagu ccggacaaug auaggaggcg   480
cggucaaucu acuucuggcu aguuaagaau aggcugcacc gaccucuaua aguagcgugu   540
ccucuagagc uacgcagguu cgcaauaaaa gcguugauua gugugcauag aacagaccuc   600 uuauucgguug aaacgccaga augcuaaauu ccauuaacuc uucccaaaac gcguacggcc   660
gaagacgcgc gcuuaucuug uguacguucu cgcacaugga agaaucagcg ggcauggugg   720
```

| | |
|---|---:|
| uagggcaaua gggagcugg guagcagcga aaaagggccc cugcgcacgu agcuucgcug | 780 |
| uucgucugaa acaacccggc auccguugua gcgaucccgu uaucagugu auucuugugc | 840 |
| gcacuaagau ucauggugua gucgacaaua acagcgucuu ggcagauucu ggucacgugc | 900 |
| ccuaugcccg ggcuugugcc ucucaggugc acagcgauac uuaaagccuu caagguacuc | 960 |
| gacgugggua ccgauucgug acacuuccua agauuauucc acuguuuag ccccgcaccg | 1020 |
| ccgaccuaaa cugguccaau guauacgcau ucgcugagcg gaucgauaau aaaagcuuga | 1080 |
| auu | 1083 |

<210> SEQ ID NO 378
<211> LENGTH: 229
<212> TYPE: RNA
<213> ORGANISM: Artificial Sequence
<220> FEATURE:
<223> OTHER INFORMATION: nucleic acid sequence according to formula (IV)

<400> SEQUENCE: 378

| | |
|---|---:|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagauc | 229 |

<210> SEQ ID NO 379
<211> LENGTH: 546
<212> TYPE: RNA
<213> ORGANISM: Artificial Sequence
<220> FEATURE:
<223> OTHER INFORMATION: nucleic acid sequence according to formula (IV)

<400> SEQUENCE: 379

| | |
|---|---:|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagaucu ucgaccacaa | 240 |
| gugcauauag uagucaucga ggucgccuu uuuuuuuuu uuuuuuuuu uggcccaguu | 300 |
| cugagacuuc gcuagagacu acaguuacag cugcaguagu aaccacgcg gcuauugcag | 360 |
| gaaaucccgu ucagguuuuu uuuuuuuuu uuuuuccgc ucacuaugau uaagaaccag | 420 |
| guggagaguc acugcucucg aggcucacg agagcgcucg auacaguccu uggaagaauc | 480 |
| uuuuuuuuu uuuuuuuuu uugugcgacg aucacagaga acuucuauuc augcaggucu | 540 |
| gcucua | 546 |

<210> SEQ ID NO 380
<211> LENGTH: 1083
<212> TYPE: RNA
<213> ORGANISM: Artificial Sequence
<220> FEATURE:
<223> OTHER INFORMATION: nucleic acid sequence according to formula (IV)

<400> SEQUENCE: 380

| | |
|---|---:|
| gggagaaagc ucaagcuuau ccaaguaggc uggucaccug uacaacguag ccgguauuuu | 60 |
| uuuuuuuuuu uuuuuuuuga ccgucucaag guccaaguua gucugccuau aaaggugcgg | 120 |
| auccacagcu gaugaaagac uugugcggua cgguuaaucu ccccuuuuuu uuuuuuuuu | 180 |
| uuuuuaguaa augcgucuac ugaauccagc gaugaugcug gcccagaucu ucgaccacaa | 240 |

```
gugcauauag uagucaucga ggguCgccuu uuuuuuuuuu uuuuuuuuuu uggcccaguu    300
cugagacuuc gcuagagacu acaguuacag cugcaguagu aaccacugcg gcuauugcag    360
gaaaucccgu ucagguuuuu uuuuuuuuuu uuuuuuccgc ucacuaugau uaagaaccag    420
guggaguguc acugcucucg aggucucacg agagcgcucg auacaguccu uggaagaauc    480
uuuuuuuuuu uuuuuuuuuu uugugcgacg aucacagaga acuucuauuc augcaggucu    540
gcucuagaac gaacugaccu gacgccugaa cuuaugagcg ugcguauuuu uuuuuuuuu    600 uuuuuuuuuc ucccaacaa augucgauca auagcgggc uguuggagac cgucagcaa     660 augccguggc uccauaggac guguagacuu cuauuuuuu uuuuuuuuu uuuuuuu     720 accacaaaua auauucuugc uugguuggc gcaagggccc cguaucaggu cauaaacggg    780 uacauguuc acaggcuccu uuuuuuuuuu uuuuuuuuuu uucgcugagu uauuccgguc    840
ucaaaagacg gcagacguca gucgacaaca cggucuaaag cagugcuaca aucgccgug    900 uucguguuuu uuuuuuuuuu uuuuuuguga accacacgg cgugcacugu aguucgcaau    960
ucauagggua ccggcucaga guuaugccuu gguugaaaac ugcccagcau acuuuuuuu   1020 uuuuuuuuuu uucauauucc caugcuaagc aagggaugcc gcgagucaug uuaagcuga   1080 auu                                                                1083

<210> SEQ ID NO 381
<211> LENGTH: 59
<212> TYPE: RNA
<213> ORGANISM: Artificial Sequence
<220> FEATURE:
<223> OTHER INFORMATION: nucleic acid sequence according to formula (V)

<400> SEQUENCE: 381
uagcgaagcu cuuggaccua ccuuuuuuuu uuuuuucccu gcguuccuag aaguacacg     59

<210> SEQ ID NO 382
<211> LENGTH: 120
<212> TYPE: RNA
<213> ORGANISM: Artificial Sequence
<220> FEATURE:
<223> OTHER INFORMATION: nucleic acid sequence according to formula (V)

<400> SEQUENCE: 382
uagcgaagcu cuuggaccua ccuuuuuuuu uuuuuuuccc ugcguuccua aaguacacg     60 aucgcuucga gaaccuggau ggaaaaaaaa aaaaaagggg acgcaaggau cuucaugugc    120

<210> SEQ ID NO 383
<211> LENGTH: 22
<212> TYPE: RNA
<213> ORGANISM: Artificial
<220> FEATURE:
<223> OTHER INFORMATION: Description of sequence: A synthetic
      stabilizing sequence
<220> FEATURE:
<221> NAME/KEY: misc_feature
<222> LOCATION: (5)..(9)
<223> OTHER INFORMATION: N is A, U, C, or G and is either present or
      absent.
<220> FEATURE:
<221> NAME/KEY: misc_feature
<222> LOCATION: (14)..(17)
<223> OTHER INFORMATION: Y is either present or absent

<400> SEQUENCE: 383
yccannnnnc ccwyyyyucy cc                                             22
```

<210> SEQ ID NO 384
<211> LENGTH: 1698
<212> TYPE: RNA
<213> ORGANISM: Artificial Sequence
<220> FEATURE:
<223> OTHER INFORMATION: PR8 H1 mRNA

<400> SEQUENCE: 384

```
augaaggcca accugcucgu gcugcugugc gcccucgcgg ccgccgacgc cgacaccauc      60
ugcaucggcu accgccaa caacagcacc gacacggucg acaccgugcu ggagaagaac      120
gugaccguca cccacuccgu gaaccugcuc gaggacagcc acaacgggaa gcugugccgg    180
cugaagggca ucgcgcccu ccagcugggg aagugcaaca ucgccggcug gcugcucggg    240
aacccggagu gcgaccccu gcugcccgug cgcuccugga gcuacaucgu cgagacgccc    300
aacuccgaga acggcaucug cuacccgggc gacuucaucg acuacgagga gcuccgggag    360
cagcugagcu ccgugagcuc cuucgagcgc uucgagaucu uccccaagga gagcuccugg    420
cccaaccaca caccaacgg ggugaccgcc gcccugcagcc acgagggcaa guccagcuuc    480
uaccggaacc ugcucuggcu gaccgagaag gaggggucccu accccaagcu gaagaacagc    540
uacgucaaca agaagggcaa ggaggugcuc gugcuguggg ggauccacca cccgcccaac    600
uccaaggagc agcagaaccu guaccagaac gagaacgcgu acgucagcgu ggugacgucc    660
aacuacaacc gccgguucac ccccgagauc gccgagcgcc caaggguccg ggaccaggcc    720
ggccgcauga cuacuacug gacccuccug aagccgggcg acaccaucau cuucgaggcc    780
aacgggaacc ugaucgcccc gauguacgcg uucgcccuca gccgggggcuu cgggagcggc    840
aucaucacgu ccaacgccag caugcacgag ugcaacacca gugccagac ccccugggc     900
gccaucaacu ccagccugcc cuaccagaac auccacccgg ugaccaucgg ggagugcccc    960
aaguacgugc gcuccgccaa gcuccggaug ucacgggcc ugcgcaacaa ccccagcauc   1020
caguccccggg ggcuguucgg cgcgaucgcc ggguucaucg agggcggcug gaccgggaug   1080
aucgacggcu gguacgggua ccaccaccag aacgagcagg gcagcgggua cgccgccgac   1140
cagaagucca cccagaacgc cagcaucggc aucaccaaca aggugaacac ggugaucgag   1200
aagaugaaca uccaguucac cgcggucggc aaggaguuca caagcucga gaagcgcaug   1260
gagaaccuga caagaaggu ggacgacggg uuccuggaca ucuggaccua caacgccgag   1320
cuccuggugc ugcucgagaa cgagcggacc cuggacuucc acgacagcaa cgucaagaac   1380
cuguacgaga aggugaaguc ccagcucaag aacaacgcca aggagaucgg caacggguc    1440
uucgaguucu accacaagug cgacaacgag ugcauggaga gcguccgcaa cggcacguac   1500
gacuacccca aguacuccga ggagagcaag cugaaccggg agaagguggga cggggugaag   1560
cuggagucca uggggcaucua ccagauccuc gccaucuaca gcaccgucgc cuccagccug   1620
gugcugcugg ugccccucgg cgcgaucagc uucggaugu gcagcaacgg guccccugcag   1680
ugccgcaucu gcaucuga                                                  1698
```

<210> SEQ ID NO 385
<211> LENGTH: 1161
<212> TYPE: RNA
<213> ORGANISM: Artificial Sequence
<220> FEATURE:
<223> OTHER INFORMATION: Ovalbumin (control) mRNA

<400> SEQUENCE: 385

```
augggcagca ucggggccgc gucgauggag uucugcuucg acguguucaa ggagcugaag      60
```

-continued

```
guccaccacg ccaacgagaa caucuucuac ugcccgaucg ccaucaugag cgcgcucgcc        120 auguguacc ugggcgccaa ggacagcacc cggacgcaga ucaacaaggu gguccgcuuc         180
gacaagcugc ccggcuucgg ggacucgauc gaggcgcagu gcggcaccag cgugaacgug        240
cacagcucgc uccgggacau ccugaaccag aucaccaagc cgaacgacgu cuacagcuuc        300
agccuggccu cgcggcucua cgccgaggag cgcuacccga uccugcccga guaccugcag        360
ugcgugaagg agcucuaccg gggcgggcug gagccgauca acuuccagac ggcggccgac        420
caggcccggg agcugaucaa cagcugggug gagagccaga ccaacggcau cauccgcaac        480
guccuccagc cgucgagcgu ggacagccag accgcgaugg ugcuggucaa cgccaucgug        540
uucaagggcc ugugggagaa gacguucaag gacgaggaca cccaggccau gcccuuccgg        600
gugaccgagc aggagucgaa gccgguccag augauguacc agaucgggcu cuuccgggug        660
gcgagcaugg ccagcgagaa gaugaagauc cuggagcugc cguucgccuc gggcacgaug        720
agcaugcucg ugcugcugcc cgacgagguc agcggccucg agcagcugga gucgaucauc        780
aacuucgaga agcugaccga guggaccagc agcaacguga uggaggagcg caagaucaag        840
guguaccucc cgcggaugaa gauggaggag aaguacaacc ugacgucggu ccugauggcg        900 augggggauca ccgacguguu cagcagcucg gccaaccuca gcggcaucag cucggccgag       960
agccugaaga ucagccaggc ggugcacgcc gcccacgcgg agaucaacga ggccggccgg       1020
gaggucgugg ggucggccga ggcgggcgug gacgccgcca gcgucagcga ggaguuccgc       1080
gcggaccacc cguuccuguu cugcaucaag cacaucgcca ccaacgccgu gcucuucuuc       1140
ggccggugcg ugucgcccug a                                                 1161
```

VACCINATION IN NEWBORNS AND INFANTS

CROSS REFERENCE TO RELATED APPLICATIONS

This application is a U.S. National Phase filing under 35 U.S.C. §371 of International Application PCT/EP2012/000877, filed Feb. 29, 2012, and published as WO 2012/116810 on Sep. 7, 2012. PCT/EP2011/000877 claimed benefit of priority from International Application PCT/EP2011/001047, filed Mar. 2, 2011. The entire contents of each of the prior applications are hereby incorporated herein by reference. Subject matter incorporated by reference is not considered to be an alternative to any claim limitations, unless otherwise explicitly indicated.

The present invention relates to vaccines comprising at least one mRNA encoding at least one antigen for use in the treatment of a disease in newborns and/or infants, preferably exhibiting an age of not more than 2 years, preferably of not more than 1 year, more preferably of not more than 9 months or even 6 months, wherein the treatment comprises vaccination of the newborn or infant and eliciting an immune response in said newborn or infant. The present invention is furthermore directed to kits and kits of parts comprising such a vaccine and/or its components and to methods applying such a vaccine or kit.

Diagnosing, preventing and treating infections and allergies in newborns and infants are of major interest and increasingly the subject of intense research worldwide. In this context, a profound knowledge about the mechanisms of the immune system of newborns and infants is of major importance. As widely known, the primary role of the immune system is to protect the organism against pathogens, but the response of the immune system to such pathogens is not equal throughout the whole life span. It is further known that responses of the immune system undergo age-associated alterations. Likewise, responses of the immune system of newborns and infants are not equal to those of adults. Particularly the response of T and B cells differs in many aspects, a fact, which may be contributed to the necessity of the prenatal requirements of the fetal immune system and the transition to the external conditions during birth.

As is well known, all organ systems of the body undergo a dramatic transition during birth from a sheltered intra-uterine existence to the radically distinct environment of the outside world. This acute transition is then followed by a gradual, age-dependent maturation. As reviewed by Ofer (see Ofer, NATURE REVIEWS|IMMUNOLOGY VOLUME 7|MAY 2007|379) the fetal and neonatal immune systems are usually associated with physiological demands that are three-fold: protection against infection, including viral and bacterial pathogens at the maternal-fetal interface, avoidance of potentially harmful pro-inflammatory/T helper 1 (Th1)-cell polarizing responses that can induce alloimmune reactions between mother and fetus, and mediation of the transition between the normally sterile intra-uterine environment to the foreign antigen-rich environment of the outside world, including primary colonization of the skin and intestinal tract by microorganisms. Given the limited exposure to antigens in utero and the well-described defects in neonatal adaptive immunity, newborns must rely on their innate immune systems for protection to a significant extent. As the innate immune system can instruct the adaptive immune response, distinct functional expression of neonatal innate immunity, including a bias against Th1-cell-polarizing cytokines, contributes to a distinct pattern of neonatal adaptive immune responses. Mounting evidence indicates that infection-induced production of pro-inflammatory/Th1 cell-polarizing cytokines, including tumour-necrosis factor (TNF) and interleukin-1β (IL-1β) is associated with premature labour and pre-term delivery. In particular, TNF production is thought to favour abortion through the induction of apoptosis in placental and fetal cells. The ability of pro-inflammatory cytokines to induce spontaneous abortion is likely to be an important reason for the strong bias of the maternal and fetal immune systems of multiple mammalian species towards TH2-cell-polarizing cytokines (see Levy, 2007, supra).

Because of this impaired production of Th1 cell associated cytokines, it was initially thought that the neonatal innate immune system was generally impaired or depressed; however, stimulus-induced production of certain cytokines (for example, IL-6, IL-10 and IL-23) by neonatal monocytes and antigen presenting cells (APCs) actually exceeds that of adults (see Angelone, D. et al., Pediatr. Res. 60, 205-209 (2006); Vanden Eijnden, S., Goriely, S., De Wit, D., Goldman, M. & Willems, F. Eur. J. Immunol. 36, 21-26, (2006); Chelvarajan, R. L. et al., J. Leukoc. Biol. 75, 982-994 (2004)). Nevertheless, there still appears to be a bias against Th1 cell-polarizing cytokines, which leaves the newborn susceptible to microbial infections and contributes to the impairment of neonatal immune responses to most vaccines, thereby frustrating efforts to protect this vulnerable population. After birth, there is an age-dependent maturation of the immune response. Of note, prenatal and postnatal exposure to environmental microbial products that can activate innate immunity might accelerate this maturation process, particularly if the exposure occurs repeatedly over time, diminishing TH2-cell polarization and/or enhancing Th1 cell polarization and thereby potentially reducing allergy and atopy, in accord with the hygiene hypothesis (see again Levy, 2007, supra).

T cell mediated immune responses in early life, particularly in newborns, have been reviewed by Marchant and Goldmann (see Marchant and Goldmann, Clinical and Experimental Immunology, 2005, 14: 10-18). As stated there circulating neonatal T lymphocytes are fundamentally different from naïve adult T cells and have characteristics of recent thymic emigrants. They contain high concentrations of T cell-receptor excision circles (TRECs), episomal DNA by products of TCRα-chain rearrangement that are not replicated but diluted during cell division. Like adult naïve cells, most neonatal T lymphocytes express the CD45 RA$^+$ isoform and the costimulatory molecules CD27 and CD28. In contrast to adult naïve lymphocytes, neonatal lymphocytes express the CD38 molecule. In addition, a high proportion of circulating neonatal T cells are in cycle and display an increased susceptibility to apoptosis indicating high cell turn-over. Proliferation of naïve T lymphocytes can also be detected during fetal life and could last up to five years of age. The high cell turn-over observed in early life probably plays a central role in the establishment of the T cell repertoire. Despite their high turn-over, T cells preserve long telomeric sequences through a high constitutive telomerase activity. In vitro apoptosis of neonatal T lymphocytes can be prevented by cytokines signalling through the γ-chain of the IL-2 receptor, namely IL-2, IL-4, IL-7 and IL-15. Among these cytokines, IL-7 and IL-15 also induce the proliferation of neonatal T lymphocytes in the absence of other stimuli. IL-7 is involved in thymocyte development at a stage preceding the T cell receptor rearrangement. IL-15 preferentially stimulates the proliferation of CD8 rather than CD4+ T cells. In contrast to IL-7, IL-15 induces the differentiation of CD8+ T lymphocytes in vitro (see Marchant and Goldmann, 2005, supra).

Several mechanisms limit T helper 1 (Th1) type responses in early life. In utero, Th1 responses are toxic to the placenta and are inhibited by trophoblast-derived IL-10 and progesterone. At birth, Th1 responses are still of lower magnitude than later in life. In vitro, CD4+ T cells of newborns produce lower levels of IFNγ than naïve T cells of adults and are hypermethylated at CpG and non-CpG sites within the IFNγ promoter. In the presence of suboptimal CD28 costimulation, IL-12 stimulates the production of both IL-4 and IFNγ by neonatal CD4 T lymphocytes whereas adult cells do not produce IL-4 under similar conditions. In response to polyclonal or superantigen activation, postnatal thymocytes develop into Th2 cytokine producing CD4 cells whereas IL-12 is required to stimulate the production of IFNγ. In contrast, neonatal CD8+ T cells produce similar levels of IFNγ and have a pattern of IFNγ promoter methylation comparable to that of naïve adult cells. In addition, neonatal CD8 T lymphocytes are strictly dependent on the presence of IL-4 at the time of priming to differentiate into IL-4-producing cells. The capacity of neonatal CD4 T lymphocytes to express CD40 ligand (CD154), a molecule playing a critical role in the help to B lymphocytes and CD8+ T cells, remains controversial (see also Marchant and Goldmann, 2005, supra).

Together, the available data indicate that naïve T lymphocytes are differently programmed in neonates and in adults. As may be summarized, the capacity of neonatal CD4+ T cells to produce IFNγ and of neonatal DCs to promote Th1 responses is lower as compared to adults in in vitro studies. Additionally, Th1 responses to a number of vaccines and infectious pathogens in vivo are poor during early life. However, mature Th1 responses can develop in certain conditions such as neonatal BCG vaccination and *Bordetella pertussis* infection, probably in relation with a more efficient activation of DCs. Accordingly, the classical paradigm that newborns have incompetent T lymphocytes developing only weak or even tolerogenic responses has to be reconsidered. The observation that mature cellular immune responses can be developed in early life suggests that under appropriate conditions of stimulation neonatal T lymphocytes may be instructed to fight intracellular pathogens (see also Marchant and Goldmann, 2005, supra).

Not only differences in T cell responses but also differences in B cell responses appear to exhibit a severe impact on immunoprotection in newborns and/or infants with respect to adult individuals. It has long been thought that the vulnerability of children younger than 18-24 months of age to encapsulated bacteria such as *pneumococcus, Haemophilus influenzae* B (Hib) and *meningococcus* has long been thought to reflect a general failure to generate T cell-independent B cell responses to most bacterial polysaccharides (see Claire-Anne Siegrist* and Richard Aspinall, NATURE REVIEWS|IMMUNOLOGY VOLUME 9|MARCH 2009|185). However, immaturity of the immune system in newborns and/or infants also has a direct effect on the magnitude of antibody responses to T cell-dependent protein antigens. Mechanisms that shape B cell responses in early life were investigated using neonatal mouse immunization models that were developed to reproduce the main limitations of immune responses to vaccines that are administered at an early age (see Claire-Anne Siegrist* and Richard Aspinall, 2009, supra). There are numerous differences between neonatal and adult mouse splenic B cells, although fewer differences have been identified by comparing human peripheral B cells. Specifically, human neonatal B cells express lower levels of the co-stimulatory molecules CD40, CD80 and CD86, which decreases their responses to CD40 ligand (CD40L) and interleukin-10 (IL-10) expressed by T cells. Splenic marginal zone infant B cells express lower levels of CD21, which limits their capacity to respond to polysaccharide-complement complexes. The expression of TACI (transmembrane activator and calcium-modulating cyclophilin-ligand interactor; also known as TNFRSF13B), an important co-stimulatory receptor, is also decreased on both neonatal mouse and neonatal human B cells, particularly those born prematurely. In addition, B cell responses in early life are influenced by numerous extrinsic factors. Antibodies of maternal origin bind to vaccine antigens in an epitope specific manner and therefore prevent infant B cells from accessing immunodominant vaccine epitopes. Furthermore, human and mouse neonates have low levels of serum complement component C3, which limits their responses to antigen-C3d complexes. The human spleen contains fewer marginal zone macrophages (which have a crucial role in the induction of an antibody response through the trapping of particulate antigens) in neonates than in adults, and the cells differ in their capacity to produce cytokines. In infant mice, B cell responses are limited by a marked delay in the maturation of the follicular dendritic cell (FDC) network, resulting from the failure of FDC precursors to respond to B cell-mediated lymphotoxin-α signalling. FDCs nucleate germinal centre reactions by attracting antigen-specific B cells, retain antigens in the form of immune complexes that are highly stimulatory to B cells and provide signals that lead to somatic hypermutation and class-switch recombination. The immaturity of the FDC network therefore delays the induction and limits the magnitude of germinal centre responses, even when potent adjuvants that induce adult-like B cell, T cell and DC activation patterns are used. Additional to the postnatal maturation of antibody responses, the antibody persistence in vivo exhibits an important effect. The long-term maintenance of specific antibodies with a short half-life requires the persistence of antibody-producing B cells, which can either be continually produced from a pool of memory B cells or can persist as long-lived plasma cells. Antibody mediated depletion of memory B cells, which does not affect plasma cells, has shown that the plasma-cell stage is independent of the memory B cell pool. It has also been shown, that persistence of antibodies in vivo may be influenced by environmental factors. This supports the hypothesis that the limited persistence of antibody responses in early life results from exposure to a large load of environmental antigens, which results in competition for access to a limited set of plasma-cell survival niches in the bone marrow (see Claire-Anne Siegrist* and Richard Aspinall, 2009, supra).

As known before, the administration of a single dose of vaccine at birth can fail to elicit specific antibodies while priming for subsequent secondary responses, which indicates a preferential neonatal differentiation pathway towards memory B cells rather than plasma cells. Several factors seem to contribute to this B cell differentiation pattern. The fate of antigen-specific naive B cells and their differentiation to short-lived plasma cells, long-lived plasma cells or memory B cells is controlled by early B cell activation signals. High-affinity B cells are actively recruited to the plasma-cell pool, whereas moderate-affinity B cells remain as memory B cells in the secondary lymphoid organs. So, decreased initial B cell receptor affinity and/or delayed affinity maturation of neonatal naive B cells might decrease the strength of the signal and favour memory B cell differentiation.

The limited expression of CD21 by infant B cells also supports the generation of memory B cells and impairs the development of plasma cells, which would be supported by CD40-mediated signalling, cytokines such as Il-21 and interactions with ligands such as B cell activating factor (BAFF; also known as TNFSF13B) and APRIL. Remarkably, these plasma-cell-supporting factors are all expressed at low levels early in life, unless additional activation signals are provided to enhance DC and T cell activation. Furthermore, early-life B cells might have to compete for limited resources within the germinal centre, which impairs antibody responses. Plasma-cell differentiation may thus be 'forced' in early life by providing additional DC activation signals. Therefore, a combination of factors appears to result in the preferential differentiation of early-life B cells towards memory B cells instead of long-lived plasma cells in a pattern. Importantly, although it has been shown that the memory B cell pool can be formed early in life, this should not be considered as evidence that its magnitude or persistence is similar to that elicited in immunologically mature hosts. Recent observations of the failure of booster vaccines to elicit a memory response in adolescents or young adults that had been primed against hepatitis B virus in infancy suggest that infant-triggered memory B cells might not last life long. Whether this reflects a smaller B cell pool in infants and/or the influence of as yet undefined homeostatic factors remains to be determined. In summary, a large number of B cell intrinsic factors and extrinsic determinants appear to cooperate to limit the induction and the persistence of antibody-secreting plasma cells in early life, while supporting the preferential induction of memory B cell responses (see Claire-Anne Siegrist* and Richard Aspinall, 2009, supra).

Alterations in T cell responses and also in B cell responses as discussed above exhibit a significant effect not only on immunoprotection towards pathogens but also to vaccination strategies in newborns and/or infants when combating infectious diseases but possibly also allergies, autoimmune disorders or further diseases. Many attempts have been carried out to provide efficient vaccines, which may overcome at least some of the above limitations.

One previous approach to overcome theses deficiencies in the context of virus-based influenza vaccines refers to the administration of naked DNA plasmid (pHA) expressing hemagglutinin (HA) from the neurovirulent strain A/WSN/33 of influenza virus to prime protective immune responses by inoculating newborn and adult mice (see Bot et al, 1997, *International Immunology*, Vol. 9, No. 11, pp. 1641-1650). As shown by Bot et al. (1997) continuous exposure to small doses of antigen subsequent to neonatal DNA immunization may lead to priming of specific B and Th cells, rather than tolerance induction. However, only pHA immunization of adult mice primed a strongly biased Th1 response, whereas in neonates it induced a mixed Th1/Th2 response. One further very similar approach of the same working group was directed to the combined administration of plasmids expressing nucleoprotein (NP) or hemagglutinin (HA) of influenza virus. Neonatal immunization of BALB/c mice was followed by priming of B cells, Th cells and CTL rather than tolerance (see Bot et al., Vaccine, Vol. 16, No. 17, pp. 16751682, 1998). However, protection in terms of survival against lethal challenge with homologous or heterologous strains was not reported to be complete. Further, in the case of NP expressing plasmid, the protective immunity elicited by neonatal immunization required a longer time to develop, as compared with adult immunization. Neither Bot et al. (1997, supra) nor Bot et al. (1998, supra) showed good Th1 responses in neonates. Furthermore, even though it was stressed in both papers that DNA vaccination represents an efficient and safe means to generate broad humoral and cellular immune responses to influenza viruses during the earliest stages of postnatal life, DNA has been encountered meanwhile as dangerous due to unwanted insertion into the genome. Such DNA based vaccinations may even lead to interruption of functional genes and cancer or the formation of anti-DNA antibodies and are therefore out of focus as of today.

Further approaches were directed to improvement of delivery systems and administration of immunomodulators to optimize vaccine responses in early life. Jiri Kovarik and Claire-Anne Siegrist focus on problems arising from the attempt to vaccinate against pathogens very early in life and on the role of selective adjuvants that could be used to: (i) rapidly induce strong antibody responses of the appropriate isotypes; (ii) elicit sustained antibody responses extending beyond infancy; (iii) induce efficient Th1 and CTL responses in spite of the preferential Th2 polarization of early life responses; (iv) escape from maternal antibody mediated inhibition of vaccine responses; (v) show acceptable reactogenicity in early life; and (vi) allow incorporation of several vaccine antigens into a single formulation so as to reduce the number of required injections (see Jiri Kovarik and Claire-Anne Siegrist, *Immunology and Cell Biology* (1998) 76, 222-236). Kovarik and Siegrist (1998, supra) inter alia discuss different antigen delivery systems such as administration of particulate substances, emulsions, liposomes, virosomes, microspheres, live vaccines, vectors and DNA vaccines as well as the use of immunomodulators such as MPL, QS21, MDP derivatives, cytokines, interferons, and CpG oligodesoxynucleotides and combinations of antigen presentation systems and immunomodulators. However, as likewise shown in Kovarik and Siegrist (1998, supra) many of these combinations are hypothetical and may not even provide an efficient Th1 response or even lead to unwanted side effects.

Similarly, Adrian Bot and Constantin Bona (see Adrian Bot and Constantin Bona, Microbes and Infection 4 (2002) 511-520) suggest the use of bacterial CpG motifs to activate immature antigen-presenting cells and to enhance neonatal immunogenicity of DNA vaccines. Additionally, Bot and Bona (2002, supra) suggest a combination with subsequent boosting using conventional vaccines. Nevertheless, the strategy outlined in this paper does not lead to convincing Th1 responses. Furthermore, the approach is based on the use of DNA vaccine, which may be regarded as potentially dangerous as outlined above.

A further promising but very specific strategy relies on the use of the specific novel adjuvant IC31. As known in the art, there are only few adjuvants approved for human use. One major adjuvant approved for human use is e.g. Alum, an aluminium salt based adjuvant. However, although approved for human use, such aluminium salts failed to provide satisfactory augmentation of immune responses for seasonal influenza vaccines in early human clinical trials, an effect, which may be expected likewise during other vaccination strategies. Further licensed adjuvanted influenza vaccines include to date FLUAD® (Novartis Vaccines), containing MF59 in combination with a subunit vaccine formulation, and the virosomal vaccines INFLEXAL®V (Berna Biotech, a Crucell company) and INVIVAC® (Solvay). Although animal studies and human clinical trials revealed a higher immunogenicity profile—defined as increased antibody responses—with the MF59-adjuvanted influenza vaccine, MF59 is not a potent adjuvant for the induction of type 1 driven cellular immune responses. Unlike FLUAD®, the virosomal vaccines represent reconstituted influenza virus envelopes containing the functional influenza surface proteins haemagglutinin and neuraminidase in their phospholipid bilayer. The immunogenicity and local tolerability of virosome-based influenza vaccines has been shown in several studies. However, the development of virosomal formulations is very complex and the costs of goods are high.

In this context, Kamath et al. (see Kamath et al., 2008, PLoS ONE 3(11): e3683. doi:10.1371/journal.pone.0003683) report the use of a specific adjuvant IC31 with Ag85b-ESAT-6 fusion protein for immunization of neonatal mice and adult mice. Conversely to Alum, IC31H induced strong Th1 and Th17 responses in both age groups, characterized by multifunctional T cells expressing IL-2 and TNFα with or without IFNγ. In the draining lymph nodes, a similarly small number of DC contained the adjuvant and/or the antigen following neonatal or adult immunization. Expression of CD40, CD80, CD86 and IL-12p40 production was focused on the minute adjuvant-bearing DC population, wherein DC targeting/activation was similar in adults and neonates. These DC/T cell responses resulted in an equivalent reduction of bacterial growth following infection with *M. bovis* BCG, whereas no protection was observed when Alum was used as adjuvant. However, no further adjuvants are shown in Kamath et al. (2008, supra), which allow extension of this specific example to other vaccines.

Summarizing the above, none of the present prior art vaccines allow to efficiently evoke immune responses in newborns and/or infants, which show at least similar characteristics as an immune response in adults. Particularly, many vaccines fail to provide an efficient Th1 immune response in newborns and/or infants. Accordingly, there is an urgent need for vaccines optimized for such patients. More precisely, vaccines are required, which do not bear the problems shown in the prior art or at least diminish these problems to a significant extent. Furthermore, it is highly envisaged to provide vaccines, which allow inducing Th1 immune responses in newborns and/or infants, preferably without leading to a shift from Th1 to Th2 immune responses subsequent to administration. Likewise, the administration of DNA based vaccines should be avoided due to possible insertion of DNA into the genome, possible interruption of genes and formation of anti-DNA antibodies.

The object underlying the present invention is solved by the subject matter of the attached claims, more preferably as outlined in the following.

According to a first embodiment, the object underlying the present invention is solved by a vaccine comprising at least one mRNA encoding at least one antigen for use in the prophylaxis and/or treatment of a disease in newborns and/or infants, preferably exhibiting an age of not more than 2 years, preferably of not more than 1 year, more preferably of not more than 9 months or even 6 months, wherein the treatment comprises vaccination of the newborn or young infant and eliciting an immune response in said newborn or infant.

Without being bound to theory RNA vaccines elegantly integrate adjuvanticity and antigen expression, thereby mimicking relevant aspects of viral infections. This increases their efficacy compared to other inactivated (dead) vaccines that require the use of advanced adjuvants in a newborn or an infant, simplifying handling and production. RNA can address a range of dedicated immunologic pattern recognition receptors, including toll-like receptors 3, 7, and 8, RIG-I, MDA5, PKR, and others that may act synergistically and serve to enhance the induction of antigen-specific adaptive B and T cell responses. Importantly, by antigen synthesis in transfected host cells, mRNA vaccines directly introduce antigen into cellular antigen processing and presentation pathways, granting access to MHC molecules and triggering T cell responses, irrespective of the hosts MHC haplotype. This enables the induction of polyclonal T cell responses that may act synergistically with other immune responses, including B cells. Also, presenting the full spectrum of MHC-binding epitopes may circumvent limitations by immature immune systems in a newborn or an infant. Also, endogenous production of antigen ensures faithful posttranslational modification (e.g. proteolytic processing, glycosylation, etc.) that may positively impact immunogenicity. Also, RNA vaccines exhibit safety features that make them superior for use in newborns and/or infants. For example, the increased reactogenicity of live attenuated vaccines generally prevents use in this highly relevant target group. However, considering the short persistence and traceless decay of the vaccine vector within a matter of days the observed good immunogenicity is unexpected and contrasts claims for plasmid DNA vaccines that variously linked efficacy to the persistent expression of antigen.

The at least one mRNA of the inventive vaccine as defined in the first embodiment of the present invention, encoding at least one antigen, may be selected from any antigen, known to a skilled person, preferably suitable to elicit an antigen-specific immune response in a patient. According to the present invention, the term "antigen" refers to a substance which is recognized by the immune system and is capable of triggering an antigen-specific immune response, e.g. by formation of antibodies or antigen-specific T cells as part of an adaptive immune response. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses. Tissue dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both TH2 and Th1 cells to produce different classes of antibody, thus driving the humoral immune response. T cells recognize an antigen by their T cell receptors which do not recognize and bind antigen directly, but instead recognize short peptide fragments e.g. of pathogens' protein antigens, which are bound to MHC molecules on the surfaces of other cells.

In the context of the present invention, antigens as encoded by the at least one mRNA of the inventive vaccine typically comprise any antigen, falling under the above definition, more preferably protein and peptide antigens. In accordance with the invention, antigens as encoded by the at least one mRNA of the inventive vaccine may be antigens generated outside the cell, more typically antigens not derived from the host organism (e.g. a human) itself (i.e. non-self antigens) but rather derived from host cells outside the host organism, e.g. pathogenic antigens, particularly viral antigens, bacterial antigens, fungal antigens, protozoological antigens, animal antigens (preferably selected from animals or organisms as disclosed herein), allergy antigens, etc. Antigens as encoded by the at least one mRNA of the inventive vaccine may be furthermore antigens generated inside the cell, the tissue or the body, e.g. by secretion of proteins, their degradation, metabolism, etc. Such antigens include antigens derived from the host organism (e.g. a human) itself, e.g. tumour antigens, self-antigens or auto-antigens, such as auto-immune self-antigens, etc., but also (non-self) antigens as defined above, which have been originally been derived from host cells outside the host organism, but which are fragmented or degraded inside the body, tissue or cell, e.g. by (protease) degradation, metabolism, etc.

Pathogenic antigens particularly comprise e.g. antigens from influenza, preferably influenza A, influenza B, influenza C or thogotovirus, preferably influenza antigens haemagglutinin (HA) and/or neuraminidase (NA), preferably influenza antigens derived from haemagglutinin subtypes H1, H2, H3, H4, H5, H6, H7, H8, H9, H10, H11, H12, H13, H14 or H15, and/or neuraminidase subtypes N1, N2, N3, N4, N5, N6, N7, N8 or N9, or preferably selected from influenza A subtypes H1N1, H1N2, H2N2, H2N3, H3N1, H3N2, H3N3, H5N1, H5N2, H7N7 or H9N2, or any further combination, or from matrix protein 1 (M1), ion channel protein M2 (M2), nucleoprotein (NP), etc; or e.g. antigens from respiratory syncytial virus (RSV), including F-protein, G-protein, etc.

One further class of antigens as encoded by the at least one mRNA of the inventive vaccine comprises allergy antigens. Allergy antigens are typically antigens, which cause an allergy in a human and may be derived from either a human or other sources. Such allergy antigens may be selected from antigens derived from different sources, e.g. from animals, plants, fungi, bacteria, etc. Allergens in this context also include antigens derived from e.g. grasses, pollens, molds, drugs, or numerous environmental triggers, etc. Allergy antigens typically belong to different classes of compounds, such as proteins or peptides and their fragments, carbohydrates, polysaccharides, sugars, lipids, phospholipids, etc. Of particular interest in the context of the present invention are antigens, which are encoded by the at least one mRNA of the inventive vaccine, i.e. protein or peptide antigens and their fragments or epitopes, or nucleic acids and their fragments, particularly nucleic acids and their fragments, encoding such protein or peptide antigens and their fragments or epitopes.

Particularly preferred, antigens derived from animals, which are encoded by the at least one mRNA of the inventive vaccine, may include antigens derived from, without being limited thereto, insects, such as mite (e.g. house dust mites), mosquito, bee (e.g. honey bee, bumble bee), cockroach, tick, moth (e.g. silk moth), midge, bug, flea, wasp, caterpillar, fruit fly, migratory locust, grasshopper, ant aphid, from crustaceans, such as shrimps, crab, krill, lobster, prawn, crawfish, scampi, from birds, such as duck, goose, seagull, turkey, ostrich, chicken, from fishes, such as eel, herring, carp, seabream, codfish, halibut, catfish, beluga, salmon, flounder, mackerel, cuttlefish, perch, form mollusks, such as scallop, octopus, abalone, snail, whelk, squid, clam, mussel, from spiders, from mammals, such as cow, rabbit, sheep, lion, jaguar, leopard, rat, pig, buffalo, dog, loris, hamster, guinea pig, fallow deer, horse, cat, mouse, ocelot, serval, from arthropod, such as spider, or silverfish, from worms, such as nematodes, from *trichinella* species, or roundworm, from amphibians, such as frogs, or from sea squirt, etc. Antigens derived from animals may also comprise antigens contained in animal products, preferably contained in animal products derived from animals as defined above, e.g. milk, eggs, meat, etc., but also from excrements or precipitates of any kind, derived from any of these animals.

Most preferably, antigens derived from animals, which are encoded by the at least one mRNA of the inventive vaccine, may include antigens derived from such animals, causing a disease as defined herein, preferably an infectious disease or an autoimmune disease as defined herein, or any further disease as defined herein.

Antigens derived from plants, which are encoded by the at least one mRNA of the inventive vaccine, may include antigens derived from, without being limited thereto, fruits, such as kiwi, pineapple, jackfruit, papaya, lemon, orange, mandarin, melon, sharon fruit, strawberry, lychee, apple, cherry paradise apple, mango, passion fruit, plum, apricot, nectarine, pear, passion fruit, raspberry, grape, from vegetables, such as garlic, onion, leek, soya bean, celery, cauliflower, turnip, paprika, chickpea, fennel, zucchini, cucumber, carrot, yam, bean, pea, olive, tomato, potato, lentil, lettuce, avocado, parsley, horseradish, chirimoya, beet, pumpkin, spinach, from spices, such as mustard, coriander, saffron, pepper, aniseed, from crop, such as oat, buckwheat, barley, rice, wheat, maize, rapeseed, sesame, from nuts, such as cashew, walnut, butternut, pistachio, almond, hazelnut, peanut, brazil nut, pecan, chestnut, from trees, such as alder, hornbeam, cedar, birch, hazel, beech, ash, privet, oak, plane tree, cypress, palm, from flowers, such as ragweed, carnation, forsythia, sunflower, lupine, chamomile, lilac, passion flower, from grasses, such as quack grass, common bent, brome grass, Bermuda grass, sweet vernal grass, rye grass, or from other plants, such as opium poppy, pellitory, ribwort, tobacco, asparagus, mugwort, cress, etc.

Antigens derived from fungi, which are encoded by the at least one mRNA of the inventive vaccine, may include antigens derived from, without being limited thereto, e.g. *Alternia* sp., *Aspergillus* sp., *Beauveria* sp., *Candida* sp., *Cladosporium* sp., *Endothia* sp., *Curcularia* sp., *Embellisia* sp., *Epicoccum* sp., *Fusarium* sp., *Malassezia* sp., *Penicillum* sp., *Pleospora* sp., *Saccharomyces* sp., etc.

Antigens derived from bacteria, which are encoded by the at least one mRNA of the inventive vaccine, may include antigens derived from, without being limited thereto, e.g. *Bacillus tetani, Staphylococcus aureus, Streptomyces griseus*, etc.

One further class of antigens as encoded by the at least one mRNA of the inventive vaccine comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof; in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. According to the invention, the terms "cancer diseases" and "tumour diseases" are used synonymously herein.

Examples of tumour antigens as encoded by the at least one mRNA of the inventive vaccine may comprise e.g. antigens selected from the group comprising, without being limited thereto, 5T4, 707-AP (707 alanine proline), 9D7, AFP (alpha-fetoprotein), AlbZIP HPG1, alpha5beta1-Integrin, alpha5beta6-Integrin, alpha-methylacyl-coenzyme A racemase, ART-4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT-9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumour cell-associated extracellular matrix metalloproteinase inducer/), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CAIX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumour-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor alpha 2 chain), IL-2R, IL-5, immature laminin receptor, kallikrein 2, kallikrein 4, Ki67, KIAA0205, KK-LC-1 (Kita-kyushu lung cancer antigen 1), KM-HN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigen-A4), MAGE-A6 (melanoma antigen-A6), MAGE-A9 (melanoma-antigen-A9), MAGE-B1 (melanoma-antigen-B1), MAGE-B10 (melanoma-antigen-B10), MAGE-B16 (melanoma-antigen-B16), MAGE-B17 (melanoma-antigen-B17), MAGE-B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucose-aminyltransferase-V, Neo-PAP (Neo-poly(A) polymerase), NGEP, NMP22, NPM/ALK (nucleophosmin/anaplastic lymphoma kinase fusion protein), NSE (neuron-specific enolase), NY-ESO-1 (New York esophageous 1), NY-ESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGE-like protein-4), PAI-1 (plasminogen activator inhibitor 1), PAI-2 (plasminogen activator inhibitor 2), PAP (prostate acic phosphatase), PART-1, PATE, PDEF, Pim-1-Kinase, Pin1 (Propyl isomerase), POTE, PRAME (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumour 1), SART-2 (squamous antigen rejecting tumour 1), SART-3 (squamous antigen rejecting tumour 1), SCC (squamous cell carcinoma antigen), Sp17 (sperm protein 17), SSX-1 (synovial sarcoma X breakpoint 1), SSX-2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP-2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumour gene), or may comprise e.g. mutant antigens expressed in cancer diseases selected from the group comprising, without being limited thereto, alpha-actinin-4/m, ARTC1/m, bcr/abl (breakpoint cluster region-Abelson fusion protein), beta-Catenin/m (beta-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R170I (arginine to isoleucine exchange at residue 170 of the alpha-helix of the alpha2-domain in the HLA-A2 gene), HLA-A11/m, HLA-A2/m, HSP70-2M (heat shock protein 70-2 mutated), KIAA0205/m, K-Ras/m, LDLR-FUT (LDR-Fucosyltransferase fusion protein), MART2/m, ME1/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS-9/m, p53/m, Pml/RARa (promyelocytic leukemia/retinoic acid receptor alpha), PRDX5/m, PTPRK/m (receptor-type protein-tyrosine phosphatase kappa), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFbRII (TGF-beta receptor II), TPI/m (triosephosphate isomerase). According to a specific aspect, however, mRNAs encoding antigens gp100, MAGE-A1, MAGE-A3, MART-1/melan-A, survivin, and/or tyrosinase, more preferably mRNAs encoding antigens gp100, MAGE-A1, MAGE-A3, MART-1/melan-A, survivin, and/or tyrosinase, wherein the mRNAs have been complexed with or stabilized with protamine (e.g. in a ratio of about 80 µg mRNA and 128 µg protamine), may be excluded from the scope of invention. In a preferred aspect the tumour antigens as encoded by the at least one mRNA of the inventive vaccine are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD40, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1.

According to a particularly preferred aspect, tumour antigens as encoded by the at least one mRNA of the inventive vaccine are selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), survivin (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_014302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

Particularly preferred, antigens are selected from Influenza A virus (HA, NA, NP, M2, M1 antigens), influenza B virus (HA, NA antigens), respiratory syncytial virus (F, G, M, SH antigens), parainfluenza virus (glycoprotein antigens), *Streptococcus pneumoniae* (pPht, PcsB, StkP antigens), *Corynebacterium diphtheriae, Clostridium tetani,* Measles, Mumps, Rubella, Rabies virus (G, N antigens), *Staphylococcus aureus* (toxin antigen), *Clostridium difficile* (toxin antigen), *Mycobacterium tuberculosis* (acute and dormant antigens), *Candida albicans, Haemophilus influenzae* B (HiB), poliovirus, hepatitis B virus (surface and core antigens), human papillomavirus (L1, L2, E6, E7), human immunodeficiency virus (gp120, gag, env antigens), SARS CoV (spike protein), *Staphylococcus aureus* (IsdA, IsdB, toxin antigens), Pertussis toxin, polio virus (VP1-4), *Plasmodium* (NANP, CSP protein, ssp2, ama1, msp142 antigens), *Staphylococcus aureus* (IsdA, IsdB, toxin), *Bordetella pertussis* (toxin), polio virus VP1-4, *Plasmodium* (NANP, CSP protein, ssp2, ama1, msp142 antigens)

Antigens as encoded by the at least one mRNA of the inventive vaccine may furthermore comprise fragments of such antigens as mentioned herein, particularly of protein or peptide antigens. Fragments of such antigens in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form.

Fragments of antigens as defined herein may also comprise epitopes of those antigens. Epitopes (also called "antigen determinants") are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

According to a further particularly preferred aspect, the tumour antigens as encoded by at least one mRNA of the inventive vaccine may form a cocktail of antigens, e.g. in an active (immunostimulatory) composition or a kit of parts (wherein preferably each antigen is contained in one part of the kit), preferably for eliciting an (adaptive) immune response for the treatment of a disease or disorder as defined herein. For this purpose, the inventive vaccine may comprise at least one mRNA, wherein each mRNA may encode at least one, preferably two, three, four or even more (preferably different) antigens as mentioned herein. Alternatively, the inventive vaccine may contain at least one, two, three, four or even more (preferably different) mRNAs, wherein each mRNA encodes at least one antigen as mentioned herein.

Such a cocktail of antigens, as encoded by the least one mRNA of the inventive vaccine may be used e.g. in the treatment of e.g. prostate cancer (PCa), preferably in the treatment of neoadjuvant and/or hormone-refractory prostate cancers, and diseases or disorders related thereto. For this purpose, the inventive vaccine may comprise at least one mRNA, wherein each mRNA may encode at least one, preferably two, three, four or even more (preferably different) antigens as mentioned herein. Alternatively, the inventive vaccine may contain at least one, two, three, four or even more (preferably different) mRNAs, wherein each mRNA encodes at least one antigen as mentioned herein. Preferably, the antigens are selected from PSA (Prostate-Specific Antigen)=KLK3 (Kallikrein-3), PSMA (Prostate-Specific Membrane Antigen), PSCA (Prostate Stem Cell Antigen), and/or STEAP (Six Transmembrane Epithelial Antigen of the Prostate).

Furthermore, such a cocktail of antigens, as encoded by the at least one mRNA of the inventive vaccine may be used in the treatment of e.g. non-small cell lung cancers (NSCLC), preferably selected from the three main sub-types squamous cell lung carcinoma, adenocarcinoma and large cell lung carcinoma, or of disorders related thereto. For this purpose, the inventive vaccine may comprise at least one mRNA, wherein each mRNA may encode at least one, preferably two, three, four, five, six, seven, eight, nine, ten eleven or twelve (preferably different) antigens as mentioned herein. Alternatively, the inventive vaccine may contain at least one, preferably two, three, four, five, six, seven, eight, nine, ten, eleven or twelve (preferably different) mRNAs, wherein each mRNA encodes at least one antigen as mentioned herein. Preferably, such antigens are selected from hTERT, WT1, MAGE-A2, 5T4, MAGE-A3, MUC1, Her-2/neu, NY-ESO-1, CEA, Survivin, MAGE-C1, and/or MAGE-C2.

In the above aspects, each of the above defined antigens may be encoded by one (monocistronic) mRNA. In other words, in this case the at least one mRNA of the inventive vaccine may comprise at least two (three, four, etc.) (monocistronic) mRNAs, wherein each of these at least two (three, four, etc.) (monocistronic) mRNAs may encode, e.g. just one (preferably different) antigen, preferably selected from one of the above mentioned antigen combinations.

According to a particularly preferred aspect, the at least one mRNA of the inventive vaccine may comprise (at least) one bi- or even multicistronic mRNA, preferably mRNA, i.e. (at least) one mRNA which carries, e.g. two or even more of the coding sequences of at least two (preferably different) antigens, preferably selected from one of the above mentioned antigen combinations. Such coding sequences, e.g. of the at least two (preferably different) antigens, of the (at least) one bi- or even multicistronic mRNA may be separated by at least one IRES (internal ribosomal entry site) sequence, as defined below. Thus, the term "encoding at least two (preferably different) antigens" may mean, without being limited thereto, that the (at least) one (bi- or even multicistronic) mRNA, may encode e.g. at least two, three, four, five, six, seven, eight, nine, ten, eleven or twelve or more (preferably different) antigens of the above mentioned group(s) of antigens, or their fragments or variants, etc. In this context, a so-called IRES (internal ribosomal entry site) sequence as defined herein can function as a sole ribosome binding site, but it can also serve to provide a bi- or even multicistronic RNA as defined herein which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukemia virus (MLV), simian immunodeficiency viruses (SIV) or cricket paralysis viruses (CrPV).

According to a further particularly preferred aspect, the at least one mRNA of the inventive vaccine may comprise a mixture of at least one monocistronic mRNA as defined herein, and at least one bi- or even multicistronic RNA, preferably mRNA, as defined herein. The at least one monocistronic RNA and/or the at least one bi- or even multicistronic RNA preferably encode different antigens, or their fragments or variants, the antigens preferably being selected from one of the above mentioned antigens, more preferably in one of the above mentioned combinations. However, the at least one monocistronic RNA and the at least one bi- or even multicistronic RNA may preferably also encode (in part) identical antigens selected from one of the above mentioned antigens, preferably in one of the above mentioned combinations, provided that the at least one mRNA of the inventive vaccine as a whole provides at least two (preferably different) antigens, as defined herein. Such an aspect may be advantageous e.g. for a staggered, e.g. time dependent, administration of one or several of the at least one mRNA of the inventive vaccine to a patient in need thereof. The components of such a vaccine may be contained in (different parts of) a kit of parts composition or may be e.g. administered separately as components of the same inventive vaccine as defined according to the present invention.

In a further preferred embodiment the at least one mRNA of the inventive vaccine (or any further nucleic acid as defined herein) may also occur in the form of a modified nucleic acid.

According to a first aspect, the at least one mRNA of the inventive vaccine (or any further nucleic acid as defined herein) may be provided as a "stabilized nucleic acid" that is essentially resistant to in vivo degradation (e.g. by an exo- or endo-nuclease).

In this context, the at least one mRNA of the inventive vaccine (or any further nucleic acid as defined herein) may contain backbone modifications, sugar modifications or base modifications. A backbone modification in connection with the present invention is a modification in which phosphates of the backbone of the nucleotides contained in the at least one mRNA of the inventive vaccine (or any further nucleic acid as defined herein) are chemically modified. A sugar modification in connection with the present invention is a chemical modification of the sugar of the nucleotides of the at least one mRNA of the inventive vaccine (or any further nucleic acid as defined herein). Furthermore, a base modification in connection with the present invention is a chemical modification of the base moiety of the nucleotides of the at least one mRNA of the inventive vaccine (or any further nucleic acid as defined herein).

According to a further aspect, the at least one mRNA of the inventive vaccine (or any further nucleic acid as defined herein) can contain a lipid modification. Such a lipid-modified nucleic acid typically comprises a nucleic acid as defined herein, e.g. an mRNA or any further nucleic acid. Such a lipid-modified mRNA of the inventive vaccine (or any further lipid-modified nucleic acid as defined herein) typically further comprises at least one linker covalently linked with that nucleic acid molecule, and at least one lipid covalently linked with the respective linker. Alternatively, the lipid-modified mRNA of the inventive vaccine (or any further lipid-modified nucleic acid as defined herein) comprises at least one nucleic acid molecule as defined herein, e.g. an mRNA or any further nucleic acid, and at least one (bifunctional) lipid covalently linked (without a linker) with that nucleic acid molecule. According to a third alternative, the lipid-modified mRNA of the inventive vaccine (or any further lipid-modified nucleic acid as defined herein) comprises a nucleic acid molecule as defined herein, e.g. an mRNA or any further nucleic acid, at least one linker covalently linked with that nucleic acid molecule, and at least one lipid covalently linked with the respective linker, and also at least one (bifunctional) lipid covalently linked (without a linker) with that nucleic acid molecule.

The at least one mRNA of the inventive vaccine (or any further nucleic acid as defined herein) may likewise be stabilized in order to prevent degradation of the mRNA (or any further nucleic acid molecule) by various approaches. It is known in the art that instability and (fast) degradation of RNA in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance particularly for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to another aspect, the at least one mRNA of the inventive vaccine may be modified and thus stabilized by modifying the G/C content of the mRNA, preferably of the coding region thereof.

In a particularly preferred aspect of the present invention, the G/C content of the coding region of the at least one mRNA of the inventive vaccine is modified, particularly increased, compared to the G/C content of the coding region of its particular wild type coding sequence, i.e. the unmodified mRNA. The encoded amino acid sequence of the mRNA is preferably not modified compared to the coded amino acid sequence of the particular wild type mRNA.

The modification of the G/C-content of the at least one mRNA of the inventive vaccine is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. According to the invention, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Preferably, the G/C content of the coding region of the at least one mRNA of the inventive vaccine is increased by at least 7%, more preferably by at least 15%, particularly preferably by at least 20%, compared to the G/C content of the coded region of the wild type mRNA. According to a specific aspect at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence.

In this context, it is particularly preferable to increase the G/C content of the at least one mRNA of the inventive vaccine to the maximum (i.e. 100% of the substitutable codons), in particular in the region coding for a protein, compared to the wild type sequence.

According to the invention, a further preferred modification of the at least one mRNA of the inventive vaccine, especially if the nucleic acid is in the form of an mRNA or codes for an mRNA, is based on the finding that the translation efficiency is also determined by a different frequency in the occurrence of tRNAs in cells. Thus, if so-called "rare codons" are present in the at least one mRNA of the inventive vaccine to an increased extent, the corresponding modified mRNA is translated to a significantly poorer degree than in the case where codons coding for relatively "frequent" tRNAs are present.

Preferably, the coding region of the at least one mRNA of the inventive vaccine is modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the at least one mRNA of the inventive vaccine, especially if the nucleic acid is in the form of an mRNA or codes for an mRNA, is modified such that codons for which frequently occurring tRNAs are available are inserted. In other words, according to the invention, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified at least one mRNA of the inventive vaccine with the "frequent" codons without modifying the amino acid sequence of the protein encoded by the coding region of the mRNA. This preferred aspect allows provision of a particularly efficiently translated and stabilized (modified) at least one mRNA of the inventive vaccine.

According to a further preferred aspect of the invention, the at least one mRNA of the inventive vaccine as defined herein or any further nucleic acid molecule as defined herein preferably has at least one 5' and/or 3' stabilizing sequence. These stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from Homo sapiens or Xenopus laevis may be mentioned as an example of stabilizing sequences which can be used in the present invention for a stabilized nucleic acid. Another example of a stabilizing sequence has the general formula (C/U)CCAN$_x$CCC(U/A)Py$_x$UC(C/U)CC (SEQ ID NO: 383), which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

Nevertheless, substitutions, additions or eliminations of bases are preferably carried out with the at least one mRNA of the inventive vaccine or any further nucleic acid molecule as defined herein, especially if the nucleic acid is in the form of an mRNA, using a DNA matrix for preparation of the nucleic acid molecule by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, N Y, 2001). In such a process, for preparation of the at least one mRNA of the inventive vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one mRNA to be prepared and a termination signal for in vitro transcription. The DNA molecule, which forms the matrix of the at least one mRNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), PGEM® series, e.g. PGEM® 1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

Nucleic acid molecules used according to the invention and as defined herein, e.g. the at least one mRNA of the inventive vaccine or any further nucleic acid molecule as defined herein, may be modified as outlined above for the at least one mRNA of the inventive vaccine.

Additionally, nucleic acid molecules used according to the invention and as defined herein, e.g. the at least one mRNA of the inventive vaccine or any further nucleic acid molecule as defined herein, may be prepared using any method known in the art, including synthetic methods such as e.g. solid phase synthesis, as well as in vitro methods, such as in vitro transcription reactions.

According to one preferred aspect of the present invention the at least one mRNA of the inventive vaccine may be administered naked without being associated with any further vehicle, transfection or complexation agent for increasing the transfection efficiency of the at least one mRNA.

In a further preferred aspect of the present invention the at least one mRNA of the inventive vaccine is associated with a vehicle, transfection or complexation agent for increasing the transfection efficiency of the at least one mRNA. Particularly preferred agents in this context suitable for increasing the transfection efficiency are cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, VP22 derived or analog peptides, Pestivirus Erns, HSV, VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from Drosophila antennapedia), pAntp, pIsl, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l;(Lys)_m;(His)_n;(Orn)_o;(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio) propane, DC-6-14: O,O-ditetradecanoyl-N-α-trimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

The at least one mRNA of the inventive vaccine encoding at least one antigen may also be complexed with a polymeric carrier formed by disulfide-crosslinked cationic components. The term "cationic component" typically refers to a charged molecule, which is positively charged (cation) at a pH value of about 1 to 9, preferably of a pH value of or below 9, of or below 8, of or below 7, most preferably at physiological pH values, e.g. about 7.3 to 7.4. Accordingly, a cationic peptide, protein or polymer according to the present invention is positively charged under physiological conditions, particularly under physiological salt conditions of the cell in vivo. The definition "cationic" may also refer to "polycationic" components.

In this context the cationic components, which form basis for the polymeric carrier of the inventive vaccine by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer, is preferably a linear molecule, however, branched cationic or polycationic peptides, proteins or polymers may also be used.

Each cationic or polycationic protein, peptide or polymer of the polymeric carrier, which may be used to complex the at least one mRNA of the inventive vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

Each cationic or polycationic protein, peptide or polymer or any further component of the polymeric carrier, which may be used to complex the at least one mRNA of the inventive vaccine is preferably linked to its neighbouring component(s) (cationic proteins, peptides, polymers or other components) via disulfide-crosslinking. Preferably, the disulfide-crosslinking is a (reversible) disulfide bond (—S—S—) between at least one cationic or polycationic protein, peptide or polymer and at least one further cationic or polycationic protein, peptide or polymer or other component of the polymeric carrier. The disulfide-crosslinking is typically formed by condensation of —SH-moieties of the components of the polymeric carrier particularly of the cationic components. Such an —SH-moiety may be part of the structure of the cationic or polycationic protein, peptide or polymer or any further component of the polymeric carrier prior to disulfide-crosslinking or may be added prior to disulfide-crosslinking by a modification as defined below. In this context, the sulphurs adjacent to one component of the polymeric carrier, necessary for providing a disulfide bond, may be provided by the component itself, e.g. by a —SH moiety as defined herein or may be provided by modifying the component accordingly to exhibit a —SH moiety. These —SH-moieties are typically provided by each of the components, e.g. via a cysteine or any further (modified) amino acid of the component, which carries a —SH moiety. In the case that the cationic component or any further component of the polymeric carrier is a peptide or protein it is preferred that the —SH moiety is provided by at least one cysteine residue. Alternatively, the component of the polymeric carrier may be modified accordingly with a —SH moiety, preferably via a chemical reaction with a compound carrying a —SH moiety, such that each of the components of the polymeric carrier carries at least one such —SH moiety. Such a compound carrying a —SH moiety may be e.g. an (additional) cysteine or any further (modified) amino acid or compound of the component of the polymeric carrier, which carries a —SH moiety. Such a compound may also be any non-amino compound or moiety, which contains or allows to introduce a —SH moiety into the component as defined herein. Such non-amino compounds may be attached to the component of the polymeric carrier according to the present invention via chemical reactions or binding of compounds, e.g. by binding of a 3-thio propionic acid or 2-iminothiolane (Traut's reagent), by amide formation (e.g. carboxylic acids, sulphonic acids, amines, etc.), by Michael addition (e.g. maleinimide moieties, α,β unsaturated carbonyls, etc.), by click chemistry (e.g. azides or alkines), by alkene/alkine methatesis (e.g. alkenes or alkines), imine or hydrozone formation (aldehydes or ketons, hydrazine, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components. In some cases the —SH moiety may be masked by protecting groups during chemical attachment to the component. Such protecting groups are known in the art and may be removed after chemical coupling. In each case, the —SH moiety, e.g. of a cysteine or of any further (modified) amino acid or compound, may be present at the terminal ends or internally at any position of the component of the polymeric carrier. As defined herein, each of the components of the polymeric carrier typically exhibits at least one —SH-moiety, but may also contain two, three, four, five, or even more —SH-moieties. Additionally to binding of cationic components a —SH moiety may be used to attach further components of the polymeric carrier of the inventive vaccine as defined herein, particularly an amino acid component, e.g. antigen epitopes, antigens, antibodies, cell penetrating peptides (e.g. TAT), ligands, etc.

As defined above, the polymeric carrier, which may be used to complex the at least one mRNA of the inventive vaccine may be formed by disulfide-crosslinked cationic (or polycationic) components. According to one first alternative, at least one cationic (or polycationic) component of the polymeric carrier, which may be used to complex the at least one mRNA of the inventive vaccine may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10, 5 to 15, 10 to 20 or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier, which may be used to complex the at least one mRNA of the inventive vaccine comprises a cationic or polycationic peptide or protein, the cationic properties of the cationic or polycationic peptide or protein or of the entire polymeric carrier, if the polymeric carrier is entirely composed of cationic or polycationic peptides or proteins, may be determined upon its content of cationic amino acids. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

Preferably, such cationic or polycationic peptides or proteins of the polymeric carrier, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from Drosophila antennapedia), pAntp, pIsl, etc., antimicrobial-derived CPPs e.g. Buforin-2, Bac715-24, SynB, SynB(1), pVEC, hCT-derived peptides, SAP, MAP, PpTG20, Loligomere, FGF, Lactoferrin, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moiety, are selected from, without being restricted thereto, following cationic peptides having the following sum formula (I):

$$\{(Arg)_l;(Lys)_m;(His)_n;(Orn)_o;(Xaa)_x\};$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3Arg_9$, $Arg_9His_3$, $His_3Arg_9His_3$, $His_6Arg_9His_6$, $His_3Arg_4His_3$, $His_6Arg_4His_6$, $TyrSer_2Arg_9Ser_2Tyr$, $(ArgLysHis)_4$, $Tyr(ArgLysHis)_2Arg$, etc.

According to a particular preferred embodiment, such cationic or polycationic peptides or proteins of the polymeric carrier having the empirical sum formula (I) as shown above, may, without being restricted thereto, comprise at least one of the following subgroup of formulae:

$Arg_7$, $Arg_8$, $Arg_9$, $Arg_{10}$, $Arg_{11}$, $Arg_{12}$, $Arg_{13}$, $Arg_{14}$, $Arg_{15-30}$;

$Lys_7$, $Lys_8$, $Lys_9$, $Lys_{10}$, $Lys_{11}$, $Lys_{12}$, $Lys_{13}$, $Lys_{14}$, $Lys_{15-30}$;

$His_7$, $His_8$, $His_9$, $His_{10}$, $His_{11}$, $His_{12}$, $His_{13}$, $His_{14}$, $His_{15-30}$;

$Orn_7$, $Orn_8$, $Orn_9$, $Orn_{10}$, $Orn_{11}$, $Orn_{12}$, $Orn_{13}$, $Orn_{14}$, $Orn_{15-30}$;

According to a further particularly preferred embodiment, cationic or polycationic peptides or proteins of the polymeric carrier, having the empirical sum formula (I) as shown above and which comprise or are additionally modified to comprise at least one —SH moiety, may be preferably selected from, without being restricted thereto, at least one of the following subgroup of formulae. The following formulae (as with empirical formula (I)) do not specify any amino acid order, but are intended to reflect empirical formulae by exclusively specifying the (number of) amino acids as components of the respective peptide. Accordingly, as an example, empirical formula $Arg_{(7-29)}Lys_1$ is intended to mean that peptides falling under this formula contain 7 to 19 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

$Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_2Orn_1$, $Arg_{(2-27)}LyS_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}$, $Arg_2His_{(2-27)}Orn_1$, $Arg_1His_{(2-27)}Orn_2$, $Lys_2His_{(2-27)}Orn_1$, $Lys_1His_{(2-27)}Orn_2$;

$Arg_{(1-26)}Lys_3His_1$, $Arg_{(1-26)}Lys_2His_2$, $Arg_{(1-26)}Lys_3His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_1Lys_{(1-26)}Orn_3$, $Lys_{(1-26)}Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_1His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;

$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_2$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}$, $Arg_2Lys_1His_{(1-26)}Orn_2$, $Arg_2Lys_2His_1Orn_{(1-26)}$, $Arg_1Lys_2His_1Orn_{(1-26)}$, $Arg_1Lys_1His_2Orn_{(1-26)}$;

According to a further particular preferred embodiment, cationic or polycationic peptides or proteins of the polymeric carrier, having the empirical sum formula (I) as shown above and which comprise or are additionally modified to comprise at least one —SH moiety, may be, without being restricted thereto, selected from the subgroup consisting of generic formulas $Arg_7$ (also termed as $R_7$), $Arg_9$ (also termed $R_9$), $Arg_{12}$ (also termed as $R_{12}$).

According to a one further particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (I)) as shown above and which comprise or are additionally modified to comprise at least one —SH moiety, may be, without being restricted thereto, selected from subformula (Ia):

$$\{(Arg)_l;(Lys)_m;(His)_n;(Orn)_o;(Xaa')_x\} \quad \text{formula (Ia)}$$

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_l;(Lys)_m;(His)_n;(Orn)_o(Xaa)_x$ (formula (I)) as shown above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (I)) as shown above, may be, without being restricted thereto, selected from subformula (Ib):

$$Cys^1\{(Arg)_l;(Lys)_m;(His)_n;(Orn)_o;(Xaa)_x\}Cys^2 \quad \text{(formula (Ib))}$$

wherein empirical formula $\{(Arg)_l;(Lys)_m;(His)_n;(Orn)_o;(Xaa)_x\}$ (formula (I)) is as defined herein and forms a core of an amino acid sequence according to (semiempirical) formula (I) and wherein $Cys^1$ and $Cys^2$ are Cysteines proximal to, or terminal to $(Arg)_l;(Lys)_m;(His)_n;(Orn)_o;(Xaa)_x$. Exemplary examples may comprise any of the above sequences flanked by two Cys and following sequences:

```
                                                              (SEQ ID NO. 1)
CysArg₇Cys   Cys-Arg-Arg-Arg-Arg-Arg-Arg-Arg-Cys (SEQ ID NO. 2)
CysArg₈Cys   Cys-Arg-Arg-Arg-Arg-Arg-Arg-Arg-Arg-Cys (SEQ ID NO. 3)
CysArg₉Cys:  Cys-Arg-Arg-Arg-Arg-Arg-Arg-Arg-Arg-Arg-Cys (SEQ ID NO. 4)
CysArg₁₀Cys  Cys-Arg-Arg-Arg-Arg-Arg-Arg-Arg-Arg-Arg-Arg-Cys (SEQ ID NO. 5)
CysArg₁₁Cys  Cys-Arg-Arg-Arg-Arg-Arg-Arg-Arg-Arg-Arg-Arg-Arg-Cys (SEQ ID NO. 6)
CysArg₁₂Cys: Cys-Arg-Arg-Arg-Arg-Arg-Arg-Arg-Arg-Arg-Arg-Arg-Arg-Cys
```

-continued

CysArg₁₃Cys: Cys-Arg-Arg-Arg-Arg-Arg-Arg-Arg-Arg-Arg-Arg-Arg-Arg-Arg-Cys (SEQ ID NO. 7)

CysArg₁₄Cys: Cys-Arg-Arg-Arg-Arg-Arg-Arg-Arg-Arg-Arg-Arg-Arg-Arg-Arg-Arg-Cys (SEQ ID NO. 8)

CysArg₁₅Cys: Cys-Arg-Arg-Arg-Arg-Arg-Arg-Arg-Arg-Arg-Arg-Arg-Arg-Arg-Arg-Arg-Cys (SEQ ID NO. 9)

CysArg₁₆Cys: Cys-Arg-Arg-Arg-Arg-Arg-Arg-Arg-Arg-Arg-Arg-Arg-Arg-Arg-Arg-Arg-Arg-Cys (SEQ ID NO. 10)

CysArg₁₇Cys: Cys-Arg-Arg-Arg-Arg-Arg-Arg-Arg-Arg-Arg-Arg-Arg-Arg-Arg-Arg-Arg-Arg-Arg-Cys (SEQ ID NO. 11)

CysArg₁₈Cys: Cys-Arg-Arg-Arg-Arg-Arg-Arg-Arg-Arg-Arg-Arg-Arg-Arg-Arg-Arg-Arg-Arg-Arg-Arg-Cys (SEQ ID NO. 12)

CysArg₁₉Cys: Cys-Arg-Arg-Arg-Arg-Arg-Arg-Arg-Arg-Arg-Arg-Arg-Arg-Arg-Arg-Arg-Arg-Arg-Arg-Arg-Cys (SEQ ID NO. 13)

CysArg₂₀Cys: Cys-Arg-Arg-Arg-Arg-Arg-Arg-Arg-Arg-Arg-Arg-Arg-Arg-Arg-Arg-Arg-Arg-Arg-Arg-Arg-Arg Cys (SEQ ID NO. 14)

This embodiment may apply to situations, wherein the cationic or polycationic peptide or protein of the polymeric carrier, which may be used to complex the at least one mRNA of the inventive vaccine, e.g. when defined according to empirical formula $(Arg)_l;(Lys)_m;(His)_n;(Orn)_o;(Xaa)_x$ (formula (I)) as shown above, has been modified with at least two cysteines as —SH moieties in the above meaning such that the cationic or polycationic peptide of the inventive polymeric carrier carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (non-peptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier, which may be used to complex the at least one mRNA of the inventive vaccine may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

In the context of the polymeric carrier, the cationic components, which form basis for the polymeric carrier, which may be used to complex the at least one mRNA of the inventive vaccine by disulfide-crosslinkage, may be the same or different from each other. It is also particularly preferred that the polymeric carrier of the present invention comprises mixtures of cationic peptides, proteins or polymers and optionally further components as defined herein, which are crosslinked by disulfide bonds as described herein.

In this context, the inventive polymeric carrier, which may be used to complex the at least one mRNA of the inventive vaccine allows to combine desired properties of different (short) cationic or polycationic peptides, proteins or polymers or other components. The polymeric carrier, e.g., allows to efficiently compact nucleic acids for the purpose of efficient transfection of nucleic acids, for adjuvant therapy, for the purposes of gene therapy, for gene knock-down or others strategies without loss of activity, particularly exhibiting an efficient transfection of a nucleic acid into different cell lines in vitro but particularly transfection in vivo. The polymeric carrier is furthermore not toxic to cells, provides for efficient release of its nucleic acid cargo, is stable during lyophilization and is applicable as immunostimulating agent or adjuvant. In this context the components of the inventive polymeric carrier can be varied in such a way that the cytokine pattern induced can be determined.

In particular, the polymeric carrier formed by disulfide-linked cationic components allows considerably to vary its peptide or polymeric content and thus to modulate its biophysical/biochemical properties, particularly the cationic properties of the polymeric carrier, quite easily and fast, e.g. by incorporating as cationic components the same or different cationic peptide(s) or polymer(s) and optionally adding other components into the polymeric carrier. Even though consisting of quite small non-toxic monomer units the polymeric carrier forms a long cationic binding sequence providing a strong condensation of the mRNA as its nucleic acid cargo and complex stability. Under the reducing conditions of the cytosole (e.g. cytosolic GSH), the complex is rapidly degraded into its (cationic) components, which are further degraded (e.g. oligopeptides). This supports deliberation of the nucleic acid cargo in the cytosol. Due to degradation into small oligopeptides or polymers in the cytosol, no toxicity is observed as known for high-molecular oligopeptides or polymers, e.g. from high-molecular polyarginine.

Accordingly, the polymeric carrier, which may be used to complex the at least one mRNA of the inventive vaccine may comprise different (short) cationic or polycationic peptides, proteins or polymers selected from cationic or polycationic peptides, proteins or (non-peptidic) polymers as defined above, optionally together with further components as defined herein.

Additionally, the polymeric carrier, which may be used to complex the at least one mRNA of the inventive vaccine as defined above, more preferably at least one of the different (short) cationic or polycationic peptides or (non-peptidic) polymers forming basis for the polymeric carrier via disulfide-crosslinking, may be, preferably prior to the disulfide-crosslinking, modified with at least one further component. Alternatively, the polymeric carrier as such may be modified with at least one further component. It may also optionally comprise at least one further component, which typically forms the polymeric carrier disulfide together with the other the (short) cationic or polycationic peptides as defined above via disulfide crosslinking.

To allow modification of a cationic or polycationic peptide or a (non-peptidic) polymer as defined above, each of the components of the polymeric carrier may (preferably already prior to disulfide-crosslinking) also contain at least one further functional moiety, which allows attaching such further components as defined herein. Such functional moieties may be selected from functionalities which allow the attachment of further components, e.g. functionalities as defined herein, e.g. by amide formation (e.g. carboxylic acids, sulphonic acids, amines, etc.), by Michael addition (e.g. maleinimide moieties, α,β unsatured carbonyls, etc.), by click chemistry (e.g. azides or alkines), by alkene/alkine methatesis (e.g. alkenes or alkines), imine or hydrozone formation (aldehydes or ketons, hydrazine, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components.

According to a particularly preferred embodiment, the further component, which may be contained in the polymeric carrier, and which may be used to complex the at least one mRNA of the inventive vaccine or which may be used to modify the different (short) cationic or polycationic peptides or (non-peptidic) polymers forming basis for the polymeric carrier or the biophysical/biochemical properties of the polymeric carrier as defined herein, is an amino acid component (AA). According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents Cysteine and provides for the necessary SH-moiety for a disulfide bond. The SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two cationic polymers). In this case, one —SH moiety is preferably protected in a first step using a protecting group as known in the art, leading to an amino acid component (AA) of formula HS-(AA)-S-protecting group. Then, the amino acid component (AA) may be bound to a further component of the polymeric carrier, to form a first disulfide bond via the non-protected SH moiety. The protected —SH-moiety is then typically deprotected and bound to a further free SH-moiety of a further component of the polymeric carrier to form a second disulfide bond.

Alternatively, the amino acid component (AA) may be provided with other functionalities as already described above for the other components of the polymeric carrier, which allow binding of the amino acid component (AA) to any of components of the polymeric carrier.

Thus, according to the present invention, the amino acid component (AA) may be bound to further components of the polymeric carrier, which may be used to complex the at least one mRNA of the inventive vaccine with or without using a disulfide linkage. Binding without using a disulfide linkage may be accomplished by any of the reactions described above, preferably by binding the amino acid component (AA) to the other component of the polymeric carrier using an amid-chemistry as defined herein. If desired or necessary, the other terminus of the amino acid component (AA), e.g. the N- or C-terminus, may be used to couple another component, e.g. a ligand L. For this purpose, the other terminus of the amino acid component (AA) preferably comprises or is modified to comprise a further functionality, e.g. an alkyn-species (see above), which may be used to add the other component via e.g. click-chemistry. If the ligand is bound via an acid-labile bond, the bond is preferably cleaved off in the endosome and the polymeric carrier presents amino acid component (AA) at its surface.

The amino acid component (AA) may occur as a further component of the polymeric carrier, which may be used to complex the at least one mRNA of the inventive vaccine as defined above, e.g. as a linker between cationic components e.g. as a linker between one cationic peptide and a further cationic peptide, as a linker between one cationic polymer and a further cationic polymer, as a linker between one cationic peptide and a cationic polymer, all preferably as defined herein, or as an additional component of the polymeric carrier, e.g. by binding the amino acid component (AA) to the polymeric carrier or a component thereof, e.g. via side chains, SH-moieties or via further moieties as defined herein, wherein the amino acid component (AA) is preferably accordingly modified.

According to a further and particularly preferred alternative, the amino acid component (AA), may be used to modify the polymeric carrier, particularly the content of cationic components in the polymeric carrier as defined above.

In this context it is preferable, that the content of cationic components in the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 30% to 100%, more preferably in the range of about 50% to 100%, even preferably in the range of about 70% to 100%, e.g. 70, 80, 90 or 100%, or in a range formed by any two of the afore mentioned values, provided, that the content of all components in the polymeric carrier is 100%.

In the context of the present invention, the amino acid component (AA) may be selected from the following alternatives.

According to a first alternative, the amino acid component (AA) may be an aromatic amino acid component (AA). The incorporation of aromatic amino acids or sequences as amino aromatic acid component (AA) into the polymeric carrier of the present invention enables a different (second) binding of the polymeric carrier to the nucleic acid due to interactions of the aromatic amino acids with the bases of the nucleic acid cargo in contrast to the binding thereof by cationic charged sequences of the polymeric carrier molecule to the phosphate backbone. This interaction may occur e.g. by intercalations or by minor or major groove binding. This kind of interaction is not prone to decompaction by anionic complexing partners (e.g. Heparin, Hyaluronic acids) which are found mainly in the extracellular matrix in vivo and is also less susceptible to salt effects.

For this purpose, the amino acids in the aromatic amino acid component (AA) may be selected from either the same or different aromatic amino acids e.g. selected from Trp, Tyr, or Phe. Alternatively, the amino acids (or the entire aromatic amino acid component (AA)) may be selected from following peptide combinations Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr, Tyr-Trp-Tyr-Trp, Trp-Trp-Trp-Trp, Tyr-Tyr-Tyr-Tyr, Trp-Phe, Phe-Phe, Phe-Tyr-Phe, Tyr-Phe-Tyr, Phe-Phe-Phe, Phe-Tyr-Phe-Tyr, Tyr-Phe-Tyr-Phe, Phe-Phe-Phe-Phe, Phe-Trp, Trp-Phe, Phe-Phe, Phe-Trp-Phe, Trp-Phe-Trp, Phe-Trp-Phe-Trp, Trp-Phe-Trp-Phe, or Tyr-Tyr-Tyr-Tyr, etc. (SEQ ID NOs: 15-42). Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the aromatic amino acid component (AA) may be selected from e.g. peptide combinations Cys-Tyr-Cys, Cys-Trp-Cys, Cys-Trp-Tyr-Cys, Cys-Tyr-Trp-Cys, Cys-Trp-Trp-Cys, Cys-Tyr-Tyr-Cys, Cys-Trp-Tyr-Trp-Cys, Cys-Tyr-Trp-Tyr-Cys, Cys-Trp-Trp-Trp-Cys, Cys-Tyr-Tyr-Tyr-Cys, Cys-Trp-Tyr-Trp-Tyr-Cys, Cys-Tyr-Trp-Tyr-Trp-Cys, Cys-Trp-Trp-Trp-Trp-Cys, Cys-Tyr-Tyr-Tyr-Tyr-Cys, Cys-Phe-Cys, Cys-Phe-Tyr-Cys, Cys-Tyr-Phe-Cys, Cys-Phe-Phe-Cys, Cys-Tyr-Tyr-Cys, Cys-Phe-Tyr-Phe-Cys, Cys-Tyr-Phe-Tyr-Cys, Cys-Phe-Phe-Phe-Cys, Cys-Tyr-Tyr-Tyr-Cys, Cys-Phe-Tyr-Phe-Tyr-Cys, Cys-Tyr-Phe-Tyr-Phe-Cys, or Cys-Phe-Phe-Phe-Phe-Cys, Cys-Phe-Trp-Cys, Cys-Trp-Phe-Cys, Cys-Phe-Phe-Cys, Cys-Phe-Trp-Phe-Cys, Cys-Trp-Phe-Trp-Cys, Cys-Phe-Trp-Phe-Trp-Cys, Cys-Trp-Phe-Trp-Phe-Cys, etc. Each Cys above may also be replaced by any modified peptide or chemical compound carrying a free —SH-moiety as defined herein. (SEQ ID NOs: 43-75). Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or represent at least one proline, which may serve as a structure breaker of longer sequences of Trp, Tyr and Phe in the aromatic amino acid component (AA), preferably two, three or more prolines.

According to a second alternative, the amino acid component (AA) may be a hydrophilic (and preferably non charged polar) amino acid component (AA). The incorporation of hydrophilic (and preferably non charged polar) amino acids or sequences as amino hydrophilic (and preferably non charged polar) acid component (AA) into the polymeric carrier of the present invention enables a more flexible binding to the nucleic acid cargo. This leads to a more effective compaction of the nucleic acid cargo and hence to a better protection against nucleases and unwanted decompaction. It also allows provision of a (long) polymeric carrier which exhibits a reduced cationic charge over the entire carrier and in this context to better adjusted binding properties, if desired or necessary.

For this purpose, the amino acids in the hydrophilic (and preferably non charged polar) amino acid component (AA) may be selected from either the same or different hydrophilic (and preferably non charged polar) amino acids e.g. selected from Thr, Ser, Asn or Gln. Alternatively, the amino acids (or the entire hydrophilic (and preferably non charged polar)

amino acid component (AA)) may be selected from following peptide combinations Ser-Thr, Thr-Ser, Ser-Ser, Thr-Thr, Ser-Thr-Ser, Thr-Ser-Thr, Ser-Ser-Ser, Thr-Thr-Thr, Thr-Ser-Thr, Thr-Ser-Thr-Ser, Ser-Ser-Ser-Ser, Thr-Thr-Thr-Thr, Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn, Asn-Gln-Asn-Gln, Gln-Gln-Gln-Gln, Asn-Asn-Asn-Asn, Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn, Asn-Ser-Asn-Ser, Ser-Ser-Ser-Ser, or Asn-Asn-Asn-Asn, etc. (SEQ ID NOs: 76-111) Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the hydrophilic (and preferably non-charged polar) amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the hydrophilic (and preferably non-charged polar) amino acid component (AA) may be selected from e.g. peptide combinations Cys-Thr-Cys, Cys-Ser-Cys, Cys-Ser-Thr-Cys, Cys-Thr-Ser-Cys, Cys-Ser-Ser-Cys, Cys-Thr-Thr-Cys, Cys-Ser-Thr-Ser-Cys, Cys-Thr-Ser-Thr-Cys, Cys-Ser-Ser-Ser-Cys, Cys-Thr-Thr-Thr-Cys, Cys-Ser-Thr-Ser-Thr-Cys, Cys-Thr-Ser-Thr-Ser-Cys, Cys-Ser-Ser-Ser-Ser-Cys, Cys-Thr-Thr-Thr-Thr-Cys, Cys-Asn-Cys, Cys-Gln-Cys, Cys-Gln-Asn-Cys, Cys-Asn-Gln-Cys, Cys-Gln-Gln-Cys, Cys-Asn-Asn-Cys, Cys-Gln-Asn-Gln-Cys, Cys-Asn-Gln-Asn-Cys, Cys-Gln-Gln-Gln-Cys, Cys-Asn-Asn-Asn-Cys, Cys-Gln-Asn-Gln-Asn-Cys, Cys-Asn-Gln-Asn-Gln-Cys, Cys-Gln-Gln-Gln-Gln-Cys, Cys-Asn-Asn-Asn-Asn-Cys, Cys-Asn-Cys, Cys-Ser-Cys, Cys-Ser-Asn-Cys, Cys-Asn-Ser-Cys, Cys-Ser-Ser-Cys, Cys-Asn-Asn-Cys, Cys-Ser-Asn-Ser-Cys, Cys-Asn-Ser-Asn-Cys, Cys-Ser-Ser-Ser-Cys, Cys-Asn-Asn-Asn-Cys, Cys-Ser-Asn-Ser-Asn-Cys, Cys-Asn-Ser-Asn-Ser-Cys, Cys-Ser-Ser-Ser-Ser-Cys, or Cys-Asn-Asn-Asn-Asn-Cys, etc. Each Cys above may also be replaced by any modified peptide or chemical compound carrying a free —SH-moiety as defined herein. (SEQ ID NOs: 112-153) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the hydrophilic (and preferably non-charged polar) amino acid component (AA) may contain at least one proline, which may serve as a structure breaker of longer sequences of Ser, Thr and Asn in the hydrophilic (and preferably non charged polar) amino acid component (AA), preferably two, three or more prolines.

According to a third alternative, the amino acid component (AA) may be a lipophilic amino acid component (AA). The incorporation of lipophilic amino acids or sequences as amino lipophilic acid component (AA) into the polymeric carrier of the present invention enables a stronger compaction of the nucleic acid cargo and/or the polymeric carrier and its nucleic acid cargo when forming a complex. This is particularly due to interactions of one or more polymer strands of the polymeric carrier, particularly of lipophilic sections of lipophilic amino acid component (AA) and the nucleic acid cargo. This interaction will preferably add an additional stability to the complex between the polymeric carrier and its nucleic acid cargo. This stabilization may somehow be compared to a sort of non covalent crosslinking between different polymer strands. Especially in aqueous environment this interaction is typically strong and provides a significant effect.

For this purpose, the amino acids in the lipophilic amino acid component (AA) may be selected from either the same or different lipophilic amino acids e.g. selected from Leu, Val, Ile, Ala, Met. Alternatively, the amino acid AA (or the entire lipophilic amino acid component (AA)) may be selected from following peptide combinations Leu-Val, Val-Leu, Leu-Leu, Val-Val, Leu-Val-Leu, Val-Leu-Val, Leu-Leu-Leu, Val-Val-Val, Leu-Val-Leu-Val, Val-Leu-Val-Leu, Leu-Leu-Leu-Leu, Val-Val-Val-Val, Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala, Ala-Ile-Ala-Ile, Ile-Ile-Ile-Ile, Ala-Ala-Ala-Ala, Met-Ala, Ala-Met, Met-Met, Ala-Ala, Met-Ala-Met, Ala-Met-Ala, Met-Met-Met, Ala-Ala-Ala, Met-Ala-Met-Ala, Ala-Met-Ala-Met, or Met-Met-Met-Met etc. (SEQ ID NOs: 154-188) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain or may be flanked by a —SH containing moiety, which allows introducing this component via a disulfide bond as a further part of the polymeric carrier above, e.g. as a linker. Such a —SH containing moiety may be any moiety as defined herein suitable to couple one component as defined herein to a further component as defined herein. As an example, such a —SH containing moiety may be a cysteine. Then, e.g. the lipophilic amino acid component (AA) may be selected from e.g. peptide combinations Cys-Val-Cys, Cys-Leu-Cys, Cys-Leu-Val-Cys, Cys-Val-Leu-Cys, Cys-Leu-Leu-Cys, Cys-Val-Val-Cys, Cys-Leu-Val-Leu-Cys, Cys-Val-Leu-Val-Cys, Cys-Leu-Leu-Leu-Cys, Cys-Val-Val-Val-Cys, Cys-Leu-Val-Leu-Val-Cys, Cys-Val-Leu-Val-Leu-Cys, Cys-Leu-Leu-Leu-Leu-Cys, Cys-Val-Val-Val-Val-Cys, Cys-Ala-Cys, Cys-Ile-Cys, Cys-Ile-Ala-Cys, Cys-Ala-Ile-Cys, Cys-Ile-Ile-Cys, Cys-Ala-Ala-Cys, Cys-Ile-Ala-Ile-Cys, Cys-Ala-Ile-Ala-Cys, Cys-Ile-Ile-Ile-Cys, Cys-Ala-Ala-Ala-Cys, Cys-Ile-Ala-Ile-Ala-Cys, Cys-Ala-Ile-Ala-Ile-Cys, Cys-Ile-Ile-Ile-Ile-Cys, or Cys-Ala-Ala-Ala-Ala-Cys, Cys-Met-Cys, Cys-Met-Ala-Cys, Cys-Ala-Met-Cys, Cys-Met-Met-Cys, Cys-Ala-Ala-Cys, Cys-Met-Ala-Met-Cys, Cys-Ala-Met-Ala-Cys, Cys-Met-Met-Met-Cys, Cys-Ala-Ala-Ala-Cys, Cys-Met-Ala-Met-Ala-Cys, Cys-Ala-Met-Ala-Met-Cys, Cys-Met-Met-Met-Met-Cys, or Cys-Ala-Ala-Ala-Ala-Cys, etc. Each Cys above may also be replaced by any modified peptide or chemical compound carrying a free —SH-moiety as defined herein. (SEQ ID NOs: 189-229) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain at least one proline, which may serve as a structure breaker of longer sequences of Leu, Val, Ile, Ala and Met in the lipophilic amino acid component (AA), preferably two, three or more prolines.

Finally, according to a fourth alternative, the amino acid component (AA) may be a weak basic amino acid component (AA). The incorporation of weak basic amino acids or sequences as weak basic amino acid component (AA) into the polymeric carrier of the present invention may serve as a proton sponge and facilitates endosomal escape (also called endosomal release) (proton sponge effect). Incorporation of such a weak basic amino acid component (AA) preferably enhances transfection efficiency.

For this purpose, the amino acids in the weak basic amino acid component (AA) may be selected from either the same or different weak amino acids e.g. selected from histidine or aspartate (aspartic acid). Alternatively, the weak basic amino acids (or the entire weak basic amino acid component (AA)) may be selected from following peptide combinations Asp-His, His-Asp, Asp-Asp, His-His, Asp-His-Asp, His-Asp-His, Asp-Asp-Asp, His-His-His, Asp-His-Asp-His, His-Asp-His-Asp, Asp-Asp-Asp-Asp, or His-His-His-His, etc. (SEQ ID NOs: 230-241) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the weak basic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the weak basic amino acid component (AA) may be selected from e.g. peptide combinations Cys-His-Cys, Cys-Asp-Cys, Cys-Asp-His-Cys, Cys-His-Asp-Cys, Cys-Asp-Asp-Cys, Cys-His-His-Cys, Cys-Asp-His-Asp-Cys, Cys-His-Asp-His-Cys, Cys-Asp-Asp-Asp-Cys, Cys-His-His-His-Cys, Cys-Asp-His-Asp-His-Cys, Cys-His-Asp-His-Asp-Cys, Cys-Asp-Asp-Asp-Asp-Cys, or Cys-His-His-His-His-Cys, etc. Each Cys above may also be replaced by any modified peptide or chemical compound carrying a free —SH-moiety as defined herein. (SEQ ID NOs: 242-255) Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the weak basic amino acid component (AA) may contain at least one proline, which may serve as a structure breaker of longer sequences of histidine or aspartate (aspartic acid) in the weak basic amino acid component (AA), preferably two, three or more prolines.

According to a fifth alternative, the amino acid component (AA) may be a signal peptide or signal sequence, a localisation signal or sequence, a nuclear localisation signal or sequence (NLS), an antibody, a cell penetrating peptide, (e.g. TAT), etc. Preferably such an amino acid component (AA) is bound to the polymeric carrier or to another component of the polymeric carrier via a (reversible) disulfide bond. In this context the signal peptide or signal sequence, a localisation signal or sequence, a nuclear localisation signal or sequence (NLS), an antibody, a cell penetrating peptide, (e.g. TAT), etc.; additionally comprises at least one —SH-moiety. In this context a signal peptide, a localisation signal or sequence or a nuclear localisation signal or sequence (NLS), may be used to direct the inventive polymeric carrier cargo complex to specific target cells (e.g. hepatocytes or antigen-presenting cells) and preferably allows a translocalisation of the polymeric carrier to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytoskeleton, etc. Such signal peptide, a localisation signal or sequence or a nuclear localisation signal may be used for the transport of any of the herein defined nucleic acids, preferably an RNA or a DNA, more preferably an shRNA or a pDNA, e.g. into the nucleus. Without being limited thereto, such a signal peptide, a localisation signal or sequence or a nuclear localisation signal may comprise, e.g., localisation sequences for the endoplasmic reticulum. Particular localisation signals or sequences or a nuclear localisation signals may include e.g. KDEL (SEQ ID NO: 256), DDEL (SEQ ID NO: 257), DEEL (SEQ ID NO: 258), QEDL (SEQ ID NO: 259), RDEL (SEQ ID NO: 260), and GQNLSTSN (SEQ ID NO: 261), nuclear localisation sequences, including PKKKRKV (SEQ ID NO: 262), PQKKIKS (SEQ ID NO: 263), QPKKP (SEQ ID NO: 264), RKKR (SEQ ID NO: 265), RKKRRQRRRAHQ (SEQ ID NO: 266), RQARRNRRRRWRERQR (SEQ ID NO: 267), MPLTRRRPAASQALAPPTP (SEQ ID NO: 268), GAALTILV (SEQ ID NO: 269), and GAALTLLG (SEQ ID NO: 270), localisation sequences for the endosomal compartment, including MDDQRDLISNNEQLP (SEQ ID NO: 271), localisation sequences for the mitochondrial matrix, including MLFNLRXXLNNAAFRHGHNFMVRN-FRCGQPLX (SEQ ID NO: 272), localisation sequences for the plasma membrane: GCVCSSNP (SEQ ID NO: 273), GQTVTTPL (SEQ ID NO: 274), GQELSQHE (SEQ ID NO: 275), GNSPSYNP (SEQ ID NO: 276), GVSGSKGQ (SEQ ID NO: 277), GQTITTPL (SEQ ID NO: 278), GQTLTTPL (SEQ ID NO: 279), GQIFSRSA (SEQ ID NO: 280), GQIHGLSP (SEQ ID NO: 281), GARASVLS (SEQ ID NO: 282), and GCTLSAEE (SEQ ID NO: 283), localisation sequences for the endoplasmic reticulum and the nucleus, including GAQVSSQK (SEQ ID NO: 284), and GAQLSRNT (SEQ ID NO: 285), localisation sequences for the Golgi apparatus, the nucleus, the cytoplasm and the cytoskeleton, including GNAAAAKK (SEQ ID NO: 286), localisation sequences for the cytoplasm and cytoskeleton, including GNEASYPL (SEQ ID NO: 287), localisation sequences for the plasma membrane and cytoskeleton, including GSSKSKPK (SEQ ID NO: 288), etc. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention. Such an additional component may be bound e.g. to a cationic polymer or to any other component of the polymeric carrier as defined herein. Preferably this signal peptide, localisation signal or sequence or nuclear localisation signal or sequence (NLS), is bound to the polymeric carrier or to another component of the polymeric carrier via a (reversible) disulfide bond. For this purpose the (AA) component additionally comprises at least one —SH moiety as defined herein. The binding to any of components of the polymeric carrier may also be accomplished using an acid-labile bond, preferably via a side chain of any of components of the polymeric carrier, which allows to detach or release the additional component at lower pH-values, e.g. at physiological pH-values as defined herein.

Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined below as therapeutically active proteins. According to one alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the polymeric carrier (in complex with a nucleic acid) from the endosome by insertion into the lipid layer of the liposome. These cell penetrating peptides (CPPs) or cationic peptides for transportation, may include, without being limited thereto protamine, nucleoline, spermine or spermidine, oligo- or poly-L-lysine (PLL), basic polypeptides, oligo or polyarginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, *Antennapedia*-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, Pestivirus Ems, HSV, VP22 (Herpes simplex), MAP, KALA or protein transduction domains (PTDs, PpT620, prolinerich peptides, arginine-rich peptides, lysine-rich peptides, Pep-1, L-oligomers, Calcitonin peptide(s), etc. Such an amino acid component (AA) may also be bound to any component of the polymeric carrier as defined herein. Preferably it is bound to the polymeric carrier or to another component of the polymeric carrier via a (reversible) disulfide bond. For the above purpose, the amino acid component (AA) preferably comprises at least one —SH moiety as defined herein. The binding to any of components of the polymeric carrier may also be accomplished using an SH-moiety or an acid-labile bond, preferably via a side chain of any of components of the polymeric carrier which allows to detach or release the additional component at lower pH-values, e.g. at physiological pH-values as defined herein.

According to a last alternative, the amino acid component (AA) may consist of any peptide or protein which can execute any favourable function in the cell. Particularly preferred are peptides or proteins selected from therapeutically active proteins or peptides, from antigens, e.g. tumour antigens, pathogenic antigens (animal antigens, viral antigens, protozoan antigens, bacterial antigens, allergic antigens), autoimmune antigens, or further antigens, from allergens, from antibodies, from immunostimulatory proteins or peptides, from antigen-specific T cell receptors, or from any other protein or peptide suitable for a specific (therapeutic) application as defined below for coding nucleic acids. Particularly preferred are peptide epitopes from antigens as defined herein.

The polymeric carrier, which may be used to complex the at least one mRNA of the inventive vaccine may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

According to another aspect, the polymeric carrier, which may be used to complex the at least one mRNA of the inventive vaccine or single components thereof, e.g. of the above mentioned cationic or polycationic peptides, proteins or polymers or further components, e.g. (AA), may be further modified with a ligand, preferably a carbohydrate, more preferably a sugar, even more preferably mannose. Preferably this ligand is bound to the polymeric carrier or to a component of the polymeric carrier via a (reversible) disulfide bond or via Michael addition. In the case that the ligand is bound by a disulfide bond the ligand additionally comprises at least one —SH-moiety. These ligands may be used to direct the inventive polymeric carrier cargo complex to specific target cells (e.g. hepatocytes or antigen-presenting cells). In this context mannose is particularly preferred as ligand in the case that dendritic cells are the target especially for vaccination or adjuvant purposes.

According to one specific aspect, the entire inventive polymeric carrier may be formed by a polymerization condensation (of at least one) of the above mentioned cationic or polycationic peptides, proteins or polymers or further components, e.g. (AA), via their —SH-moieties in a first step and complexing the nucleic acid to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific aspect, the inventive polymeric carrier, which may be used to complex the at least one mRNA of the inventive vaccine is formed by carrying out the polymerization condensation of at least one of the above mentioned cationic or polycationic peptides, proteins or polymers or further components, e.g. (AA), via their —SH-moieties simultaneously to complexing the at least one mRNA encoding the at least one antigen to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

According to a further alternative aspect, the inventive polymeric carrier may be selected from a polymeric carrier molecule according to generic formula (VI):

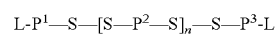

wherein,

P$^1$ and P$^3$ are different or identical to each other and represent a linear or branched hydrophilic polymer chain, each P$^1$ and P$^3$ exhibiting at least one —SH-moiety, capable to form a disulfide linkage upon condensation with component P$^2$, or alternatively with (AA), (AA)$_x$, or [(AA)$_x$]$_z$ if such components are used as a linker between P$^1$ and P$^2$ or P$^3$ and P$^2$) and/or with further components (e.g. (AA), (AA)$_x$, [(AA)$_x$]$_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethylstarch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;

P$^2$ is a cationic or polycationic peptide or protein, e.g. as defined herein, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined herein, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), (AA)$_x$, or [(AA)]$_z$);

—S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), (AA)$_x$, [(AA)$_x$]$_z$, etc); The —SH-moiety may be part of the structure of these components or added by a modification as defined below;

L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues) etc.;

n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

As defined above, ligands (L), may be optionally used in the inventive polymeric carrier molecule according to generic formula (VI), e.g. for direction of the inventive carrier polymer and its entire "cargo" (the adjuvant component and/or the antigen of the inventive composition or vaccine composition) into specific cells. They may be selected independent from the other from RGD, Transferrin, Folate, a signal peptide or signal sequence, a localization signal or sequence, a nuclear localization signal or sequence (NLS), an antibody, a cell penetrating peptide (CPP), (e.g. TAT, KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues) or any such molecule as further defined below, etc. Particularly preferred are cell penetrating peptides (CPPs), which induce a pH-mediated conformational change in the endosome and lead to an improved release of the inventive polymeric carrier (in complex with a nucleic acid) from the endosome by insertion into the lipid layer of the liposome. Such called CPPs or cationic peptides for transportation, may include, without being limited thereto protamine, nucleoline, spermine or spermidine, poly-L-lysine (PLL), basic polypeptides, polyarginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, *Antennapedia*-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, Pestivirus Erns, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc. Particularly preferred in this context is mannose as ligand to target antigen presenting cells which carries on their cell membrane mannose receptors. In a further preferred aspect of the first embodiment of the present invention galactose as optional ligand can be used to target hepatocytes. Such ligands may be attached to component $P^1$ and/or $P^3$ by reversible disulfide bonds as defined below or by any other possible chemical attachment, e.g. by amide formation (e.g. carboxylic acids, sulphonic acids, amines, etc), by Michael addition (e.g. maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components.

In the context of formula (VI) of the present invention components $P^1$ and $P^3$ represent a linear or branched hydrophilic polymer chain, containing at least one —SH-moiety, each $P^1$ and $P^3$ independently selected from each other, e.g. from polyethylene glycol (PEG), poly-N-(2-hydroxypropyl) methacrylamide, poly-2-(methacryloyloxy)ethyl phosphorylcholines, poly(hydroxyalkyl L-asparagine) or poly(hydroxyalkyl L-glutamine). $P^1$ and $P^3$ may be identical or different to each other. Preferably, each of hydrophilic polymers $P^1$ and $P^3$ exhibits a molecular weight of about 1 kDa to about 100 kDa, preferably of about 1 kDa to about 75 kDa, more preferably of about 5 kDa to about 50 kDa, even more preferably of about 5 kDa to about 25 kDa. Additionally, each of hydrophilic polymers $P^1$ and $P^3$ typically exhibits at least one —SH-moiety, wherein the at least one —SH-moiety is capable to form a disulfide linkage upon reaction with component $P^2$ or with component (AA) or (AA)$_x$, if used as linker between $P^1$ and $P^2$ or $P^3$ and $P^2$ as defined below and optionally with a further component, e.g. L and/or (AA) or (AA)$_x$, e.g. if two or more —SH-moieties are contained. The following subformulae "$P^1$—S—S—$P^2$" and "$P^2$—S—S—$P^3$" within generic formula (VI) above (the brackets are omitted for better readability), wherein any of S, $P^1$ and $P^3$ are as defined herein, typically represent a situation, wherein one —SH-moiety of hydrophilic polymers $P^1$ and $P^3$ was condensed with one —SH-moiety of component $P^2$ of generic formula (VI) above, wherein both sulphurs of these —SH-moieties form a disulfide bond —S—S— as defined herein in formula (VI). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH— moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "-Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g. maleinimide moieties, $\alpha,\beta$ unsaturated carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow $S_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

According to one preferred alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the inventive polymeric carrier (in complex with a nucleic acid) from the endosome by insertion into the lipid layer of the liposome. Such called cell penetrating peptides (CPPs) or cationic peptides for transportation, may include, without being limited thereto protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, *Antennapedia*-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, Pestivirus Ems, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

According to a further preferred aspect of the first embodiment of the present invention, each of hydrophilic polymers $P^1$ and $P^3$ of formula (VI) of the polymeric carrier used according to the present invention may also contain at least one further functional moiety, which allows attaching further components as defined herein, e.g. a ligand as defined above, or functionalities which allow the attachment of further components, e.g. by amide formation (e.g. carboxylic acids, sulphonic acids, amines, etc), by Michael addition (e.g. maleinimide moieties, $\alpha,\beta$ unsaturated carbonyls, etc), by click chemistry (e.g. azides or alkines), by alkene/alkine methatesis (e.g. alkenes or alkines), imine or hydrozone formation (aldehydes or ketons, hydrazine, hydroxylamins, amines), complexation reactions (avidin, biotin, protein G) or components which allow S-type substitution reactions (e.g. halogenalkans, thiols, alcohols, amines, hydrazines, hydrazides, sulphonic acid esters, oxyphosphonium salts) or other chemical moieties which can be utilized in the attachment of further components. Further functional moieties may comprise an amino acid component (AA) as defined herein or $(AA)_x$, wherein (AA) is preferably an amino component as defined above. In the above context, x is preferably an integer and may be selected from a range of about 1 to 100, preferably from a range of about 1 to 50, more preferably 1 to 30, and even more preferably selected from a number comprising 1, 2, 3, 4, 5, 6, 7, 8, 9, 10, 11, 12, 13, 14 or 15-30, e.g. from a range of about 1 to 30, from a range of about 1 to 15, or from a number comprising 1, 2, 3, 4, 5, 6, 7, 8, 9, 10, 11, 12, 13, 14 or 15, or may be selected from a range formed by any two of the afore mentioned values. Most preferably, x is 1. Such an amino acid component (AA) or $(AA)_x$ may be contained in every part of the inventive polymeric carrier according to formula (VI) above and therefore may be attached to all components of the inventive polymeric carrier according to formula (VI). It is particularly preferred that amino acid component (AA) or $(AA)_x$ is present as a ligand or part of the repetitive component $[S—P^2—S]_n$ within formula (VI) of the inventive polymeric carrier.

In the context of the entire formula (VI) of the inventive polymeric carrier may be preferably defined as follows:

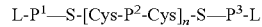

wherein L, $P^1$, $P^2$, $P^3$ and n are as defined herein, S is sulphur and each Cys provides for one —SH-moiety for the disulfide bond.

According to a particular aspect, the inventive polymeric carrier according to formula (VI) as defined above, may comprise at least one amino acid component (AA) or (AA)$_x$, as defined above. Such an amino acid component (AA) or (AA)$_x$ may be contained in every part of the inventive polymeric carrier according to formula (VI) above and therefore may be attached to all components of the inventive polymeric carrier according to formula (VI). It is particularly preferred that amino acid component (AA) or (AA)$_x$ is present as a ligand or part of the repetitive component [S—P$^2$—S]$_n$ within formula (VI) of the inventive polymeric carrier. The amino acid component (AA) or (AA)$_x$ preferably contains or is flanked (e.g. terminally) by at least one —SH containing moiety, which allows introducing this component (AA) or (AA)$_x$ via a disulfide bond into the polymeric carrier according to formula (VI) as defined herein. Such a —SH-containing moiety may be any —SH containing moiety (or, of course, one sulphur of a disulfide bond), e.g. a cysteine residue. In the specific case that the —SH containing moiety represents a cysteine, the amino acid component (AA) may also be read as -Cys-(AA)$_x$- or -Cys-(AA)$_x$-Cys- wherein Cys represents Cysteine and provides for the necessary —SH-moiety for a disulfide bond. The —SH containing moiety may be also introduced into the amino acid component (AA)$_x$ using any of modifications or reactions as shown above for components P$^1$, P$^2$ or P$^3$. In the specific case that the amino acid component (AA)$_x$ is linked to two components of the inventive polymeric carrier according to formula (VI) it is preferred that (AA) or (AA)$_x$ contains at least two —SH-moieties, e.g. at least two Cysteines, preferably at its terminal ends. This is particularly preferred if (AA) or (AA)$_x$ is part of the repetitive component [S—P$^2$—S]$_n$. Alternatively, the amino acid component (AA) or (AA)$_x$ is introduced into the inventive polymeric carrier according to formula (VI) as defined herein via any chemical possible addition reaction. Therefore the amino acid component (AA) or (AA)$_x$ contains at least one further functional moiety, which allows attaching same to a further component as defined herein, e.g. component P$^1$ or P$^3$, P$^2$, L, or a further amino acid component (AA) or (AA)$_x$, etc. Such functional moieties may be selected from functionalities which allow the attachment of further components, e.g. functionalities as defined herein, e.g. by amide formation (e.g. carboxylic acids, sulphonic acids, amines, etc), by Michael addition (e.g. maleinimide moieties, α,β unsaturated carbonyls, etc), by click chemistry (e.g. azides or alkines), by alkene/alkine methatesis (e.g. alkenes or alkines), imine or hydrozone formation (aldehydes or ketons, hydrazine, hydroxylamins, amines), complexation reactions (avidin, biotin, protein G) or components which allow S$_n$-type substitution reactions (e.g. halogenalkans, thiols, alcohols, amines, hydrazines, hydrazides, sulphonic acid esters, oxyphosphonium salts) or other chemical moieties which can be utilized in the attachment of further components.

The amino acid component (AA) or (AA)$_x$ in the polymeric carrier of formula (VI) may also occur as a mixed repetitive amino acid component [(AA)$_x$]$_z$, wherein the number of amino acid components (AA) or (AA)$_x$ is further defined by integer z. In this context, z may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values.

According to a specific and particularly preferred alternative, the amino acid component (AA) or (AA)$_x$, preferably written as S-(AA)$_x$-S or [S-(AA)$_x$-S] may be used to modify component P$^2$, particularly the content of component S—P$^2$—S in repetitive component [S—P$^2$—S]$_n$ of the polymeric carrier of formula (VI) above. This may be represented in the context of the entire polymeric carrier according to formula (VI) e.g. by following formula (VIa):

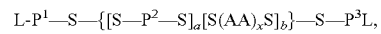

wherein x, S, L, AA, P$^1$, P$^2$ and P$^3$ are preferably as defined herein. In formula (VIa) above, any of the single components [S—P$^2$—S] and [S-(AA)$_x$-S] may occur in any order in the subformula {[S—P$^2$—S]$_a$[S-(AA)-S]$_b$}. The numbers of single components [S—P$^2$—S] and [S-(AA)$_x$-S] in the subformula {[S—P$^2$—S]$_a$[S-(AA)$_x$-S]$_b$} are determined by integers a and b, wherein a+b=n. n is an integer and is defined as above for formula (VI).

a is an integer, typically selected independent from integer b from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, a is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

b is an integer, typically selected independent from integer a from a range of about 0 to 50 or 1 to 50, preferably from a range of about 0, 1, 2 or 3 to 30, more preferably from a range of about 0, 1, 2, 3, 4, or 5 to 25, or a range of about 0, 1, 2, 3, 4, or 5 to 20, or a range of about 0, 1, 2, 3, 4, or 5 to 15, or a range of about 0, 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, b is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

According to one preferred aspect, the mRNA of the inventive vaccine encoding at least one antigen as defined above may be formulated together with a cationic or polycationic compound and/or with a polymeric carrier, preferably as defined herein.

According to a further preferred aspect, the mRNA of the inventive vaccine encoding at least one antigen as defined above may be formulated together with an (adjuvant) component. According to a particularly preferred aspect, the mRNA of the inventive vaccine encoding at least one antigen as defined above may be formulated to comprise a) an (adjuvant) component, comprising or consisting of at least one immunostimulatory nucleic acid, complexed with a cationic or polycationic compound and/or with a polymeric carrier, preferably as defined herein, and b) at least one free mRNA, encoding an antigen, preferably as defined herein for the inventive vaccine.

In the above context, a cationic or polycationic compound and/or a polymeric carrier used to complex the at least one immunostimulatory nucleic acid in the adjuvant component, may be selected from a cationic or polycationic compound and/or a polymeric carrier as defined above.

Furthermore, an immunostimulatory nucleic acid as defined above for the adjuvant component may be preferably selected from an mRNA as defined herein for the inventive vaccine, encoding at least one antigen. Alternatively, such an immunostimulatory nucleic acid may be selected from an immunostimulatory nucleic acid, as defined herein, preferably an immunostimulatory RNA (is RNA) as defined herein.

In this context, an immunostimulatory nucleic acid, as used herein, is preferably selected from immunostimulatory nucleic acids which are known to bind to TLR receptors. Such an immunostimulatory nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (ds-DNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

Furthermore, an immunostimulatory nucleic acid, as used herein, is preferably selected from an immunostimulatory RNA (is RNA), which preferably elicits an innate immune response. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) (single-stranded) non-coding RNA. In this context it is particular preferred that the is RNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T cells. Th2 cells, on the other hand, promote the humoral immune response by stimulation of B cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl. Acad. Sci. USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc.

Preferably, an immunostimulatory nucleic acid, preferably an immunostimulatory RNA (is RNA), as used herein, may comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell. 22, 561-569), or any other immunostimulatory RNA sequence. Furthermore, (classes of) immunostimulatory RNA molecules, used as a further compound of the inventive vaccine, may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, an immunostimulatory nucleic acid sequence, particularly an is RNA, as used herein, may consist of or comprise a nucleic acid of formula (I) or (II):

$$G_l X_m G_n, \qquad \text{(formula (I))}$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
   wherein
   when l=1 G is guanosine or an analogue thereof,
   when l>1 at least 50% of the nucleotides are guanosine or an analogue thereof;
m is an integer and is at least 3;
   wherein
   when m=3 X is uracil or an analogue thereof,
   when m>3 at least 3 successive uracils or analogues of uracil occur;
n is an integer from 1 to 40,
   wherein
   when n=1 G is guanosine or an analogue thereof,
   when n>1 at least 50% of the nucleotides are guanosine or an analogue thereof.

$$C_l X_m C_n, \qquad \text{(formula (II))}$$

wherein:
C is cytosine, uracil or an analogue of cytosine or uracil;
X is guanosine, uracil, adenosine, thymidine, cytosine or an analogue of the above-mentioned nucleotides;

l is an integer from 1 to 40,
wherein
when l=1 C is cytosine or an analogue thereof,
when l>1 at least 50% of the nucleotides are cytosine or an analogue thereof
m is an integer and is at least 3;
wherein
when m=3 X is uracil or an analogue thereof,
when m>3 at least 3 successive uracils or analogues of uracil occur;
n is an integer from 1 to 40,
wherein
when n=1 C is cytosine or an analogue thereof,
when n>1 at least 50% of the nucleotides are cytosine or an analogue thereof.

The nucleic acids of formula (I) or (II), which may be used as an immunostimulatory nucleic acid sequence, particularly an isRNA, may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of formula (I) or (II) has a maximum length of e.g. 100 nucleotides, m will typically be <=98. The number of nucleotides G in the nucleic acid of formula (I) is determined by l or n. l and n, independently of one another, are each an integer from 1 to 40, wherein when l or n=1 G is guanosine or an analogue thereof, and when l or n>1 at least 50% of the nucleotides are guanosine or an analogue thereof. For example, without implying any limitation, when l or n=4 $G_1$ or $G_n$ can be, for example, a GUGU, GGUU, UGUG, UUGG, GUUG, GGGU, GGUG, GUGG, UGGG or GGGG, etc.; when l or n=5 $G_1$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (I) according to the invention is preferably not a uracil. Similarly, the number of nucleotides C in the nucleic acid of formula (II) according to the invention is determined by l or n. l and n, independently of one another, are each an integer from 1 to 40, wherein when l or n=1 C is cytosine or an analogue thereof, and when l or n>1 at least 50% of the nucleotides are cytosine or an analogue thereof. For example, without implying any limitation, when l or n=4, $C_1$ or $C_n$, can be, for example, a CUCU, CCUU, UCUC, UUCC, CUUC, CCCU, CCUC, CUCC, UCCC or CCCC, etc.; when l or n=5 $C_1$ or $C_n$, can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (II) according to the invention is preferably not a uracil. Preferably, for formula (I), when l or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_1$ and/or $G_n$ are uracil or an analogue thereof, as defined hereinbefore. Also preferably, l and n, independently of one another, are each an integer from 2 to 30, more preferably an integer from 2 to 20 and yet more preferably an integer from 2 to 15. The lower limit of l or n can be varied if necessary and is at least 1, preferably at least 2, more preferably at least 3, 4, 5, 6, 7, 8, 9 or 10. This definition applies correspondingly to formula (II).

According to a particularly preferred embodiment, a nucleic acid according to any of formulas (I) or (II) above, which may be used as an immunostimulatory nucleic acid sequence, particularly an isRNA, may be selected from a sequence consisting or comprising any of the following sequences:

GGUUUUUUUUUUUUUUUGGG; (SEQ ID NO: 289)

GGGGGUUUUUUUUUUGGGGG; (SEQ ID NO: 290)

GGGGGUUUUUUUUUUUUUUUUUUUUUUUUUUUGGGGG; (SEQ ID NO: 291)

GUGUGUGUGUGUUUUUUUUUUUUUUGUGUGUGUGUGU; (SEQ ID NO: 292)

GGUUGGUUGGUUUUUUUUUUUUUUUUGGUUGGUUGGUU; (SEQ ID NO: 293)

GGGGGGGGGUUUGGGGGGGG; (SEQ ID NO: 294)

GGGGGGGGGUUUGGGGGGGG; (SEQ ID NO: 295)

GGGGGGGUUUUUGGGGGGG; (SEQ ID NO: 296)

GGGGGGGUUUUUUGGGGGG; (SEQ ID NO: 297)

GGGGGGUUUUUUUGGGGGG; (SEQ ID NO: 298)

GGGGGGUUUUUUUGGGGGG; (SEQ ID NO: 299)

GGGGGGUUUUUUUUGGGGG; (SEQ ID NO: 300)

GGGGGUUUUUUUUUGGGGG; (SEQ ID NO: 301)

GGGGGUUUUUUUUUUUGGG; (SEQ ID NO: 302)

GGGUUUUUUUUUUUUUGGG; (SEQ ID NO: 303)

GGGGUUUUUUUUUUUUUGG; (SEQ ID NO: 304)

GGUUUUUUUUUUUUUUUGG; (SEQ ID NO: 305)

GUUUUUUUUUUUUUUUUUG; (SEQ ID NO: 306)

GGGGGGGGGUUUGGGGGGGGG; (SEQ ID NO: 307)

GGGGGGGGGUUUGGGGGGGGG; (SEQ ID NO: 308)

GGGGGGGGGUUUGGGGGGGGG; (SEQ ID NO: 309)

GGGGGGGGGUUUUUGGGGGGGG; (SEQ ID NO: 310)

GGGGGGGUUUUUUUGGGGGGG; (SEQ ID NO: 311)

-continued

GGGGGGGUUUUUUUUUGGGGGG; (SEQ ID NO: 312)

GGGGGGGUUUUUUUUUUGGGGG; (SEQ ID NO: 313)

GGGGGGUUUUUUUUUUGGGGG; (SEQ ID NO: 314)

GGGGGGUUUUUUUUUUUGGGG; (SEQ ID NO: 315)

GGGGGUUUUUUUUUUUUGGGG; (SEQ ID NO: 316)

GGGGGUUUUUUUUUUUUUGGG; (SEQ ID NO: 317)

GGGUUUUUUUUUUUUUUUGGG; (SEQ ID NO: 318)

GGUUUUUUUUUUUUUUUUUGG; (SEQ ID NO: 319)

GGGGGGGGGGUUUGGGGGGGGG; (SEQ ID NO: 320)

GGGGGGGGGGUUUUGGGGGGGGG; (SEQ ID NO: 321)

GGGGGGGGGGUUUUUGGGGGGGG; (SEQ ID NO: 322)

GGGGGGGGGUUUUUUGGGGGGGG; (SEQ ID NO: 323)

GGGGGGGGGUUUUUUGGGGGGGG; (SEQ ID NO: 324)

GGGGGGGGGUUUUUUUGGGGGGGG; (SEQ ID NO: 325)

GGGGGGGGUUUUUUUUGGGGGGG; (SEQ ID NO: 326)

GGGGGGGGUUUUUUUUUGGGGGG; (SEQ ID NO: 327)

GGGGGGGUUUUUUUUUUGGGGGG; (SEQ ID NO: 328)

GGGGGGGUUUUUUUUUUUGGGGG; (SEQ ID NO: 329)

GGGGGGUUUUUUUUUUUUUGGGG; (SEQ ID NO: 330)

GGGGGUUUUUUUUUUUUUUGGGG; (SEQ ID NO: 331)

GGGUUUUUUUUUUUUUUUUUGGG; (SEQ ID NO: 332)

GUUUUUUUUUUUUUUUUUUUUUUUUUUG; (SEQ ID NO: 333)

GGUUUUUUUUUUUUUUUUUUUUUUUUUUUGG; (SEQ ID NO: 334)

GGGUUUUUUUUUUUUUUUUUUUUUUUUUUUGGG; (SEQ ID NO: 335)

GGGGUUUUUUUUUUUUUUUUUUUUUUUUUUUGGG; (SEQ ID NO: 336)

GGGGGUUUUUUUUUUUUUUUUUUUUUUUUUUUUGGGG; (SEQ ID NO: 337)

GGGGGGUUUUUUUUUUUUUUUUUUUUUUUUUUUUUGGGGG; (SEQ ID NO: 338)

GGGGGGGUUUUUUUUUUUUUUUUUUUUUUUUUUUUUUGGGGG; (SEQ ID NO: 339)

GGGGGGGGUUUUUUUUUUUUUUUUUUUUUUUUUUUUUUGGGGGG; (SEQ ID NO: 340)

GGGGGGGGGUUUUUUUUUUUUUUUUUUUUUUUUUUUUUUUGGGGGGG; (SEQ ID NO: 341)

GGUUUGG; (SEQ ID NO: 342)

GGUUUUGG; (SEQ ID NO: 343)

GGUUUUUGG; (SEQ ID NO: 344)

GGUUUUUUGG; (SEQ ID NO: 345)

GGUUUUUUUGG; (SEQ ID NO: 346)

GGUUUUUUUUGG; (SEQ ID NO: 347)

GGUUUUUUUUUGG; (SEQ ID NO: 348)

GGUUUUUUUUUUGG; (SEQ ID NO: 349)

GGUUUUUUUUUUUGG; (SEQ ID NO: 350)

GGUUUUUUUUUUUUGG; (SEQ ID NO: 351)

GGUUUUUUUUUUUUUGG; (SEQ ID NO: 352)

GGUUUUUUUUUUUUUUGG; (SEQ ID NO: 353)

GGUUUUUUUUUUUUUUUGG; (SEQ ID NO: 354)

GGGUUUGGG; (SEQ ID NO: 355)

GGGUUUUGGG; (SEQ ID NO: 356)

GGGUUUUUGGG; (SEQ ID NO: 357)

GGGUUUUUUGGG; (SEQ ID NO: 358)

GGGUUUUUUUGGG; (SEQ ID NO: 359)

GGGUUUUUUUUGGG; (SEQ ID NO: 360)

GGGUUUUUUUUUGGG; (SEQ ID NO: 361)

GGGUUUUUUUUUUGGG; (SEQ ID NO: 362)

GGGUUUUUUUUUUUGGG; (SEQ ID NO: 363)

GGGUUUUUUUUUUUUGGG; (SEQ ID NO: 364)

GGGUUUUUUUUUUUUUGGG; (SEQ ID NO: 365)

```
                                         (SEQ ID NO: 366)
GGGUUUUUUUUUUUUUUUGGGUUUUUUUUUUUUUUUGG-
GUUUUUUUUUUUUUUGGG;

(SEQ ID NO: 367)
GGGUUUUUUUUUUUUUUUGGGGGUUUUUUUUUUUUUUGGG;

(SEQ ID NO: 368)
GGGUUUGGGUUUGGGUUUGGGUUUGGGUUUGGGUUUGGGUUUGG
G;

(short GU-rich, SEQ ID NO: 369)
GGUUUUUUUUUUUUUUUGGG
or (SEQ ID NO: 370)
CCCUUUUUUUUUUUUUUCCCUUUUUUUUUUUUUUCCC-
UUUUUUUUUUUUUUCCC (SEQ ID NO: 371)
CCCUUUCCCUUUCCCUUUCCCUUUCCCUUUCCCUUUCCCUUUCC
C (SEQ ID NO: 372)
CCCUUUUUUUUUUUUUUCCCCCUUUUUUUUUUUUUUCCC
``` or from a sequence having at least 60%, 70%, 80%, 90%, or even 95% sequence identity with any of these sequences.

According to a further particularly preferred embodiment, an immunostimulatory nucleic acid sequence, particularly an is RNA, as used herein, may consist of or comprise a nucleic acid of formula (III) or (IV):

$$(N_u G_l X_m G_n N_v)_a,$$ (formula (III))

wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
wherein
when l=1, G is guanosine (guanine) or an analogue thereof,
when l>1, at least 50% of these nucleotides (nucleosides) are guanosine (guanine) or an analogue thereof;

m is an integer and is at least 3;
wherein
when m=3, X is uridine (uracil) or an analogue thereof, and
when m>3, at least 3 successive uridines (uracils) or analogues of uridine (uracil) occur;

n is an integer from 1 to 40,
wherein
when n=1, G is guanosine (guanine) or an analogue thereof,
when n>1, at least 50% of these nucleotides (nucleosides) are guanosine (guanine) or an analogue thereof;

u,v may be independently from each other an integer from 0 to 50,
preferably wherein when u=0, v≥1, or
when v=0, u≥1;

wherein the nucleic acid molecule of formula (III) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a$$ (formula (IV))

wherein:

C is cytidine (cytosine), uridine (uracil) or an analogue of cytidine (cytosine) or uridine (uracil), preferably cytidine (cytosine) or an analogue thereof;

X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;

N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
wherein
when l=1, C is cytidine (cytosine) or an analogue thereof,
when l>1, at least 50% of these nucleotides (nucleosides) are cytidine (cytosine) or an analogue thereof;

m is an integer and is at least 3;
wherein
when m=3, X is uridine (uracil) or an analogue thereof,
when m>3, at least 3 successive uridines (uracils) or analogues of uridine (uracil) occur;

n is an integer from 1 to 40,
wherein
when n=1, C is cytidine (cytosine) or an analogue thereof,
when n>1, at least 50% of these nucleotides (nucleosides) are cytidine (cytosine) or an analogue thereof u,v may be independently from each other an integer from 0 to 50,
preferably wherein when u=0, v≥1, or
when v=0, u≥1;

wherein the nucleic acid molecule of formula (IV) according to the invention has a length of at least 50 nucleotides, preferably of at least 100 nucleotides, more preferably of at least 150 nucleotides, even more preferably of at least 200 nucleotides and most preferably of at least 250 nucleotides.

Any of the definitions given above in formulae (I) and (II), e.g. for elements N (i.e. $N_u$ and $N_v$) and X ($X_m$), particularly the core structure as defined above, as well as for integers a, l, m, n, u and v, similarly apply to elements of formula (III) and (IV) correspondingly. The definition of bordering elements $N_u$ and $N_v$ in formula (IV) is identical to the definitions given above for $N_u$ and $N_v$ in formula (IV).

According to a very particularly preferred embodiment, the inventive nucleic acid molecule according to formula (IV), which may be used as an immunostimulatory nucleic acid sequence, particularly an is RNA, may be selected from e.g. any of the following sequences:

(SEQ ID NO: 373)
UAGCGAAGCUCUUGGACCUAGGUUUUUUUUUUUUUUUGGGUGCGUUCCUA-
GAAGUACACG (SEQ ID NO: 374)
UAGCGAAGCUCUUGGACCUAGGUUUUUUUUUUUUUUUGGGUGCGUUCCUA-
GAAGUACACG AUCGCUUCGA GAACCUGGAUCCAAAAAAAAAAAAAAACCCACGCAAG-
GAUCUUCAUGUGC (SEQ ID NO: 375)
GGGAGAAAGCUCAAGCUUGGAGCAAUGCCCGCACAUUGAGGAAACCGAGUUG-
CAUAUCUCAGAGUAUUGGCCCCCGUGUAGGUUAUUCUUGACAGACAGUG-
GAGCUUAUUCACUCCCAGGAUCCGAGUCGCAUACUACGGUACUGGUGACAGAC-
CUAGGUCGUCAGUUGACCAGUCCGCCACUAGACGUGAGUCCGUCAAAGCAGUUA-
GAUGUUACACUCUAUUAGAUC (SEQ ID NO: 376)
GGGAGAAAGCUCAAGCUUGGAGCAAUGCCCGCACAUUGAGGAAACCGAGUUG-
CAUAUCUCAGAGUAUUGGCCCCCGUGUAGGUUAUUCUUGACAGACAGUG-
GAGCUUAUUCACUCCCAGGAUCCGAGUCGCAUACUACGGUACUGGUGACAGAC-
CUAGGUCGUCAGUUGACCAGUCCGCCACUAGACGUGAGUCCGUCAAAGCAGUUA-
GAUGUUACACUCUAUUAGAUCUCGGAUUACAGCUGGAAGGAGCAGGAGUAGUG-
UUCUUGCUCUAAGUACCGAGUGUGCCCAAUACCCGAUCAGCUUAUUAACGAAC-
GGCUCCUCCUCUUAGACUGCAGCGUAAGUGCGGAAUCUGGGGAUCAAAUUACU-
GACUGCCUGGAUUACCCUCGGACAUAUAACCUUGUAGCAC-
GCUGUUGCUGUAUAGGUGACCAACGCCCACUCGAGUAGACCAGCUCU-
CUUAGUCCGGACAAUGAUAGGAGGCGCGGUCAAUCUACUUCUGGCUAGUU-
AAGAAUAGGCUGCACCGACCUCUAUAAGUAGCGUGUCCUCUAG (SEQ ID NO: 377)
GGGAGAAAGCUCAAGCUUGGAGCAAUGCCCGCACAUUGAGGAAACCGAGUUG-
CAUAUCUCAGAGUAUUGGCCCCCGUGUAGGUUAUUCUUGACAGACAGUG-
GAGCUUAUUCACUCCCAGGAUCCGAGUCGCAUACUACGGUACUGGUGACAGAC-
CUAGGUCGUCAGUUGACCAGUCCGCCACUAGACGUGAGUCCGUCAAAGCAGUUA-
GAUGUUACACUCUAUUAGAUCUCGGAUUACAGCUGGAAGGAGCAGGAGUAGUG-
UUCUUGCUCUAAGUACCGAGUGUGCCCAAUACCCGAUCAGCUUAUUAACGAAC-
GGCUCCUCCUCUUAGACUGCAGCGUAAGUGCGGAAUCUGGGGAUCAAAUUACU-
GACUGCCUGGAUUACCCUCGGACAUAUAACCUUGUAGCAC-
GCUGUUGCUGUAUAGGUGACCAACGCCCACUCGAGUAGACCAGCUCU-
CUUAGUCCGGACAAUGAUAGGAGGCGCGGUCAAUCUACUUCUGGCUAGUU-
AAGAAUAGGCUGCACCGACCUCUAUAAGUAGCGUGUCCUCUAGAGCUAC-
GCAGGUUCGCAAUAAAAGCGUUGAUUAGUGUGCAUAGAACAGACCU-
CUUAUUCGGUGAAACGCCAGAAUGCUAAAAUUCCAAUAACUCUUCCCAAAAC-
GCGUACGGCCGAAGACGCGCGCUUUAUCUUGUGUACGUUCUCGCACAUGGAA-
GAAUCAGCGGGCAUGGUGGUAGGGCAAUAGGGGAGCUGGGUAG-
CAGCGAAAAGGGCCCCUGCGCACGUAGCUUCGCUGUUCGUCUGAAACAACCCGG-
CAUCCGUUGUAGCGAUCCCGUUAUCAGUGUUAUUCUUGUGCGCACUAAGAU-
UCAUGGUGUAGUCGACAAUAACAGCGUCUUGGCAGAUUCUGGUCACGUG-
CCCUAUGCCCGGGCUUGUGCCUCUCAGGUGCACAGCGAUACUUAAA-
GCCUUCAAGGUACUCGACGUGGGUACCGAUUCGUGACACUUCCUAAGAU-
UAUUCCACUGUGUUAGCCCCGCACCGCCGACCUAAACUGGUCCAAUGUAUAC-
GCAUUCGCUGAGCGGAUCGAUAAUAAAAGCUUGAAUU (SEQ ID NO: 378)
GGGAGAAAGCUCAAGCUUAUCCAAGUAGGCUGGUCACCUGUACAAC-
GUAGCCGGUAUUUUUUUUUUUUUUUUUUUUUGACCGUCUCAAGGUCCAA-
GUUAGUCUGCCUAUAAAGGUGCGGAUCCACAGCUGAUGAAAGACUUGUG-
CGGUACGGUUAAUCUCCCCUUUUUUUUUUUUUUUUUUUUAGU-
AAAUGCGUCUACUGAAUCCAGCGAUGAUGCUGGCCCAGAUC (R 722 SEQ ID NO: 379)
GGGAGAAAGCUCAAGCUUAUCCAAGUAGGCUGGUCACCUGUACAAC-
GUAGCCGGUAUUUUUUUUUUUUUUUUUUUUUGACCGUCUCAAGGUCCAA-
GUUAGUCUGCCUAUAAAGGUGCGGAUCCACAGCUGAUGAAAGACUUGUG-
CGGUACGGUUAAUCUCCCCUUUUUUUUUUUUUUUUUUUUAGU-
AAAUGCGUCUACUGAAUCCAGCGAUGAUGCUGGCCCAGAUCUUCGACCACAA-
GUGCAUAUAGUAGUCAU-
CGAGGGUCGCCUUUUUUUUUUUUUUUUUUUUUUGGCCCAGUUCUGAGACU-
UCGCUAGAGACUACAGUUACAGCUGCAGUAGUAACCACUGCGGCUAUUGCAG-
GAAAUCCCGUUCAGGUUUUUUUUUUUUUUUUUUUUUCCGCUCACUAUGAU-
UAAGAACCAGGUGGAGUGUCACUGCUCUCGAGGUCUCACGA-
GAGCGCUCGAUACAGUCCUUGGAA-
GAAUCUUUUUUUUUUUUUUUUUUUUUGUGCGACGAUCACAGAGAACU-
UCUAUUCAUGCAGGUCUGCUCUA (SEQ ID NO: 380)
GGGAGAAAGCUCAAGCUUAUCCAAGUAGGCUGGUCACCUGUACAAC-
GUAGCCGGUAUUUUUUUUUUUUUUUUUUUUUGACCGUCUCAAGGUCCAA-
GUUAGUCUGCCUAUAAAGGUGCGGAUCCACAGCUGAUGAAAGACUUGUG-
CGGUACGGUUAAUCUCCCCUUUUUUUUUUUUUUUUUUUUAGU-
AAAUGCGUCUACUGAAUCCAGCGAUGAUGCUGGCCCAGAUCUUCGACCACAA-

-continued

```
GUGCAUAUAGUAGUCAU-
CGAGGGUCGCCUUUUUUUUUUUUUUUUUUUUUUUGGCCCAGUUCUGAGACU-
UCGCUAGAGACUACAGUUACAGCUGCAGUAGUAACCACUGCGGCUAUUGCAG-
GAAAUCCCGUUCAGGUUUUUUUUUUUUUUUUUUUUCCGCUCACUAUGAU-
UAAGAACCAGGUGGAGUGUCACUGCUCUCGAGGUCUCACGA-
GAGCGCUCGAUACAGUCCUUGGAA-
GAAUCUUUUUUUUUUUUUUUUUUUUUGUGCGACGAUCACAGAGAACU-
UCUAUUCAUGCAGGUCUGCUCUAGAACGAACUGACCUGACGCCUGAACU-
UAUGAGCGUGCGUAUUUUUUUUUUUUUUUUUUUUUCCUCCCAACAAAU-
GUCGAUCAAUAGCUGGGCUGUUGGAGACGCGUCAGCAAAUGCCGUG-
GCUCCAUAGGACGUGUAGACUUCUAUUUUUUUUUUUUUUUUUUUCCCGG-
GACCACAAAUAAUAUUCUUGCUUGGUUGGGCGCAAGGGCCCCGUAUCAGGUCAU-
AAACGGGUACAUGUUG-
CACAGGCUCCUUUUUUUUUUUUUUUUUUUUUUUCGCUGAGUUAUUCCGGUCUCAAA
AGACGGCAGACGUCAGUCGACAACACGGUCUAAAGCAGUG-
CUACAAUCUGCCGUGUUCGUGUUUUUUUUUUUUUUUUUUUUGUGAACCUACAC-
GGCGUGCACUGUAGUUCGCAAU-
UCAUAGGGUACCGGCUCAGAGUUAUGCCUUGGUUGAAAACUGCCCAGCAUACU-
UUUUUUUUUUUUUUUUUUUCAUAUUCCCAUGCU-
AAGCAAGGGAUGCCGCGAGUCAUGUUAAGCUUGAAUU
```

According to another very particularly preferred embodiment, the nucleic acid molecule according to formula (V) may be selected from e.g. any of the following sequences:

```
                                           (SEQ ID NO: 381)
UAGCGAAGCUCUUGGACCUACCUUUUUUUUUUUUUUCCCUGCGUUCCUAG
AAGUACACG
```
or
```
                                           (SEQ ID NO: 382)
UAGCGAAGCUCUUGGACCUACCUUUUUUUUUUUUUUCCCUGCGUUCCUA
GAA-
GUACACGAUCGCUUCGAGAACCUGGAUGGAAAAAAAAAAAAAAGGGAC-
GCAAGGAUCUUCAUGUGC
``` or from a sequence having at least 60%, 70%, 80%, 90%, or even 95% sequence identity with any of these sequences.

Finally, the so called "(adjuvant) component", which may be used to together with the mRNA in the inventive vaccine, is preferably prepared according to a first step by complexing the at least one (m)RNA of the (adjuvant) component with a cationic or polycationic compound and/or with a polymeric carrier, preferably as defined herein, in a specific ratio to form a stable complex. In this context, it is highly preferable, that no free cationic or polycationic compound or polymeric carrier or only a neclectably small amount thereof remains in the (adjuvant) component after complexing the (m)RNA. Accordingly, the ratio of the (m)RNA and the cationic or polycationic compound and/or the polymeric carrier in the (adjuvant) component is typically selected in a range that the (m)RNA is entirely complexed and no free cationic or polycationic compound or polymeric carrier or only a neclectably small amount thereof remains in the composition. Preferably the ratio of the (adjuvant) component, i.e. the ratio of the (m)RNA to the cationic or polycationic compound and/or the polymeric carrier, preferably as defined herein, is selected from a range of about 6:1 (w/w) to about 0, 25:1 (w/w), more preferably from about 5:1 (w/w) to about 0, 5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the (m)RNA to the cationic or polycationic compound and/or the polymeric carrier, preferably as defined herein, in the (adjuvant) component, may also be calculated on the basis of the nitrogen/phosphate ratio (N/P-ratio) of the entire complex of the (adjuvant) component. In the context of the present invention, an N/P-ratio is preferably in the range of about 0.1-10, preferably in a range of about 0.3-4 and most preferably in a range of about 0.5-2 or 0.7-2 regarding the ratio of (m)RNA:cationic or polycationic compound and/or polymeric carrier, preferably as defined herein, in the complex, and most preferably in the range of about 0.7-1.5, preferably provided the cationic or polycationic compound in the complex is a cationic or polycationic cationic or polycationic protein or peptide and/or the polymeric carrier is as defined above. Such ratios, particularly weight and/or N/P ratios may also be applied to ratios of the at least one mRNA encoding at least one antigen as defined herein to a cationic or polycationic polymer or a polymeric carrier as defined herein used to complex the at least one mRNA.

According to a further preferred aspect, the mRNA of the inventive vaccine encoding at least one antigen as defined above may be formulated together with an (adjuvant) component as defined above, wherein the inventive vaccine may comprise a) an (adjuvant) component, comprising or consisting of at least one (m)RNA, complexed with a cationic or polycationic compound and/or with a polymeric carrier, preferably as defined herein, and b) at least one free mRNA, encoding an antigen, preferably as defined herein. This formulation is preferably as defined above. Furthermore, the entire formulation of a) and b) may be additionally packaged with a carrier molecule to allow combined packaging the (adjuvant) component and the antigen. Such a carrier molecule may be selected from any polymer suitable for packaging and preferably transporting the entire formulation of a) and b) into cells, tissue, etc., of a patient as defined herein, e.g. from a cationic or polycationic polymer as defined herein or from any further polymer suitable for this purpose, e.g. a polymeric carrier as defined above.

The ratio of all components of the entire inventive vaccine composition, as defined above, preferably, an adjuvant component comprising or consisting of at least one immunostimulatory nucleic acid sequence, complexed with a cationic or polycationic compound, the at least one mRNA encoding at least one antigen, and/or a carrier molecule, formulated in the inventive vaccine, may be calculated on the basis of the nitrogen/phosphate ratio (N/P-ratio) of all these components. In the context of the present invention, an N/P-ratio is preferably in the range of about 0.01-4, 0.01-2, 0.1-2 or 0.1-1.5 regarding the ratio of nucleic acids:cationic or polycationic peptide contained in the inventive vaccine, and most preferably in the range of about 0.1-1. Such an N/P ratio is preferably designed to provide good transfection properties in vivo and transport into and through cell membranes. Preferably, for this purpose, cationic or polycationic compound and/or polymeric carriers as used herein, are based on peptide sequences.

In a further preferred aspect of the present invention the inventive vaccine may comprise a pharmaceutically acceptable carrier and/or vehicle. In the context of the present invention, a pharmaceutically acceptable carrier typically includes the liquid or non-liquid basis of a composition comprising the components of the inventive vaccine. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the inventive vaccine. The term "compatible" as used here means that these constituents of the inventive vaccine are capable of being mixed with the components of the inventive vaccine in such a manner that no interaction occurs which would substantially reduce the pharmaceutical effectiveness of the inventive vaccine under typical use conditions.

According to a specific aspect, the inventive vaccine may comprise an adjuvant. In this context, an adjuvant may be understood as any compound, which is suitable to initiate or increase an immune response of the innate immune system, i.e. a non-specific immune response. With other words, when administered, the vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

According to one aspect such an adjuvant may be selected from an (adjuvant) component as defined above.

According to one further aspect such an adjuvant may be selected from any adjuvant known to a skilled person and suitable for the present case, i.e. supporting the induction of an innate immune response in a mammal and/or suitable for depot and delivery of the components of the inventive vaccine. Preferred as adjuvants suitable for depot and delivery are cationic or polycationic compounds as defined above. Likewise, the adjuvant may be selected from the group consisting of, without being limited thereto, cationic or polycationic compounds as defined above, from chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTherm™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendaicontaining lipid matrices; Span-85 (sorbitan trioleate); Specol (emulsion of Marcol 52, Span 85 and Tween 85); squalene or ROBANE® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); THERAMID® (N-acetylglucosaminyl-N-acetylmuramyl-L-Ala-D-isoGlu-L-Aladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T cells, such as GM-CSF, IL-12, IFNγ, immunostimulatory RNA sequences as defined herein, CpG DNA, etc.

The inventive vaccine may additionally contain a further immunotherapeutic agent selected from immunoglobulins, preferably IgGs, monoclonal or polyclonal antibodies, polyclonal serum or sera, etc. Preferably, such a further immunotherapeutic agent may be provided as a peptide/protein or may be encoded by a nucleic acid, preferably by a DNA or an RNA, more preferably an mRNA. Such an immunostimulatory agent allows providing passive vaccination additional to active vaccination triggered by the mRNA encoded antigen of the inventive composition or vaccine composition.

The inventive vaccine can additionally contain one or more auxiliary substances in order to increase its immunogenicity or immunostimulatory capacity, if desired. A synergistic action of the inventive vaccine and of an auxiliary substance, which may be optionally contained in the vaccine or may be formulated with the inhibitor, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFNα, IFNβ, IFNγ, GM-CSF, G-CSF, M-CSF, LT-beta or TNF-alpha, growth factors, such as hGH.

The inventive vaccine can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13, a ligand of a NOD-like receptor, or a ligand of a RIG-I like receptor.

In this context the inventive vaccine may also additionally contain an immunostimulatory nucleic acid, preferably an immunostimulatory RNA (is RNA), as defined above.

The inventive vaccine as defined according to the first embodiment of the present invention may furthermore comprise further additives or additional compounds. Further additives which may be included in the inventive vaccine are emulsifiers, such as, for example, TWEEN®; wetting agents, such as, for example, sodium lauryl sulfate; colouring agents; taste-imparting agents, pharmaceutical carriers; tablet-forming agents; stabilizers; antioxidants; preservatives.

One further additive, which may be contained in the inventive vaccine, may be an antibacterial agent. In this context, any anti-bacterial agents known to one of skill in the art may be used in combination with the components of the inventive vaccine as defined herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefinenoxime, Cefoperazone, Cefoperazone-sulbactam, Cefotaxime, Cefoxitin, Cefbirome, Cefpodoxime, Cefpodoxime-clavulanic acid, Cefpodoxime-sulbactam, Cefbrozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillintazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

Another additive, which may be contained in the inventive vaccine, may be an anti-viral agents, preferably, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, t-705, zanamivir (RELENZA®), and oseltamivir (TAMIFLU®). Other anti-viral agents include influenza virus vaccines, e.g., FLUARIX® (Glaxo SmithKline), FLUMIST® (MedImmune Vaccines), FLUVIRIN® (Chiron Corporation), FLULAVA® (GlaxoSmithKline), AFLURIA® (CSL Biotherapies Inc.), AGRIFLU® (Novartis) or FLUZONE® (Aventis Pasteur).

The inventive vaccine typically comprises a "safe and effective amount" of the components of the inventive vaccine as defined herein. As used herein, a "safe and effective amount" preferably means an amount of the components, preferably of the at least one mRNA, that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

As defined according to the first embodiment, the inventive vaccine comprising at least one mRNA encoding at least one antigen may be used in the prophylaxis and treatment of a disease in newborns and/or infants, preferably exhibiting an age of not more than 3 or 2 years, preferably of not more than 1 year (12 months), more preferably of not more than 9, 6 or 3 months. The treatment preferably comprises vaccination of the newborn or infant and eliciting an immune response in said newborn or infant. Preferably, a newborn or infant is a mammal (patient), preferably a human (patient), typically exhibiting an age of not more than 3 or usually 2 years, preferably of not more than 1.5 years, more preferably of not more than 1 year (12 months), even more preferably of not more than 9 months, 6 months or even 3 months. Accordingly, a newborn or infant may comprise an age of about 0 to 3 or usually 0 to 2 years, preferably of 0 to 1.5 years, more preferably of 0 to 1 years (0 to 12 months), even more preferably of not more than 0 to 9 months, 0 to 6 months or even 0 to 3 months. A newborn or infant may furthermore be distinguished into a newborn, typically exhibiting an age of not more than 1 year (12 months), preferably of not more than 9 months, 6 months or even 3 months. Accordingly, a newborn or infant may comprise an age of about 0 to 1 years (0 to 12 months), preferably of not more than 0 to 9 months, 0 to 6 months or even 0 to 3 months. A newborn or infant may furthermore be distinguished into an infant, typically exhibiting an age of more than 3 months, preferably exhibiting an age of 6 months, more preferably exhibiting an age of more than 9 months, but additionally exhibiting an age of not more than 3 or usually 2 years, preferably of not more than 1.5 years, more preferably of not more than 1 year (12 months), even more preferably of not more than 9 months or even 6 months. Accordingly, a newborn or infant may comprise an age of about 3 months to about 3 years, about 3 months to about 2 years, about 3 months to about 1.5 years, or about 3 months to about 1 year (12 months), about 6 months to about 3 years, about 6 months to about 2 years, about 6 months to about 1.5 years, or about 6 months to about 1 year (12 months), about 9 months to about 3 years, about 9 months to about 2 years, or about 9 months to about 1.5 years, about 12 months to about 3 years, about 12 months to about 2 years, or about 12 months to about 1.5 years. The newborns and or infant may be male or female.

As furthermore defined in the first embodiment of the present invention, the treatment comprises vaccination of the patient and eliciting an immune response in said patient. In this context, vaccination typically occurs via administration of the inventive vaccine. Administration may occur parenterally, orally, nasally, pulmonary, by inhalation (e.g. via an aerosol or spray), topically, rectally, buccally, vaginally, or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. Preferably, the inventive vaccine may be administered intradermally to reach APCs in the dermis. Likewise preferably, the inventive vaccine as defined herein may be administered orally in any orally acceptable dosage form including, but not limited to, capsules, tablets, aqueous suspensions or solutions. Likewise preferably, the inventive vaccine may be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive vaccine may be formulated in a suitable ointment, containing the inventive vaccine and optionally further components as defined herein suspended or dissolved in one or more carriers. Pulmonary administration can also be employed, e.g., by use of an inhaler or nebulizer, and formulation with an aerosolizing agent for use as a spray.

The inventive vaccine may be used in combination with other therapies, preferably with a therapy for a disease as defined herein, or further therapies. As used herein, the term "in combination," in the context of the administration of two or more therapies to a newborn or an infant as defined herein, refers to the use of more than one therapy, preferably two therapies or even more. The use of the term "in combination" does not restrict the order in which therapies are administered to a newborn or an infant as defined herein. For example, a first therapy (e.g., a first prophylactic or therapeutic agent) can be administered at any time prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a newborn or an infant as defined herein. In some aspects, the one or more other therapies are surgery, immunotherapies, gene therapies, pain treatments, anti-fever medications, therapies that alleviate or assist with breathing, other (active or passive) vaccinations/immunizations, antiviral therapies, antibacterial therapies, antifungal therapies, anti-parasite therapies, anti-allergic therapies, conventional tumour therapies, chemotherapies, or may include a post exposition prophylaxis in or for any of the diseases mentioned herein, preferably for rabies, RSV viral infection, etc.

In certain aspects, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In specific aspects, two or more therapies are administered within the same patient visit.

Exemplary doses for mRNAs encoding at least one antigen as defined herein may range, without being limited thereto, from about 10 ng to 1 g, 100 ng to 100 mg, 1 μg to 10 μg, or 30-300 μg mRNA per patient. Preferably, the inventive vaccine is formulated accordingly to comprise one dose, two doses, three or even more doses.

According to a specific aspect, the inventive vaccine may be administered to a newborn or an infant as a single dose. In certain aspects, the inventive vaccine may be administered to a newborn or an infant as a single dose followed by a second dose later and optionally even a third, fourth (or more) dose subsequent thereto etc. In accordance with this aspect, booster inoculations with the inventive vaccine may be administered to a newborn or an infant at specific time intervals, preferably as defined below, following the second (or third, fourth, etc.) inoculation. In certain aspects, such booster inoculations with the inventive vaccine may utilize an additional compound or component as defined for the inventive vaccine as defined herein. In some aspects, the administration of the same inventive vaccine and/or booster administrations may be repeated and such administrations may be separated by at least 1 day, 2 days, 3 days, 4 days, 5 days, 10 days, 15 days, 30 days, 45 days, 2 months, 75 days, e.g. 1 to 5 days, 1 to 10 days, 5 to 15 days, 10 to 20 days, 15 to 25 days, 20 to 30 days, 25 to 35 days, 30 to 50 days, 40 to 60 days, 50 to 70 days, 1 to 75 days, or 1 month, 2 months, 3 months, 4 months, 5 months, or at least 6, 7, 8, 9, 10, 11, 12 months, 18 months, 24 months, 30 months, 36 months, 1 year, 2 years, 3 years, 5 years, 10 years, 15 years, 20 years, 30 years, 40 years, 50 years, 60 years, or even more. In certain aspects, the inventive vaccine may be administered to a subject as a single dose once per year.

In particular aspects, the inventive vaccine may be administered to a newborn or an infant in the fall or winter, i.e., prior to or during the influenza season in each hemisphere. In one aspect, a newborn or an infant is administered his/her first dose early in the season, e.g., late September or early October, so that the second dose (if necessary) can be given prior to the peak of the influenza season.

In particular aspects, the inventive vaccine may be administered at least once, preferably twice or more to a newborn or an infant prior to a treatment of a disease as defined herein, preferably at least 1 day, 2 days, 3 days, 4 days, 5 days, 10 days, 15 days, 30 days, 45 days, 2 months, 75 days, e.g. 1 to 5 days, 1 to 10 days, 5 to 15 days, 10 to 20 days, 15 to 25 days, 20 to 30 days, 25 to 35 days, 30 to 50 days, 40 to 60 days, 50 to 70 days, 1 to 75 days, or 1 month, 2 months, 3 months, 4 months, 5 months, or at least 6, 7, 8, 9, 10, 11, or 12 months prior to a treatment of a disease as defined herein. A second or further dose may then be administered directly prior to treatment, concurrent with or subsequent to treatment.

Furthermore, a disease as defined according to the first embodiment of the present invention is any disease selected from infectious diseases, preferably (viral, bacterial or protozoological) infectious diseases, autoimmune diseases, allergies or allergic diseases or cancer or tumour diseases.

Such diseases include cancer or tumour diseases, preferably selected from melanomas, malignant melanomas, colon carcinomas, lymphomas, sarcomas, blastomas, renal carcinomas, gastrointestinal tumours, gliomas, prostate tumours, bladder cancer, rectal tumours, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), leukaemia, hepatomas, various virus-induced tumours such as, for example, papilloma virus-induced carcinomas (e.g. cervical carcinoma=cervical cancer), adenocarcinomas, herpes virus-induced tumours (e.g. Burkitt's lymphoma, EBV-induced B cell lymphoma), heptatitis B-induced tumours (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumours, retinoblastoma, basalioma, brain metastases, medulloblastomas, vaginal cancer, pancreatic cancer, testicular cancer, Hodgkin's syndrome, meningiomas, Schneeberger disease, hypophysis tumour, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumours, oligodendroglioma, vulval cancer, intestinal cancer, colon carcinoma, oesophageal carcinoma (=Oesophageal cancer), wart involvement, tumours of the small intestine, craniopharyngeomas, ovarian carcinoma, genital tumours, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumour, prostate cancer (=prostate tumours), etc.

According to one further specific aspect, diseases as defined herein comprise infectious diseases, preferably (viral, bacterial or protozoological) infectious diseases. Such infectious diseases, preferably viral, bacterial or protozoological infectious diseases, are typically selected from viral infectious diseases such as influenza, preferably influenza-A, influenza-B, influenza-C or thogotovirus, more preferably influenza-A comprising e.g. haemagglutinin subtypes H1, H2, H3, H4, H5, H6, H7, H8, H9, H10, H11, H12, H13, H14 or H15, and/or neuroamidase subtypes N1, N2, N3, N4, N5, N6, N7, N8 or N9, or preferably influenza-A subtypes H1M, H1N2, H2N2, H2N3, H3N1, H3N2, H3N3, H5N1, H5N2, H7N7 or H9N2, etc., or any further combination malaria, severe acute respiratory syndrome (SARS), respiratory syncytial virus infection, yellow fever, AIDS, Lyme borreliosis, Leishmaniasis, anthrax, meningitis, Condyloma acuminata, hollow warts, Dengue fever, three-day fever, Ebola virus, cold, early summer meningoencephalitis (FSME), shingles, hepatitis, herpes simplex type I, herpes simplex type II, Herpes zoster, Japanese encephalitis, Arenavirus-associated diseases (Lassa fever infection), Marburg virus, measles, foot-and-mouth disease, mononucleosis infectiosa (Pfeiffer's glandular fever), mumps, Norwalk virus infection, smallpox, polio (childhood lameness), pseudo-croup, Erythema infectiosum (fifth disease), rabies, warts, West Nile fever, chickenpox, cytomegalic virus (CMV), bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, *typhus* fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, *paratyphus*, plague, Reiter's syndrome, Rocky Mountain spotted fever, *Salmonella paratyphus, Salmonella typhus*, scarlet fever, syphilis, tetanus, tripper, tsutsugamushi disease, tuberculosis, *typhus*, vaginitis (colpitis), soft chancre, and infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

According to another specific aspect, diseases as defined herein comprise autoimmune diseases as defined in the following. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T cell bypass. A normal immune system requires the activation of B cells by T cells before the former can produce antibodies in large quantities. This requirement of a T cell can be by-passed in rare instances, such as infection by organisms producing superantigens, which are capable of initiating polyclonal activation of B cells, or even of T cells, by directly binding to the β-subunit of T cell receptors in a non-specific fashion. Another explanation deduces autoimmune diseases from a "Molecular Mimicry": an exogenous antigen may share structural similarities with certain host antigens; thus, any antibody produced against this antigen (which mimics the self-antigens) can also, in theory, bind to the host antigens and amplify the immune response. Autoimmune diseases based on molecular mimicry are known to a skilled person for various viral and bacterial antigens. The most striking form of molecular mimicry is observed in Group A beta-haemolytic streptococci, which shares antigens with human myocardium, and is responsible for the cardiac manifestations of rheumatic fever.

Additionally, according to one further specific aspect, diseases as defined herein comprise allergies or allergic diseases, i.e. diseases related to allergies. Allergy is a condition that typically involves an abnormal, acquired immunological hypersensitivity to certain foreign antigens or allergens, such as the allergy antigens as defined herein. Such allergy antigens or allergens may be selected from allergy antigens as defined herein antigens derived from different sources, e.g. from animals, plants, fungi, bacteria, etc. Allergens in this context include e.g. danders, grasses, pollens, molds, drugs, or numerous environmental triggers, etc. Allergies normally result in a local or systemic inflammatory response to these antigens or allergens and lead to immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, asthma, allergic asthma (leading to swelling of the nasal mucosa), allergic conjunctivitis (leading to redness and itching of the conjunctiva), allergic rhinitis ("hay fever"), anaphylaxis, angiodema, atopy, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. Treatment of such allergic disorders or diseases may occur preferably by desensitizing the immune reaction which triggers a specific immune response. Such a desensitizing may be carried out by administering an effective amount of the allergen or allergic antigen encoded by the nucleic acid as defined herein, preferably, when formulated as a pharmaceutical composition, to induce a slight immune reaction. The amount of the allergen or allergic antigen may then be raised step by step in subsequent administrations until the immune system of the patient to be treated tolerates a specific amount of allergen or allergic antigen.

Diseases in the context of the present invention may also include type II hypersensitivity reactions (cytotoxic, antibody-dependent), including e.g. autoimmune hemolytic anemia, thrombocytopenia, erythroblastosis fetalis, Goodpasture's syndrome, Graves' disease, Myasthenia Gravis, etc.; type III hypersensitivity reactions (immune complex disease), including e.g. serum sickness, Arthus reaction, Systemic lupus erythematosus (SLE), etc.; type IV hypersensitivity reactions (delayed-type hypersensitivity (DTH), cell-mediated immune memory response, antibody-independent), including e.g. contact dermatitis, Mantoux test, chronic transplant rejection, multiple sclerosis, etc.; and type V hypersensitivity reactions (receptor mediated autoimmune disease), including e.g. Graves' disease, Myasthenia Gravis, etc.;

In a further preferred embodiment, the inventive vaccine may be formulated as a kit, preferably as a kit of part. Accordingly, the present invention also provides kits, particularly kits of parts, comprising the components of the inventive vaccine either alone or in combination with further ingredients as defined above, and optionally technical instructions with information on the administration and dosage of the inventive vaccine. The components of the inventive vaccine either alone or in combination with further ingredients as defined above may be contained in the kit in either one part of the kit or in different parts of the kit, e.g. each at least one mRNA encoding at least one antigen as defined above in one part of the kit, and preferably further components admixed to the each at least one mRNA encoding at least one antigen or separately in a further part of the kit. Such kits, preferably kits of parts, may be applied, e.g., for any of the above mentioned applications or uses.

In the present invention, if not otherwise indicated, different features of alternatives and embodiments may be combined with each other, where suitable. Furthermore, the term "comprising" shall not be construed as meaning "consisting of", if not specifically mentioned. However, in the context of the present invention, term "comprising" may be substituted with the term "consisting of", where suitable.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modi-

FIGURES

The following Figures are intended to illustrate the invention further. They are not intended to limit the subject matter of the invention thereto.

FIG. 1 A: shows the development of the weight of the mice in the experiment. As a result newborn mice vaccinated with mRNA coding for PR8 H1 Hemagglutinin exhibited a significantly better survival (all mice survived) against influenza challenge infection with control mRNA only (all mice died about 5 days subsequent to vaccination with control mRNA encoding chicken ovalbumin, when vaccinated with control mRNA at the first day 8 weeks and died about 6 days subsequent to vaccination with control mRNA, when vaccinated with 8 weeks). Most surprisingly, the survival rate was comparable to that of adult mice.

FIG. 1 B, C show the coding sequence of the mRNAs used for vaccination of newborn and 8 weeks old mice (see FIG. 1A) coding for PR8 H1 HA (Hemagglutinin of influenza virus A/Puerto Rico/8/1934) (SEQ ID NO: 384) (FIG. 1B) or for *Gallus gallus* ovalbumine as a control (control mRNA) (SEQ ID NO: 385) (FIG. 1C)

EXAMPLES

The following examples are intended to illustrate the invention further. They are not intended to limit the subject matter of the invention thereto.

Example 1

Preparation of mRNA Constructs

For the present examples DNA sequences, encoding PR8 H1 HA (Haemagglutinin of A/Puerto Rico/8/1934) (SEQ ID NO: 384), and *Gallus gallus* ovalbumine, respectively, as a control (control mRNA) (SEQ ID NO: 385), were prepared and used for subsequent in vitro transcription reactions.

According to a first preparation, the DNA sequence termed PR8 H1 HA (Haemagglutinin of A/Puerto Rico/8/1934) (SEQ ID NO: 384) (see FIG. 1B) was prepared by modifying the wildtype Haemagglutinin encoding DNA sequence by introducing a GC-optimized sequence for a better codon usage and stabilization. In SEQ ID NO: 384 (see FIG. 1B) the sequence of the corresponding mRNA is shown. The sequence was furthermore introduced into a pCV19 vector and modified to comprise stabilizing sequences derived from alpha-globin-3'-UTR (muag (mutated alpha-globin-3'-UTR)), a stretch of 70×adenosine at the 3'-terminal end (poly-A-tail) and a stretch of 30×cytosine at the 3'-terminal end (poly-C-tail). The sequence of the final DNA construct was termed "PR8 H1 HA".

According to a second preparation, the DNA sequence termed *Gallus gallus* ovalbumine, respectively, as a control (control mRNA) (SEQ ID NO: 385) (see FIG. 1C) was prepared by modifying the wildtype *Gallus gallus* ovalbumine encoding DNA sequence by introducing a GC-optimized sequence for a better codon usage and stabilization. In SEQ ID NO: 385 (see FIG. 1C) the sequence of the corresponding mRNA is shown. The sequence was furthermore introduced into a pCV19 vector and modified to comprise stabilizing sequences derived from alpha-globin-3'-UTR (muag (mutated alpha-globin-3'-UTR)), a stretch of 70×adenosine at the 3'-terminal end (poly-A-tail) and a stretch of 30×cytosine at the 3'-terminal end (poly-C-tail). The sequence of the final DNA construct was termed "*Gallus gallus* ovalbumine".

In a further step, the respective DNA plasmids prepared above were transcribed into mRNA in vitro using T7-Polymerase. Subsequently the obtained mRNA was purified using PUREMESSENGER® (CureVac, Tübingen, Germany).

All obtained mRNAs used herein were furthermore complexed with protamine prior to use. The RNA complexation consisted of a mixture of 50% free mRNA and 50% mRNA complexed with protamine at a weight ratio of 2:1. First, mRNA was complexed with protamine by slow addition of protamine-Ringer's lactate solution to mRNA. As soon as the complexes were stably generated, free mRNA was added, stirred shortly and the final concentration of the vaccine was adjusted with Ringer's lactate solution.

Example 2

Vaccination of Newborn and 8 Weeks Old Mice

In this experiment newborn or 8 weeks old mice were vaccinated twice intradermally with 80 μg mRNA coding for PR8 H1 HA (Hemagglutinin of A/Puerto Rico/8/1934; FIG. 1B) or with mRNA coding for *Gallus gallus* ovalbumine as a control (control mRNA; FIG. 1C). The first injection was carried out at the first day of life (≤24 h) and with 8 weeks, respectively. 5 weeks after the last vaccination the mice were challenged with a 10 fold median lethal dose of PR8 virus (10 LD50). The weight of the mice was controlled over 2 weeks and the mice were killed when they have lost more than 25% of their original weight. The results are shown in FIG. 1A. FIG. 1A shows the development of the weight of the mice in the experiment. As a result mice vaccinated with mRNA coding for PR8 H1 Hemagglutinin exhibited a significantly better survival (all mice survived) against influenza challenge infection with control mRNA only (all mice in the control experiment died about 5 days subsequent to vaccination with control mRNA encoding chicken ovalbumin, when vaccinated with control mRNA at the first day and died about 6 days subsequent to vaccination with control mRNA, when vaccinated with 8 weeks). All vaccinated newborn mice survived antigen challenge with PR8 H1 Hemagglutinin in contrast to the control.

The invention claimed is:

1. A method for stimulating an immune response in an infant subject comprising, administering an effective amount of a composition comprising a purified mRNA encoding an influenza hemagglutinin (HA) virus antigen to the infant subject thereby stimulating an antigen-specific Th1 immune response in the subject, said infant subject being no more than 2 years of age, wherein the composition is administered via injection.

2. The method of claim 1, wherein the mRNA comprises an increased G/C content relative to a wild type RNA encoding the antigen, a cap and/or a polyA tail.

3. The method of claim 1, wherein the subject is no more than 1 year of age.

4. The method of claim 3, wherein the subject is no more than 6 months of age.

5. The method of claim 1, wherein the composition is administered parenterally.

6. The method of claim 1, wherein the composition is administered intradermally.

7. The method of claim 1, wherein the composition comprises the mRNA in an aqueous solution.

8. The method of claim 7, wherein the aqueous solution is a Ringer's lactate solution.

9. The method of claim 1, wherein at least a portion of the mRNA is complexed with a cationic or polycationic compound.

10. The method of claim 9, wherein a portion of the mRNA is complexed with the cationic or polycationic compound and a portion of the mRNA is free from complex.

11. The method of claim 9, wherein the cationic or polycationic compound is a polypeptide.

12. The method of claim 11, wherein the polypeptide is protamine.

13. The method of claim 1, wherein at least a portion of the mRNA encoding the antigen is complexed with a polymeric carrier formed by disulphide-crosslinked cationic polypeptides.

14. The method of claim 1, further comprising administering an adjuvant to the infant subject.

15. The method of claim 14, wherein the adjuvant is an immunostimulatory RNA (isRNA).

* * * * *

UNITED STATES PATENT AND TRADEMARK OFFICE
CERTIFICATE OF CORRECTION

PATENT NO. : 9,623,095 B2
APPLICATION NO. : 13/824705
DATED : April 18, 2017
INVENTOR(S) : Kallen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this
Twenty-fifth Day of September, 2018

Andrei Iancu
*Director of the United States Patent and Trademark Office*